United States Patent
Joao

(10) Patent No.: US 11,587,688 B2
(45) Date of Patent: Feb. 21, 2023

(54) APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK

(71) Applicant: Raymond Anthony Joao, Yonkers, NY (US)

(72) Inventor: Raymond Anthony Joao, Yonkers, NY (US)

( * ) Notice: Subject to any disclaimer, the term of this patent is extended or adjusted under 35 U.S.C. 154(b) by 429 days.

(21) Appl. No.: 16/202,448

(22) Filed: Nov. 28, 2018

(65) Prior Publication Data

US 2019/0096534 A1    Mar. 28, 2019

Related U.S. Application Data

(63) Continuation-in-part of application No. 14/638,934, filed on Mar. 4, 2015, now abandoned.
(Continued)

(51) Int. Cl.
*G16H 80/00* (2018.01)
*G16H 10/60* (2018.01)
(Continued)

(52) U.S. Cl.
CPC ............ *G16H 80/00* (2018.01); *G16H 10/60* (2018.01); *G16H 15/00* (2018.01); *G16H 40/20* (2018.01); *G16H 40/67* (2018.01); *H04L 12/1818* (2013.01); *H04L 12/1831* (2013.01); *H04L 65/403* (2013.01); *H04N 7/147* (2013.01); *H04N 7/155* (2013.01)

(58) Field of Classification Search
CPC ......... G16H 80/00; G16H 40/60; G16H 10/60
See application file for complete search history.

(56) References Cited

U.S. PATENT DOCUMENTS

3,978,850 A    9/1976 Moore et al.
4,110,723 A    8/1978 Hetz et al.
(Continued)

OTHER PUBLICATIONS

U.S. Appl. No. 09/489,657, Joao, et al.
(Continued)

*Primary Examiner* — Jonathan Durant
(74) *Attorney, Agent, or Firm* — Raymond A. Joao, Esq.

(57) ABSTRACT

An apparatus, including a memory or a database which stores an electronic healthcare record of or for an individual or a patient a comment, note, or message, in advance of a video call, and information regarding an appointment for or regarding the video call; a processor which generates an appointment message or reminder message containing information regarding the appointment and containing a link or hyperlink for initiating the video call, wherein the video call is initiated via the link or the hyperlink; a receiver which receives information regarding the individual or the patient during the video call, receives information input into or entered into a provider communication device or a user communication device, wherein the processor or a computer generates a report containing information regarding the video call; and a transmitter, wherein the transmitter transmits the report to the user communication device.

13 Claims, 12 Drawing Sheets

Related U.S. Application Data

(60) Provisional application No. 61/971,225, filed on Mar. 27, 2014.

(51) Int. Cl.

| | | |
|---|---|---|
| H04N 7/14 | (2006.01) | |
| H04N 7/15 | (2006.01) | |
| G16H 40/20 | (2018.01) | |
| H04L 12/18 | (2006.01) | |
| G16H 40/67 | (2018.01) | |
| H04L 65/403 | (2022.01) | |
| G16H 15/00 | (2018.01) | |

(56) References Cited

U.S. PATENT DOCUMENTS

| | | |
|---|---|---|
| 4,170,987 A | 10/1979 | Anselmo et al. |
| 4,209,022 A | 6/1980 | Dory |
| 4,235,454 A | 11/1980 | Gray et al. |
| 4,242,911 A | 1/1981 | Martin |
| 4,251,850 A | 2/1981 | Kalbitz et al. |
| 4,290,114 A | 9/1981 | Sinay |
| 4,491,725 A | 1/1985 | Pritchard |
| 4,641,659 A | 2/1987 | Sepponen |
| 4,648,036 A | 3/1987 | Gallant |
| 4,674,108 A | 6/1987 | Asahina et al. |
| 4,674,512 A | 6/1987 | Rolf |
| 4,731,725 A | 3/1988 | Suto et al. |
| 4,733,354 A | 3/1988 | Potter et al. |
| 4,803,625 A | 2/1989 | Fu et al. |
| 4,803,652 A | 2/1989 | Maeser et al. |
| 4,835,372 A | 5/1989 | Gombrich et al. |
| 4,858,121 A | 8/1989 | Barber |
| 4,895,518 A | 1/1990 | Arnold et al. |
| 4,987,538 A | 1/1991 | Johnson et al. |
| 5,036,852 A | 8/1991 | Leishman |
| 5,070,452 A | 12/1991 | Doyle, Jr. et al. |
| 5,090,417 A | 2/1992 | Mollan et al. |
| 5,185,857 A | 2/1993 | Rozmanith et al. |
| 5,217,379 A | 6/1993 | Kirschenbaum et al. |
| 5,219,322 A | 6/1993 | Weathers |
| 5,235,510 A | 8/1993 | Yamada et al. |
| 5,255,187 A | 10/1993 | Sorensen |
| 5,262,943 A | 11/1993 | Thibado et al. |
| 5,265,010 A | 11/1993 | Evans-Paganelli et al. |
| 5,279,294 A | 1/1994 | Anderson et al. |
| 5,283,761 A | 2/1994 | Gillingham |
| 5,301,105 A | 4/1994 | Cummings, Jr. |
| 5,305,748 A | 4/1994 | Wilk |
| 5,324,077 A | 6/1994 | Kessler et al. |
| 5,325,293 A | 6/1994 | Dorne |
| 5,331,550 A | 7/1994 | Stafford et al. |
| 5,344,324 A | 9/1994 | O'Donnell et al. |
| 5,360,005 A | 11/1994 | Wilk |
| 5,404,292 A | 4/1995 | Hendrickson |
| 5,415,167 A | 5/1995 | Wilk |
| 5,424,945 A | 6/1995 | Bell |
| 5,435,324 A | 7/1995 | Brill |
| 5,437,278 A | 9/1995 | Wilk |
| 5,465,082 A | 11/1995 | Chaco |
| 5,519,607 A | 5/1996 | Tawil |
| 5,530,438 A | 6/1996 | Bickham et al. |
| 5,544,649 A | 8/1996 | David et al. |
| 5,544,651 A | 8/1996 | Wilk |
| 5,551,436 A | 9/1996 | Yago |
| 5,583,758 A | 12/1996 | McIlroy et al. |
| 5,594,638 A | 1/1997 | Iliff |
| 5,615,110 A | 3/1997 | Wong |
| 5,644,778 A | 7/1997 | Burks |
| 5,654,750 A | 8/1997 | Weil |
| 5,660,176 A | 8/1997 | Iliff |
| 5,666,953 A | 9/1997 | Wilk |
| 5,696,981 A | 12/1997 | Shovers |
| 5,708,422 A | 1/1998 | Blonder et al. |
| 5,724,968 A | 3/1998 | Iliff |
| 5,730,146 A | 3/1998 | Itil et al. |
| 5,737,539 A | 4/1998 | Edelson et al. |
| 5,748,907 A | 5/1998 | Crane |
| 5,754,111 A | 5/1998 | Garcia |
| 5,761,334 A | 6/1998 | Nakajima et al. |
| 5,772,585 A | 6/1998 | Lavin et al. |
| 5,776,057 A | 7/1998 | Swenson et al. |
| 5,779,634 A | 7/1998 | Ema et al. |
| 5,797,901 A | 8/1998 | Cosmescu |
| 5,801,755 A | 9/1998 | Echerer |
| 5,807,246 A | 9/1998 | Sakaguchi et al. |
| 5,807,256 A | 9/1998 | Taguchi et al. |
| 5,807,336 A | 9/1998 | Russo et al. |
| 5,839,438 A | 11/1998 | Graettinger et al. |
| 5,845,255 A | 12/1998 | Mayaud |
| 5,862,803 A | 1/1999 | Besson et al. |
| 5,867,821 A | 2/1999 | Ballantyne et al. |
| 5,868,669 A | 2/1999 | Iliff |
| 5,876,351 A | 3/1999 | Rohde |
| 5,878,337 A | 3/1999 | Joao et al. |
| 5,878,746 A | 3/1999 | Lemelson et al. |
| 5,890,129 A | 3/1999 | Spurgeon |
| 5,895,354 A | 4/1999 | Simmons |
| 5,899,857 A | 5/1999 | Wilk |
| 5,903,830 A | 5/1999 | Joao et al. |
| 5,910,107 A | 6/1999 | Iliff |
| 5,915,241 A | 6/1999 | Giannini |
| 5,917,405 A | 6/1999 | Joao |
| 5,930,759 A | 7/1999 | Moore et al. |
| 5,935,060 A | 8/1999 | Iliff |
| 5,942,986 A | 8/1999 | Shabot et al. |
| 5,946,659 A | 8/1999 | Lancelot et al. |
| 5,954,641 A | 9/1999 | Kehr et al. |
| 5,957,854 A | 9/1999 | Besson et al. |
| 5,961,332 A | 10/1999 | Joao |
| 5,961,448 A | 10/1999 | Swenson et al. |
| 5,974,124 A | 10/1999 | Schlueter, Jr. et al. |
| 5,974,389 A | 10/1999 | Clarke et al. |
| 5,988,851 A | 11/1999 | Gent |
| 5,992,742 A | 11/1999 | Sullivan et al. |
| 6,003,007 A | 12/1999 | DeRienzo |
| 6,014,629 A | 1/2000 | Debruin-Ashton |
| 6,018,713 A | 1/2000 | Coli et al. |
| 6,021,202 A | 2/2000 | Anderson et al. |
| 6,044,352 A | 3/2000 | Deavers |
| 6,047,259 A | 4/2000 | Campbell et al. |
| 6,047,270 A | 4/2000 | Joao et al. |
| 6,073,106 A | 6/2000 | Rozen et al. |
| 6,076,066 A | 6/2000 | DiRienzo et al. |
| 6,090,044 A | 7/2000 | Bishop et al. |
| 6,101,478 A | 8/2000 | Brown |
| 6,208,973 B1 | 3/2001 | Boyer et al. |
| 6,216,104 B1 | 4/2001 | Moshfeghi et al. |
| 6,273,856 B1 | 8/2001 | Sun et al. |
| 6,283,761 B1 | 9/2001 | Joao |
| 6,302,844 B1 | 10/2001 | Walker et al. |
| 6,341,265 B1 | 1/2002 | Provost et al. |
| 6,343,271 B1 | 1/2002 | Peterson et al. |
| 6,345,260 B1 | 2/2002 | Cummings et al. |
| 6,364,834 B1 | 4/2002 | Reuss et al. |
| 6,476,833 B1 | 11/2002 | Moshfeghi |
| 6,484,144 B2 | 11/2002 | Martin et al. |
| 6,523,009 B1 | 2/2003 | Wilkins |
| 6,529,725 B1 | 3/2003 | Joao et al. |
| 6,542,076 B1 | 4/2003 | Joao |
| 6,542,077 B2 | 4/2003 | Joao |
| 6,549,130 B1 | 4/2003 | Joao |
| 6,587,046 B2 | 7/2003 | Joao |
| 6,662,194 B1 | 12/2003 | Joao |
| 6,757,898 B1 | 6/2004 | Ilsen et al. |
| 6,776,341 B1 | 8/2004 | Sullivan et al. |
| 6,799,725 B1 | 10/2004 | Hess et al. |
| 6,804,558 B2 | 10/2004 | Haller et al. |
| 6,804,656 B1 | 10/2004 | Rosenfeld et al. |
| 6,845,448 B1 | 1/2005 | Chaganti et al. |
| 6,915,265 B1 | 7/2005 | Johnson |
| 6,988,075 B1 | 1/2006 | Hacker |
| 7,028,049 B1 | 4/2006 | Shelton |
| 7,059,526 B1 | 6/2006 | Sullivan et al. |

(56) References Cited

U.S. PATENT DOCUMENTS

| | | |
|---|---|---|
| 7,096,003 B2 | 8/2006 | Joao et al. |
| 7,110,955 B1 | 9/2006 | Barhnart et al. |
| 7,149,773 B2 | 12/2006 | Haller et al. |
| 7,181,505 B2 | 2/2007 | Haller et al. |
| 7,194,416 B1 | 3/2007 | Provost et al. |
| 7,277,010 B2 | 10/2007 | Joao |
| 7,370,797 B1 | 5/2008 | Sullivan et al. |
| 7,397,363 B2 | 7/2008 | Joao |
| 7,464,040 B2 | 12/2008 | Joao |
| 7,464,043 B1 | 12/2008 | Dussia |
| 7,490,048 B2 | 2/2009 | Joao |
| 7,593,952 B2 | 9/2009 | Soll et al. |
| 7,647,234 B1 | 1/2010 | Ruderman et al. |
| 7,685,005 B2 | 3/2010 | Riff et al. |
| 7,698,154 B2 | 4/2010 | Marchosky |
| 8,131,563 B2 | 3/2012 | Hasan et al. |
| 8,316,237 B1 | 11/2012 | Felsher et al. |
| 8,606,594 B2 | 12/2013 | Stern et al. |
| 8,793,142 B2 | 7/2014 | Fishman et al. |
| 8,852,093 B2 | 10/2014 | Clapp et al. |
| 8,905,927 B2 | 12/2014 | Cheung et al. |
| 9,235,841 B2 | 1/2016 | Joao |
| 9,245,270 B2 | 1/2016 | Joao |
| 9,465,913 B1 | 10/2016 | Chaganti et al. |
| 9,759,570 B2 | 9/2017 | Joao et al. |
| 9,911,124 B2 | 3/2018 | Joao |
| 9,961,249 B2 | 5/2018 | Joao et al. |
| 10,011,247 B2 | 7/2018 | Joao |
| 10,048,078 B2 | 8/2018 | Joao et al. |
| 10,152,876 B2 | 12/2018 | Joao |
| 10,157,385 B2 | 12/2018 | Joao |
| 10,197,406 B2 | 2/2019 | Joao et al. |
| 10,218,888 B2 | 2/2019 | Joao et al. |
| 10,504,123 B2 | 12/2019 | Joao |
| 10,562,492 B2 | 2/2020 | Joao |
| 10,571,284 B2 | 2/2020 | Joao et al. |
| 10,791,256 B2 | 9/2020 | Joao et al. |
| 10,861,020 B2 | 12/2020 | Joao |
| 10,942,032 B2 | 3/2021 | Joao et al. |
| 2001/0032099 A1 | 10/2001 | Joao |
| 2001/9932099 | 10/2001 | Joao |
| 2001/0037220 A1 | 11/2001 | Merry et al. |
| 2001/0041991 A1 | 11/2001 | Segal et al. |
| 2001/0049610 A1 | 12/2001 | Hazumi |
| 2001/0051787 A1 | 12/2001 | Haller et al. |
| 2001/0051920 A1 | 12/2001 | Joao et al. |
| 2002/0004725 A1 | 1/2002 | Martin et al. |
| 2002/0004727 A1 | 1/2002 | Knaus et al. |
| 2002/0025797 A1 | 2/2002 | Joao et al. |
| 2002/0026332 A1 | 2/2002 | Snowden et al. |
| 2002/0029157 A1 | 3/2002 | Marchosky |
| 2002/0032583 A1 | 3/2002 | Joao |
| 2002/0038424 A1 | 3/2002 | Joao et al. |
| 2002/0052539 A1 | 5/2002 | Haller et al. |
| 2002/0087113 A1 | 7/2002 | Hartlaub |
| 2002/0120471 A1 | 8/2002 | Drazen |
| 2002/0161795 A1 | 10/2002 | O'Rourke |
| 2002/0194027 A1 | 12/2002 | Smith |
| 2003/0028399 A1 | 2/2003 | Davis et al. |
| 2003/0055679 A1 | 3/2003 | Soll et al. |
| 2003/0069752 A1 | 4/2003 | Ledain et al. |
| 2003/0069760 A1 | 4/2003 | Gelber |
| 2003/0074248 A1 | 4/2003 | Braud et al. |
| 2003/0110215 A1 | 6/2003 | Joao |
| 2003/0144711 A1 | 7/2003 | Pless et al. |
| 2003/0158754 A1 | 8/2003 | Elkind |
| 2003/0208391 A1 | 11/2003 | Dvorak et al. |
| 2003/0212579 A1 | 11/2003 | Brown et al. |
| 2004/0044546 A1 | 3/2004 | Moore |
| 2004/0083395 A1 | 4/2004 | Blechman |
| 2004/0107192 A1 | 6/2004 | Joao |
| 2004/0139044 A1 | 7/2004 | Rehwald |
| 2004/0185830 A1 | 9/2004 | Joao et al. |
| 2004/0199765 A1 | 10/2004 | Kohane et al. |
| 2004/0215492 A1 | 10/2004 | Choi |
| 2004/0249665 A1 | 12/2004 | David |
| 2005/0021370 A1 | 1/2005 | Riff et al. |
| 2005/0033604 A1 | 2/2005 | Hogan |
| 2005/0115561 A1 | 6/2005 | Stahmann et al. |
| 2005/0170814 A1 | 8/2005 | Joao et al. |
| 2005/0187789 A1 | 8/2005 | Hatlestad et al. |
| 2005/0192844 A1 | 9/2005 | Esler et al. |
| 2005/0222875 A1 | 10/2005 | Lordeman et al. |
| 2006/0287885 A1 | 12/2006 | Frick |
| 2006/0293570 A1 | 12/2006 | Croghan et al. |
| 2007/0013529 A1 | 1/2007 | Kantrowitz et al. |
| 2007/0122824 A1 | 5/2007 | Tucker |
| 2007/0250352 A1 | 10/2007 | Tawil |
| 2007/0260484 A1 | 11/2007 | Kimmel |
| 2007/0294105 A1 | 12/2007 | Pierce |
| 2007/0299349 A1 | 12/2007 | Alt et al. |
| 2008/0059249 A1 | 3/2008 | Joao |
| 2008/0059250 A1 | 3/2008 | Joao |
| 2008/0097786 A1 | 4/2008 | Sachdeva |
| 2008/0120190 A1 | 5/2008 | Joao et al. |
| 2008/0126131 A1 | 5/2008 | Lou |
| 2008/0176203 A1 | 7/2008 | Kuntz et al. |
| 2008/0188198 A1 | 8/2008 | Patel et al. |
| 2009/0023555 A1 | 1/2009 | Raymond |
| 2009/0025081 A1 | 1/2009 | Quigley et al. |
| 2009/0060148 A1 | 3/2009 | Jacob et al. |
| 2009/0075630 A1 | 3/2009 | McLean |
| 2009/0269329 A1 | 10/2009 | Hyde et al. |
| 2009/0281833 A1 | 11/2009 | Boppana |
| 2009/0298650 A1 | 12/2009 | Kutliroff |
| 2009/0313049 A1 | 12/2009 | Joao et al. |
| 2010/0042440 A1 | 2/2010 | Joao |
| 2010/0063930 A1 | 3/2010 | Kenedy et al. |
| 2010/0114602 A1 | 5/2010 | Joao et al. |
| 2010/0174505 A1 | 7/2010 | Abraham-Fuchs et al. |
| 2010/0292556 A1 | 11/2010 | Golden |
| 2011/0010200 A1 | 1/2011 | Firozvi et al. |
| 2011/0015693 A1 | 1/2011 | Williamson |
| 2011/0029327 A1 | 2/2011 | Dunlop |
| 2011/0166988 A1 | 7/2011 | Coulter |
| 2011/0184249 A1 | 7/2011 | Davis, Jr. |
| 2011/0213625 A1* | 9/2011 | Joao .............. G06F 16/9535 705/3 |
| 2011/0276396 A1 | 11/2011 | Rathod |
| 2012/0029303 A1* | 2/2012 | Shaya .............. G16H 40/67 600/300 |
| 2012/0253848 A1* | 10/2012 | Gazula .............. G16H 30/20 705/3 |
| 2013/0066653 A1 | 3/2013 | Joao et al. |
| 2013/0090949 A1 | 4/2013 | Tibebu |
| 2013/0218582 A1* | 8/2013 | LaLonde .............. A61B 5/686 705/2 |
| 2014/0067423 A1 | 3/2014 | Joao |
| 2014/0081667 A1 | 3/2014 | Joao |
| 2014/0108055 A1* | 4/2014 | Phillips .............. G16H 80/00 705/3 |
| 2014/0364230 A1 | 12/2014 | Borghese et al. |
| 2015/0004581 A1 | 1/2015 | Selman et al. |
| 2015/0033305 A1 | 1/2015 | Shear et al. |
| 2015/0077502 A1* | 3/2015 | Jordan .............. G16H 80/00 348/14.03 |
| 2015/0112702 A1 | 4/2015 | Joao et al. |
| 2015/0151199 A1 | 6/2015 | Klein et al. |
| 2015/0161330 A1 | 6/2015 | Joao et al. |
| 2015/0248536 A1 | 9/2015 | Tawil et al. |
| 2015/0278453 A1 | 10/2015 | Joao |
| 2015/0331997 A1 | 11/2015 | Joao |
| 2016/0042651 A1 | 2/2016 | Joao |
| 2016/0125549 A1 | 5/2016 | Joao et al. |
| 2016/0125550 A1 | 5/2016 | Joao et al. |
| 2016/0342744 A1 | 11/2016 | Joao |
| 2017/0011190 A1 | 1/2017 | Joao |
| 2017/0091397 A1* | 3/2017 | Shah .............. G06Q 50/01 |
| 2017/0300627 A1* | 10/2017 | Giordano .............. G06F 21/6245 |
| 2018/0190136 A1 | 7/2018 | Joao |
| 2018/0233237 A1 | 8/2018 | Joao et al. |
| 2019/0096534 A1 | 3/2019 | Joao |

(56) References Cited

U.S. PATENT DOCUMENTS

2020/0184838 A1   6/2020  Joao
2021/0319895 A1  10/2021  Joao

OTHER PUBLICATIONS

U.S. Appl. No. 60/172,555, Joao.
L. McCullough et al., "The Development of a Microcomputer-Based Mental Health Information System, a Potential Tool for Bridging the Scientist-Practitioner Gap" American Psychologist, Feb. 1986, pp. 207-213.
Watson, the Doctor is in!, Jun. 1995, Accounting Technology, vol. 11, ISS. 5, pp. 24-30.
Edicomm Unveils All-Payer Solution for Healthcare EDI Transactions, Feb. 1999, Business Wire.
U.S. Appl. No. 60/169,065, filed Dec. 6, 1999, Snowden, et al.
U.S. Appl. No. 60/235,977, filed Sep. 28, 2000, Davis, et al.
Medsys Preliminary Invalidity Contentions.
Joint MSS Invalidity Contentions.
Joint Athena Invalidity Contentions.
Grumitt, "Real-Time Record Management in General Practice," 8 Int'l J. Bio-Medical Computing 131 (1977), Apr. 1977.
Wang, et al., "A Real Time Patient Monitoring System on the World Wide Web," Proc. AMIA Annual Fall Symp. 729 (1996).
Universal Software Solutions, Inc., Proposal For Practice Management Software, Jun. 16, 2000.
VersaVision, Ophthalmic Practice Management Software, User Guide, Copyright 2000, Universal Software Solutions, Inc.
Employee Scheduler Information.
Christus Health Invalidity Contentions.

\* cited by examiner

APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK

RELATED APPLICATIONS

This application is a continuation-in-part application of U.S. patent application Ser. No. 14/638,934, filed Mar. 4, 2015, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety. U.S. patent application Ser. No. 14/638,934 claims the benefit of the priority of U.S. Provisional Patent Application Ser. No. 61/971,225, filed Mar. 27, 2014, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

FIELD OF THE INVENTION

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional.

BACKGROUND OF THE INVENTION

Healthcare is an area of major concern in the United States. Each year, tens of millions of individuals seek or need the assistance of healthcare professionals. In order to perform proper diagnoses and to prescribe appropriate treatments, healthcare professional or providers typically rely on information which is obtained from patients, relatives of patients, previous providers, and/or healthcare facility and/or hospital staff members. The need to have accurate and/or up-to-date data and/or information, in providing healthcare services and/or healthcare-related services, cannot be emphasized enough.

Stories constantly emerge about patients receiving the wrong treatments, having the wrong surgical procedures performed on themselves, receiving a drug or drugs which fatally and/or otherwise adversely interact with another drug or drugs, etc., with stories going on and on. A 1999 study estimated that between 44,000 and 98,000 individuals die annually in hospitals, in the United States alone, as the result of errors or mistakes made by doctors, healthcare providers, and/or healthcare facility workers. Various other reports also estimate 225,000 deaths annually from medical errors and 180,000 deaths annually from medication errors and adverse reactions. There is no doubt that many of these deaths result from inaccurate and/or erroneous information and/or the lack of the availability of correct and/or up-to-date information.

Another problem lies with the fact that the main source of patient information, medical histories, family histories, etc., upon which doctors or providers may base their diagnoses and/or treatments, are patients who usually supply this information on questionnaires or forms just prior to seeing the healthcare provider and/or during a preliminary interview with the provider. In this regard, information obtained from these questionnaires or forms, as well as from these preliminary interviews with the providers, may not necessarily result in sufficient, comprehensive, and/or accurate, information being obtained regarding the patient. Further, there is no guarantee that the same information will be provided, in a uniform manner, to a next or different provider. As a result, patient information may not be uniformly distributed and/or be available to providers at the point of treatment and/or otherwise.

Another problem which exists in the current healthcare system is that doctors or other providers do not always have the latest information and/or research material available to them prior to, and/or during, the diagnosis and/or treatment process.

Still other problems arise when an individual or a patient, or a caregiver for an individual or a patient, engages in a video call with a healthcare provider in or during a remote or a virtual provider visit or in or during a remote or a distance examination. In such instances, there is no guarantee that the healthcare provider has access to the individual's or the patient's healthcare records, files, or history, before or during the video call and the remote or virtual provider visit or in or during the remote or distance examination. Further, there is no guarantee that the healthcare provider, even if provided with access to the individual's or the patient's healthcare records, files, or history, can access the same, and enter notes, findings, and/or information, into the same in an easy and efficient manner, and/or be able to do so in, during, or after the remote or distance examination. As a result, the healthcare provider may be not be provided with sufficient information to conduct a full and complete examination or evaluation of the individual or the patient, or to make or arrive at a diagnosis based on any and/or all needed and available information regarding the individual or the patient, or to prescribed a treatment based on any and/or all needed or available information regarding the individual or the patient. As a further result, the healthcare provider may not have access to the individual's or the patient's healthcare records, files, or history, in order to properly or completely enter notes or any other information regarding the individual or the patient as well as any information, observations, examination findings, or examinations results, obtained by, made by, or obtained during the remote or the virtual provider visit or in or during the remote or the distance examination.

Another problem associated with healthcare providers and patients who engage in video calls during remote or virtual provider visits or in or during remote or distance examinations lies in the fact that the healthcare provider may not able to control and/or to monitor healthcare equipment, devices, or systems, which is located with the patient. In such instances, patient control and/or operation of such healthcare equipment, devices, or systems, might fail to yield measurements or results if uncalibrated and/or misused by patients or their caregivers.

Another problems also lies in securing data and/or information stored in patient's healthcare records, files, or history, especially when data and/or information may be accessed via the online networks and/or the Internet and/or the World Wide Web.

SUMMARY OF THE INVENTION

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional, which overcomes the shortcomings of the prior art.

The present invention is directed to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional for a variety of healthcare and healthcare-related applications.

The apparatus and method of the present invention can be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribed a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

The present invention facilitates improved healthcare quality, efficient information collection, processing and dissemination, efficient diagnosis and treatment, cost efficiency, cost containment, as well as many other benefits and advantages as will be described herein. The apparatus and method of the present invention can also facilitate the distribution and management of healthcare insurance, life insurance, disability insurance, as well as claims processing related thereto.

The present invention also provides an apparatus and a method for providing a comprehensive processing system which incorporates data and/or information from any combination and/or all of the participants in the healthcare field, including patients, providers, payers or insurance companies, and/or brokers, agents and/or other intermediaries who act on behalf of any of the above-identified persons or entities.

The apparatus of the present invention includes a central processing computer or central processing computer system which can be a network or server computer. The apparatus also includes a healthcare provider communication device or computer which is associated with a healthcare provider such as a healthcare professional, a hospital, a clinic, and/or any other provider of services described herein. The healthcare provider computer(s) can communicate with, and operate in conjunction with, the central processing computer and/or any of the other computers and/or computer systems or communication devices described herein.

The apparatus can also include a healthcare payer communication device or computer which is associated with a healthcare payer such as a healthcare insurer, insurance company, health maintenance organization, a clinic, and/or any other payer of healthcare services and products described herein. The healthcare payer computer(s) can communicate with, and operate in conjunction with, central processing computer and/or any of the other computers and/or computer systems or communication devices described herein.

The apparatus can also include a user or patient communication device or computer which is associated with an individual, or patient, or a caregiver of the individual or patient, who seeks or who is provided with healthcare and/or related services, products and/or related information. The user or patient communication device(s) can communicate with, and operate in conjunction with, central processing computer and/or any of the other computers and/or computer systems described herein.

The apparatus can also include an intermediary communication device or computer which is associated with an intermediary, a broker, an agent, and/or any other individual and/or entity, or any third party, that can utilize the present invention in order to act for and/or on behalf of any other individual, party, or entity, described herein. The intermediary computer(s) can communicate with, and operate in conjunction with, central processing computer and any of the other computers and/or computer systems described herein.

The apparatus can also include a healthcare records computer which can be or can include a computer or computer system, or any number of computers or computer systems, or a cloud computer system or cloud system. The healthcare records computer can serve to store and house an electronic healthcare record or electronic healthcare files or any number of electronic healthcare records or electronic healthcare files. The healthcare records computer can be associated with any provider, insurer, payer, intermediary, insurance exchange, or any user, individual, patient, organization, or entity, who or which utilizes the present invention.

Each healthcare records computer can be utilized to store an electronic healthcare record or electronic healthcare file or any number of electronic healthcare records or electronic healthcare files which can be accessed by the central processing computer, by any provider communication device, by any insurer or payer communication device, by any user or patient communication device, by any intermediary communication device, or by any other computer, communication device or other device described herein as being utilized in connection with the present invention. The healthcare records computer can also be utilized to facilitate cloud storage of any electronic healthcare record(s) or electronic healthcare file(s).

The apparatus can also include an insurance exchange computer, or any number of insurance exchange computers which can be utilized to process and store information regarding the selling of healthcare insurance, disability insurance, and life insurance, policies, products, and/or services, to any of the herein-described users, individuals, patients, or entities, who or which utilize the apparatus 100 and method of the present invention. The insurance exchange computer can be utilized to advertise, provide information regarding, sell, and/or maintain records regarding, and process any other information regarding, group insurance as well as individual or family insurance policies, products, or services. The insurance exchange computer can also be utilized to sell automobile, homeowners, business, and/or liability insurance policies, products, or services.

The apparatus can also include a social networking computer. The social networking computer can be linked with, and utilized in connection with, the apparatus so as to allow and/or facilitate integrating the apparatus of the present invention with social networks, social networking, and social media. The social networking computer can be associated with a social networking company, a social networking website, or social networking entity, website, group, organization, or association. The social networking computer can also be associated with any one or any number of social networking companies, social networking websites, or social networking entities, websites, groups, organizations, or associations. The social networking computer can also provide links to any computers associated with any one or any number of social networking companies, social networking websites, or social networking entities, websites, groups, organizations, or associations. The social networking computer can perform any and all of the functions performed by any social networking company, a social networking website, or social networking entity, website, group, organization, or association. Any number of social networking computers can be utilized in connection with the present invention.

The apparatus can also include a media computer. The media computer can provide, and be a source of, news information, current events information, healthcare information, healthcare or healthcare-related news, current events, advertisements, and/or marketing information or materials, which can be disseminated via the present invention. Any number of media computers, with each being dedicated to providing any number, types, or kinds of, news information, current events information, healthcare information, healthcare or healthcare-related news, current events, advertisements, and/or marketing information or materials, can be utilized in connection with the present invention.

Each of the central processing computer(s), the provider communications devices, the payer communication devices, the user or patient communication devices, the intermediary communication devices, the healthcare records computers, the insurance exchange computers, the social networking computers, and the media computers can communication in a bi-directional manner with, and/or can send and/or receive signals, messages, reports, notification messages, alerts, or any other communications or electronic communication transmissions, to, from and/or between, any other, or any number of, other central processing computer(s), if utilized, provider communications devices, payer communication devices, user or patient communication devices, intermediary communication devices, healthcare records computers, insurance exchange computers, social networking computers, and/or the media computers.

Each of the central processing computer(s), the provider communications devices, the payer communication devices, the user or patient communication devices, the intermediary communication devices, the healthcare records computers, the insurance exchange computers, the social networking computers, and the media computers can be linked to or with any other central processing computer(s), if utilized, provider communications devices, payer communication devices, user or patient communication devices, intermediary communication devices, healthcare records computers, insurance exchange computers, social networking computers, and/or the media computers via a wired link or line or a wireless link.

Each of the provider communications devices, payer communication devices, user or patient communication devices, intermediary communication devices, healthcare records computers, insurance exchange computers, social networking computers, and/or the media computers can be connected with or linked with the central processing computer.

Any and/or all of the signals, messages, reports, notification messages, or any other communications, described herein as being transmitted from one device, computer, or communication device, to another, can be, or can be included in, or be attached to, an e-mail message, an instant messaging message, an electronic transmission, or an electronic data transmission or electronic data interchange, or can be transmitted via any other data or information transmission, and can be transmitted via or using any appropriate or necessary computer(s) or device(s).

The present invention can be utilized on, and/or over, the Internet and/or the World Wide Web and/or any other communication network, telecommunication network, telephone network, a line-connected network, or a wireless communication network, or any combination of same. The present invention can also utilize wireless Internet and/or World Wide Web services, equipment and/or devices. The central processing computer(s) and/or any of the herein-described computers or communication devices can have a web site or web sites associated with same.

The present invention can be utilized on, or over, the Internet and/or the World Wide Web and/or on, or over, any other communication network or system, including, but not limited to, a communication network or system, a telecommunication network or system, a telephone communication network or system, a cellular communication network or system, a wireless communication network or system, a wireless Internet network or system, a wireless World Wide Web network or system, a line or wired communication network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, and/or any other communication network or system, and/or any combination of the above communication networks or systems.

The apparatus and method of the present invention can utilize electronic commerce technologies and security methods, techniques and technologies, in any and/or all of the instances of data and/or information processing, and/or data and/or information transmission described herein.

Each of the central processing computer(s), as well as each of the herein-described computers or communication devices can include a central processing unit or CPU, a random access memory device(s) (RAM), a read only memory device(s), and a user input device. Each of the central processing computer(s), as well as each of the herein-described computers or communication devices can also include a display device, a transmitter(s), a receiver, a database(s), and an output device. The database(s) can contain any and/or all of the data and or information which is needed to perform the various processing methods, services, functions and/or operations, described herein.

The present invention can be utilized in numerous preferred embodiments in order to provide a vast array of healthcare and healthcare-related services for any one or more of the various parties described herein.

The present invention can be utilized to create and maintain a comprehensive and/or a centralized electronic healthcare record system. The present invention can also be utilized to provide for a comprehensive electronic healthcare record, file, or history, for each individual, patient, or caregiver, as well as facilitates access to comprehensive healthcare or healthcare-related data and/or information for or regarding an individual, patient, or caregiver via the central processing computer. An individual's, patient's, or caregiver's, electronic healthcare record, electronic healthcare file or electronic healthcare history, can be contained in any number of electronic healthcare records, electronic medical records, electronic dental records, electronic pharmacy records, and/or electronic behavioral healthcare records, regardless of where each respective record is or may be stored.

A user can access any one or more, or any and/or all of, the electronic healthcare records, electronic medical records, electronic dental records, electronic pharmacy records, and/or electronic behavioral healthcare records, or portion(s) of same which contain data or information for or regarding individual, patient, or caregiver. The present invention can be utilized to provide a comprehensive healthcare record, file, or history, for an individual, patient, or caregiver, by providing any and/or all healthcare or healthcare-related data and/or information, for or regarding an individual, patient, or caregiver, and/or any and/or all link(s) or hyperlink(s) to any and/or all of the electronic healthcare records, electronic medical records, electronic dental records, electronic pharmacy records, and/or electronic behavioral healthcare records, which contain any and/or all healthcare or healthcare-related data or information for or regarding individual, patient, or caregiver.

The present invention can also be utilized by any individual, patient, caregiver, user, provider, insurer or payer, or third party or intermediary, to create a link or hyperlink to any electronic healthcare record(s), electronic medical record(s), electronic dental record(s), electronic pharmacy record(s), and/or electronic behavioral healthcare record(s), which contain or which are to contain healthcare or healthcare-related data or information for or regarding any individual, patient, or caregiver.

The present invention can also be utilized in order to allow an individual or a patient, or a caregiver, or one responsible for the care of an individual or patient, to enter notes, comments, or messages regarding or relating to the individual or patient into one or more of any of the individual's, patient's, or caregiver's, electronic healthcare record(s), electronic healthcare file(s), electronic medical record(s), electronic dental record(s), electronic pharmacy record(s), and/or electronic behavioral healthcare record(s). Any respective note, comment, or message can be in text form, audio form, or video form, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or an insurer or payer.

A healthcare provider can access, obtain, and/or use, the information provided or contained in the note, comment, or message, or provided or contained in multiple notes, comments, or messages, for any suitable purpose, such as, but not limited to, for preparing for, or for use during, a remote or virtual office visit with, or a remote or distance examination of, an individual, a patient, or a caregiver for or an individual or a patient, during a video telephone call, a video chat session, or a videoconference, with the individual, the patient, or the caregiver for or the individual or the patient, or for use during a conversation, discussion, or consultation, during a video telephone call, a video chat session, or a videoconference, with the individual, the patient, or the caregiver for the individual or the patient, or for use during a conversation, discussion, or consultation, during a video telephone call, a video chat session, or a videoconference, with and between, the healthcare provider, and the individual, the patient, or the caregiver for or the individual or the patient, or another healthcare provider or any other provider, or an insurer or a payer, or an intermediary, or for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

Any notes, comments or messages, can be provided by the individual, patient, or caregiver, or by any person caring for the individual or patient, while making an appointment, in advance of a video telephone call, a video chat session, or a videoconference, or a remote or virtual office visit with, or a remote or distance examination of, or in advance of a video telephone call, a video chat session, or a videoconference, or a remote or distance examination of, with the individual, the patient, or the caregiver for the individual or the patient, or a video telephone call, a video chat session, or a videoconference, with another provider, or a payer or insurer or any third party or intermediary, in connection with any tele-health related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s). In this regard, the present invention can allow an individual or patient, or a caregiver, or one responsible for caring for the individual or patient, to make and enter any notes, comments, or messages, into the individual's or patient's respective electronic healthcare record(s), electronic medical record(s), electronic dental record(s), electronic pharmacy record(s), and/or electronic behavioral healthcare record(s) so as to facilitate accurate and complete healthcare information record keeping.

Any provider of an individual or patient, any insurer or payer of an individual or patient, any caregiver of an individual or patient, or any other authorized third party, intermediary, person, or entity, can also enter and store any note(s), comment(s), or message(s) in the individual's or patient's electronic healthcare record.

Any insurance claim form or the payment request form can be date stamped and/or time stamped. In this manner, claim or payment request processing can be tracked or monitored so as to facilitate audits of the insurer or payer in order to ascertain if the insurer or payer is properly and/or efficiently handling a claim or payment request for the individual or patient, and/or if the insurer or payer is in compliance with any laws, rules, or regulations, governing claims or payment processing and/or handling. Information regarding the date stamped and/or time stamped claims, including the insurer's or the payer's processing or handling of same, and the response or reply to same, can also be stored by the present invention and can be accessed and/or obtained by any authorized user or entity.

The present invention can also generate a co-payment message or a deductible message containing information regarding a co-payment due by the individual or patient to the provider under the individual's or patient's insurance policy or payment program or a deductible which has to be met by the individual or patient under the individual's or patient's insurance policy or payment program.

The present invention can also be utilized in connection with or in conjunction with a personal healthcare record which an individual or patient can maintain for himself, herself, and/or for any children, parents, relatives, friends, or any other individuals whom the individual or patient may be providing care for as a caregiver or a person assisting a caregiver for another. In a preferred embodiment, the personal healthcare record can be stored on one or more user or patient communication devices which can include, but which are not limited to a personal computer, a laptop computer, a tablet, a cellular telephone, a wireless telephone, a television, a digital television, a personal digital assistant (PDA), a smart phone, a watch, or any other of the herein-described devices, or other devices, which can be used as a user or patient communication device. The personal healthcare record can be stored in any number of user communication devices.

An individual or patient can utilize the present invention to enter notes, comments, messages, information regarding how they are feeling, information regarding a sickness, an illness, a symptom, information regarding types of medications they must take and time intervals for taking same, information regarding their diet, foods eaten, drinks ingested, exercise activity, provider information, allergies, and/or any other healthcare information, healthcare-related information, wellness information, fitness information, diet information, exercise of fitness information, nutritional information, and/or any other information which can find application in a healthcare or healthcare-related setting or scenario or any other information pertinent to the individual or patient as well as any individual(s) for whom the individual or patient is serving as a caregiver.

An individual or patient can utilize the present invention, at any time and with any suitable user or patient communication device, enter or input, and store in a personal healthcare record, any relevant healthcare information, healthcare-related information, wellness information, fitness information, diet information, exercise of fitness information, nutritional information, and/or any other information which can find application in a healthcare or healthcare-related setting or scenario. The patient communication device can also be programmed to provide timed alerts or messages to remind the individual or patient to take medication, eat certain foods, intake certain liquids, schedule an appointment with a provider, check the status of an insurance claim or a payment claim, to exercise, provide diet or exercise reminders, or to perform any other action or activity for himself or herself or to perform any of the above for a person whom he or she is a caregiver.

The individual or patient can, at any time and from any location, access the present invention and upload or transmit to the central processing computer any and/or all information in his or her personal healthcare record into relevant portions of his or her electronic healthcare record and/or into a portion of same dedicated to receiving and storing the personal healthcare record information. The individual or patient can also download or receive from the central processing computer, any data and/or information that is stored in the individual's or patient's electronic healthcare record(s).

The user or patient communication device can also automatically receive, store or record in the personal healthcare record, and transmit to the central processing computer, and data and/or information which can be obtain with or from a wearable sensor or implantable sensor or device such as a wearable or implantable heart rate monitor, blood pressure monitor, blood sugar monitor, or any other device or monitor which can monitor a physiological parameter(s) or a biometric parameter(s). The user or patient communication device can be linked via a wireless or Bluetooth or other suitable communication link with one or more of these wearable or implantable sensors. Data and/or information obtained from the wearable or implantable sensors can be transmitted to the central processing computer and stored in the individual's or patient's electronic healthcare record(s).

The user or patient communication device and/or the personal health record utilized in connection with same, can be equipped with hardware and/or software for translating any data and/or information from one language into any other language, for translating audio information into text information for storing in the user or patient communication device, for storing audio information, for translating text information into audio information, for providing reminders to schedule appointments with providers, for providing reminders for scheduled appointments with providers, and/or for providing any other functions which are described herein as being performed in connection with the user or patient communication device. The present invention can also be utilized to receive information from an individual or patient regarding a personal healthcare record, store and update an electronic healthcare record with the personal healthcare record information, and thereafter, generate a new personal healthcare record using any new or updated information from the electronic healthcare record(s). The present invention can provide and maintain up-to-date electronic healthcare records and personal healthcare records for individuals or patients.

The user or patient communication device of the present invention can also be utilized to be a personal healthcare monitoring and/or planning tool or device for monitoring and/or planning healthcare and/or healthcare-related activities, events, occurrences, and/or happenings, for the individual or patient, the individual's or patient's children, parents, relatives, or those for whom the individual or patient serves or acts as a caregiver. The user or patient communication device can also be utilized to be a personal wellness, fitness, and/or nutritional monitoring and/or planning tool or device for monitoring and/or planning wellness or wellness-related, fitness or fitness-related, and/or nutritional or nutritional-related, activities, events, occurrences, and/or happenings, for the individual or patient, the individual's or patient's children, parents, relatives, or those for whom the individual or patient serves or acts as a caregiver. The user or patient communication device can also be equipped with any needed or desired software or software application or any number of software applications needed, required, or desired for enabling the user or patient communication device to provide the herein-described features, functions, and/or functionality. The present invention can also be utilized to provide information regarding individual and/or family healthcare planning, and/or monitoring, individual and/or family wellness planning and/or monitoring, individual and/or family fitness planning and/or monitoring, and/or individual and/or family nutritional planning and/or monitoring.

The present invention can also be utilized to schedule appointments, and/or remote or virtual office visits or examinations, with providers and to provide automatically generated appointment reminders.

The present invention can also be utilized to provide social networking functionality and capability via an electronic healthcare record(s) or any. Any of the herein-described individuals, patients, caregivers, providers, insurers, payers, third parties, or other entities, can access a social network via any of the electronic healthcare records described herein. Each and every type or kind of electronic healthcare record utilized in or in connection with the present invention can have information, link(s), or hyperlink(s), to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The present invention can also be utilized to provide an individual or patient with information, or a link(s) or a hyperlink(s) to information, regarding a social networking website or a social networking company, any information provided thereby or thereat, or information regarding any social networking support groups or social networking support group members, on-line seminars, forums, chat room discussions, or others, with which or whom the individual or patient may engage upon the individual or patient being diagnosed with an illness, a sickness, or a condition, or upon the individual or patient about to undergo or undergoing a treatment, a procedure, or an operation, or about to embark upon or already involved in a treatment plan.

The providing of the social networking information to the individual or patient can also serve to allow the individual or patient to learn more about a diagnosis, a treatment, or a treatment plan, to interact with others who have been diagnosed with the same or a similar illness, a sickness, or a condition, or others who may be undergoing the same or a similar treatment or who may be following a same or a similar treatment plan. The present invention can also be utilized so as to identify and provide the individual or patient with information or link(s) or hyperlink(s) to a social networking website, a social networking company, a support group or support groups, a member of the social network members of the social network, social networking lectures, classes, or seminars, social networking sponsored lectures, classes, or seminars, social networking discussions, question and answer sessions, or informational or other forums, or any other social networking or social networking sponsored activities or events, for any number of social networks. The present invention can also be utilized in a same, similar, or analogous manner, in order to process and/or to provide veterinary healthcare information and/or veterinary healthcare-related information for and regarding any kind or type of animal or animals or any type or kind of pet or pets. The present invention can also be utilized as a clearinghouse for facilitating the offering, selling, buying, trading, and/or other commerce and/or transactions, involving healthcare and/or healthcare-related services, products and/or goods.

The present invention can be utilized to allow an individual, a patient, or a caregiver of or for the individual or the patient to engage in a video call, a video chat session, or a videoconference, with a healthcare provider in order to facilitate or to provide for a remote or virtual office visit with the healthcare provider or in order to facilitate or to provided for a remote or distance consultation or examination with or by a healthcare provider.

Any number, kinds, or types, of healthcare providers, who or which have registered with the apparatus of the present invention in order to engage in video calls, video chat sessions, or videoconferences, in order to provide remote or virtual office visits or in order to provide remote or distance consultations or examinations with and for any individuals or patients, or caregivers, can store any data and/or information regarding his, or her name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

Any of the above-described or herein-described data and/or information regarding the healthcare provider, for any number of healthcare providers, can be stored in, and can be searchable from, the database of the central processing computer. Any of the above-described or herein-described data and/or information regarding the healthcare provider, for any number of healthcare providers, can be also be stored in, and can be searchable from, the database of any provider communication device. Further, any of the above-described or herein-described data and/or information regarding the healthcare provider, for any number of healthcare providers, can be also be stored in, and can be searchable from, the database of any user communication device.

The individual, the patient, or the caregiver of or for the individual or the patient, can access the central processing computer or a respective provider communication device with or using his or her user communication device, or by accessing data and/or information stored in his or her communication device, at any time, in order to search for and/or to select a healthcare provider(s) with whom he or she can schedule a video call, a video chat session, or a videoconference. The individual, the patient, or the caregiver of or for the individual or the patient, can select the individual's or the patient's current healthcare provider, current primary care provider, or a new or different healthcare provider, or a healthcare provider having a certain specialization, or a certain availability. The individual or the patient, or the caregiver of or for the individual or the patient, can make an appointment for a video call, a video chat session, or a videoconference, with the healthcare provider with or using the user communication device. At the time of making the appointment the individual, patient, or caregiver, can provide a telephone number, a call number, a conference call number, or an IP address, associated with the user communication device which the individual, the patient, or the caregiver, will use for the video call, the video chat session, or the videoconference. At the time of making the appointment, the individual, the patient, or the caregiver, can also be provided with the telephone number, the call number, the conference call number, or the IP address, associated with the provider communication device which will be used by the healthcare provider for the video call, the video chat session, or the videoconference. At the time of making the appointment, the individual, the patient, or the caregiver, can also be provided with an instruction as to whether he or she is to call the healthcare provider at the appointment time, or whether the healthcare provider will call the individual, the patient, or the caregiver, at the appointment time.

In instances when the appointment is being made via the central processing computer, the appointment can be made via the individual's or the patient's electronic medical record, file, or history, which is stored in the database of the central processing computer, and information regarding the appointment can be stored in the individual's or the patient's electronic medical record, file, or history as well as in the healthcare provider's work schedule or in an appointment schedule of the healthcare provider. In instances when the appointment is being made via a provider communication device, the appointment can be made via the individual's or the patient's electronic medical record, file, or history, which is stored in the database of the provider communication device, and information regarding the appointment can be stored in the individual's or the patient's electronic medical record, file, or history as well as in the healthcare provider's work schedule or in an appointment schedule of the healthcare provider. In instances when the appointment is being made via a user communication device, the appointment can be made via the individual's or the patient's electronic medical record, file, or history, or personal healthcare record, which is stored in the database of the user communication device, and information regarding same can be automatically transmitted to and stored in the individual's or the patient's electronic medical record, file, or history in the database of the central processing computer as well as in the healthcare provider's work schedule or in an appointment schedule of the healthcare provider.

The central processing computer can be programmed so that, once an appointment for a video call, a video chat session, or a videoconference, has been made, the central processing computer can automatically generate an appointment message containing information regarding the appointment, and/or the time and date of same, which has been scheduled and will transmit same to the provider communication device of or associated with the healthcare provider with whom the appointment has been made, and will also transmit same to the user communication device(s) of or associated with the individual, the patient, or the caregiver. The provider communication device with which an appointment has been made can also be programmed so that, once an appointment for a video call, a video chat session, or a videoconference, has been made, the provider communication device can automatically generate an appointment message containing information regarding the appointment, and/or the time and date of same, which has been scheduled and will transmit same to any other provider communication device of or associated with the healthcare provider with whom the appointment has been made, and will also transmit same to the user communication device(s) of or associated with the individual, the patient, or the caregiver. The user communication device with which an appointment has been made can also be programmed so that, once an appointment for a video call, a video chat session, or a videoconference, has been made, the user communication device can automatically generate an appointment message containing information regarding the appointment, and/or the time and date of same, which has been scheduled and will transmit same to the central processing computer, to any provider communication device of or associated with the healthcare provider with whom the appointment has been made, and/or to any other user communication device(s) of or associated with the individual, the patient, or the caregiver.

The central processing computer can also be programmed so that, once an appointment for a video call, a video chat session, or a videoconference, has been made, the central processing computer can automatically generate a reminder message(s) containing information for reminding each of the individual, the patient, or the caregiver, and the healthcare provider of the appointment for the video call, the video chat session, or the videoconference. The reminder message or reminder messages can be transmitted to each of the user communication device(s) of or associated with the individual, the patient, or the caregiver, and to the provider communication device of or associated with the healthcare provider.

Any of the appointment messages and/or reminder messages described herein can include the appointment time, the name of the healthcare provider, and the telephone number, the call number, the conference call number, or the IP address, associated with the provider communication device which will be used by the healthcare provider for the video call, the video chat session, or the videoconference, and the name of the individual, the patient, or the caregiver, and the telephone number, the call number, the conference call number, or the IP address, associated with the user communication device which the individual, the patient, or the caregiver, will use for the video call, the video chat session, or the videoconference, and an instruction, if any, as to who is to initiate the video call, the video chat session, or the videoconference, such as, for example, whether the individual, the patient, or the caregiver, is to call the healthcare provider at the appointment time or whether the healthcare provider is to call the individual, the patient, or the caregiver, at the appointment time.

Any of the herein-described appointment messages and/or reminder messages can be stored in the individual's or the patient's electronic healthcare record, file, or history, in the database of the central processing computer and/or in the database of the user communication device, such as in a healthcare provider appointments section or field of same. Likewise, any of the herein-described appointment messages and/or reminder messages can be stored in the healthcare provider's records or files which can also be stored in the database of the central processing computer and/or in the database of the provider communication device such as in an appointments section or field of same.

Any of the herein-described appointment messages or reminder messages can also contain a link or a hyperlink to the electronic healthcare record, file, or history, of the individual or the patient. Any of the herein-described appointment messages or reminder messages can also contain a link or a hyperlink for allowing each of the individual, the patient, or the caregiver of or for the individual or the patient to initiate a video call, a video chat session, or a videoconference, described herein via the link or the hyperlink.

A healthcare provider or any number of healthcare providers can be available for a video call, a video chat session, or a videoconference, at any given time and an individual, a patient, or a caregiver for the individual or the patient, can simply access the central processing computer, see which healthcare provider or healthcare providers are available and can immediately initiate a video call, a video chat session, or a videoconference, with an available healthcare provider.

The apparatus of the present invention can be utilized to in order to the healthcare provider to gain authorized access to the individual's or the patient's electronic healthcare records, files, or history, prior to and/or during the video call, the video chat session, or the videoconference, with the individual, the patient, or the caregiver of or for the individual or the patient. In this regard, the healthcare provider can review the individual's or the patient's electronic healthcare records, files, or history, prior to and/or during the video call, the video chat session, or the videoconference, obtain information from same, enter notes, observations, or examination findings, into same, and/or enter information regarding a diagnosis, a treatment, or a treatment plan into same, and/or enter information regarding and/or prescribe a medication or a drug, prescribed a therapy or any kind or type, prescribed a treatment of any kind or kind, and/or make a referral to another healthcare provider. Any and/or all information, including a video or a video clip, and/or an audio, a video, and/or an audio and video recording, of the video call, the video chat session, or the videoconference, can be recorded and stored in the individual's or the patient's electronic healthcare records, files, or history.

The present invention can be utilized in order to allow a healthcare provider to conduct a video call, a video chat session, or a videoconference with an individual, a patient, or a caregiver of the individual or the patient, in order to allow the healthcare provider to conduct a remote or virtual office visit with, or to conduct a remote or distance examination of, the individual or the patient. The healthcare provider can obtain any information, needed or desired for conducting the remote or virtual office visit or the remote or distance examination, from the individual, the patient, or the caregiver, during the video call, the video chat session, or the videoconference. The healthcare provider can also access and/or obtain information from the individual's or the patient's electronic healthcare record, file, or history. The healthcare provider can also obtain information from any healthcare measuring device or equipment, any healthcare measurement device or equipment, or any healthcare monitoring device or equipment, or obtain and/or transmit any data and/or information from any healthcare equipment input device, healthcare measurement input device, or healthcare monitoring input device described herein. The healthcare provider can enter any notes and/or observations regarding the individual or the patient and/or regarding any data and/or information obtained or reviewed during the video call, the video chat session, or the videoconference, into the individual's or the patient's electronic healthcare record, file, or history.

The healthcare provider can also make or arrive at a diagnosis for the individual or the patient, and/or prescribe a treatment, or a course of treatment, or provide a treatment plan, or generate or issue a prescription for a drug or a medication, or generate or issue a prescription for a test or procedure, or make a referral to another healthcare provider, for the individual or the patient. The healthcare provider can utilize any information contained in the individual's or the patient's electronic healthcare record, file, or history, in order to take into account any allergies, possible drug or medication interactions, or any other information regarding the individual or the patient which must be considered in making a diagnosis, and/or in prescribing a treatment, or a course of treatment, or in providing a treatment plan, or in generating or issuing a prescription for a drug or a medication, or in generating or issuing a prescription for a test or a procedure, or in making a referral to another healthcare provider, for the individual or the patient. Any prescription(s) or referral(s) generated or issued can be electronically sent, such as by e-mail, instant message, SMS message, MMS message, or in any other suitable communication device to any provider communication device of or associated with the individual's or the patient's pharmacy or to any other healthcare provider to whom the respective prescription or referral is to be sent.

The healthcare provider can also enter any information regarding any notes, observations, examination findings, and/or any other information obtained during the video call, the video chat session, or the videoconference, into the individual's or the patient's electronic healthcare record, file, or history, so as to update same to include information regarding the video call, the video chat session, or the videoconference, and the remote office visit or the virtual office visit and/or the remote examination or the distance examination which was conducted during same with the individual, the patient, or the caregiver.

The video call, which can be recorded, can also be stored in the individual's or the patient's electronic healthcare record, file, or history, for retrieval at any time by the healthcare provider or another healthcare provider, or by the individual, the patient, the caregiver, or another caregiver, or by a healthcare insurer or a healthcare payer, or by an intermediary, or by any other authorized person or entity, at any time.

The apparatus or the central processing computer can, after any and/or information obtained during and/or regarding the video call has been entered by the healthcare provider and stored in the individual's or the patient's electronic healthcare record, file, or history, can generate a video call report and/or a remote or virtual office visit report or a remote or distance examination report, containing information regarding the video call and/or information regarding the video call and/or the remote or virtual office visit or the remote of distance examination, and can transmit the video call report and/or remote or virtual office visit report or a remote or distance examination report in, as, or attached to, an e-mail message or in, as, or attached to, an electronic communication transmission, to the provider communication device of or associated with the individual's or the patient's primary care healthcare provider or any other healthcare provider of the individual or the patient, to a user communication device of or associated with the individual, the patient, or a caregiver of the individual or the patient, to a payer communication device of or associated with a healthcare insurer or a healthcare payer of the individual or the patient, and/or to an intermediary communication device of or associated with an intermediary. Any remote or virtual office visit report or a remote or distance examination report generated by the apparatus of the present invention can also be stored in the individual's or the patient's electronic healthcare record, file, or history.

The apparatus or the central processing computer, which can be programmed to generate and transmit an insurance claim form or a request for payment form, can utilize the information stored by the healthcare provider in order to generate an insurance claim form or a request for payment form. The apparatus or the central processing computer, which can be programmed to generate and transmit a request for payment of co-payment form, can generate a request for payment of co-payment form. The apparatus or the central processing computer can transmit the insurance claim form or a request for payment form, in, as, or attached to, an e-mail message, or in, as, or attached to any other suitable electronic communication transmission, to the payer communication device of or associated with the healthcare insurer or the healthcare payer of the individual or the patient. The apparatus or the central processing computer can also transmit the request for payment of co-payment form in, as, or attached to, an e-mail message, or in, as, or attached to any other suitable electronic communication transmission, to the user communication device.

Any insurance claim form(s) or a request for payment form(s) and any request for payment of co-payment form(s) generated by, and/or transmitted by, the apparatus or the central processing computer can be stored in the individual's or the patient's electronic healthcare record, file, or history.

In this regard, the apparatus and method of the present invention can be utilized to facilitate and/or to conduct remote or virtual healthcare provider visits, consultations, and/or examinations, via and/or through the use of video calls, video chat sessions, and/or videoconferences, with and between an individual, a patient, and/or a caregiver for the individual or the patient. The apparatus and method of the present invention can also be utilized to schedule remote or virtual provider visits, consultations, and/or examinations, via and/or through the use of video calls, video chat sessions, and/or videoconferences, with and between an individual, a patient, and/or a caregiver for the individual or the patient.

The present invention can also be utilized in connection with, or in conjunction with, a distributed ledger and with Blockchain technology. A distributed ledger and Blockchain technology can be utilized along with a central processing computer, in a combined system, wherein certain of the transactions, described herein as being performed by the apparatus, can be processed and/or performed by and/or with a central processing computer and/or certain other transactions can be processed and/or performed by and/or with, and/or using, a distributed ledger and Blockchain technology or Blockchain technologies. Any and/or all transactions, described herein as being performed and/or processed by the apparatus, can also be processed and/or performed by and/or with, and/or using, a distributed ledger and Blockchain technology or Blockchain technologies, and/or using any cryptocurrency Blockchain technology or technologies.

Any type of Blockchain technology can be utilized in connection with the apparatus and methods of the present invention. For example, the apparatus and methods of the present invention can utilize a distributed ledger(s) along with any Blockchain technology or technologies, Bitcoin Blockchain technology or technologies, Ethereum Blockchain technology or technologies, Bitcoin Cash Blockchain technology or technologies, Litecoin Blockchain technology or technologies, Privacy Coin Bitcoin technology or technologies, and/or any other suitable Blockchain technology or technologies, and/or Smart contracts and/or Smart contract technology or technologies and/or decentralized autonomous organizations (DAOs), decentralized autonomous organizations (DAOs) technology or technologies, and/or any combination of same.

Applicant incorporates by reference herein the subject matter and teachings of "Blockchain Technology Explained" by Alan T. Norman, "Blockchain" by Abraham K. White, "Blockchain—A Practical Guide To Developing Business, Law, And Technology Solutions" by Joseph J. Bambara and Paul R. Allen, and "Blockchain—Ultimate Guide To Understanding Blockchain, Bitcoin, Cryptocurrencies, Smart Contracts And The Future of Money" by Mark Gates, in their entirety, for all of their respective subject matter and teachings regarding distributed ledger technology and/or technologies, Blockchain technology and/or technologies, Bitcoin technology and/or technologies, Bitcoin Blockchain technology and/or technologies, Ethereum technology and/or technologies, Ethereum Blockchain technology and/or technologies, cryptocurrencies, cryptocurrency technology and/or technologies, and/or smart contract technology and/or technologies, and/or decentralized autonomous organizations (DAOs) technologies, and/or peer-to-peer technology and/or technologies, and/or any other technology or technologies related thereto or which can be utilized in conjunction distributed ledgers, Blockchain technologies, Smart contracts, decentralized autonomous organizations (DAOs), and/or cryptocurrencies.

By utilizing a distributed ledger and a suitable Blockchain technology, the apparatus and methods of the present invention can reduce the amount of processing performed by, and reliance on, a central processing computer and/or can eliminate the need for a central processing computer and any centralized entity which might operate the central processing computer.

A central processing computer and distributed ledger and Blockchain technology system can be utilized which includes a central processing computer component, which can perform any and/or all of the functions described herein as being performed by the central processing computer, and a distributed ledger and Blockchain technology system component, which can also perform any and/or all of the functions described herein as being performed by the central processing computer.

Any and/or all of the various operations, transactions, functions, and/or functionalities, described herein as being performed by the apparatus can be performed by either a central processing computer component of the central processing computer/distributed ledger/Blockchain technology system and/or by the distributed ledger and Blockchain technology system component of the central processing computer/distributed ledger/Blockchain technology system.

Transactions which are to be processed by the central processing computer component and by the distributed ledger and Blockchain technology system component can be pre-selected or pre-programmed into the central processing computer/distributed ledger/Blockchain technology system, and can be re-programmed at any time. The use of the distributed ledger and Blockchain technology system component can be utilized to provide added security for the individual's or the patient's electronic healthcare record, file, or history, and can also be utilized to prevent healthcare identity theft involving the individual or patient.

The apparatus and method of the present invention can also be utilized to facilitate and/or to conduct remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary. The apparatus and method of the present invention can also be utilized to schedule remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The apparatus and method of the present invention can also be utilized to facilitate healthcare claims processing. Any of the individuals, patients, caregivers, providers, insurers or payers, and/or intermediaries or third parties, or any other users, can file claims with the respective insurer, payer, or party, electronically via the apparatus of the present invention. The apparatus of the present invention can facilitate an expedited and/or a paperless claim process or request for payment process. The apparatus of the present invention can also provide for, or facilitate, automatic claim submission or request for payment submission to an insurer or payer.

The apparatus of the present invention can also be utilized in order to claim or request healthcare insurance benefits, disability insurance benefits, and/or life insurance benefits. The apparatus can also administer and/or maintain financial accounts for, and/or on behalf of, any of the individuals, patients, caregivers, users, providers, insures or payers, and/or intermediaries or third parties, described herein.

The present invention can, in addition, be utilized in order to maintain individual, patient, or caregiver, electronic healthcare records or electronic healthcare files private and/or to safeguard individual, patient, or caregiver, electronic healthcare records or electronic healthcare files, by restricting and/or by limiting access to the respective electronic healthcare records or electronic healthcare files.

The present invention can also be utilized to issue prescriptions or scripts for medicines, medications, or drugs, to pharmacies on an individual's or a patient's behalf, or to issue prescriptions or scripts for procedures, tests, analyses, analysis work-ups, blood work, treatments, therapy, therapy sessions, physical therapy, physical therapy sessions, or any other prescribed goods, services, or activities, or to issue referrals to other healthcare providers or providers of any other goods or services. The apparatus of the present invention can also be utilized to perform drug-drug and drug-allergy interaction checks.

The apparatus and method of the present invention can also be used to provide for the remote control and/or monitoring of any of the herein-described healthcare devices, healthcare equipment, healthcare testing devices or equipment, healthcare information gathering devices or equipment, or healthcare monitoring devices or equipment. The apparatus and method of the present invention can also be utilized in order to perform a remote procedure on an individual or patient, a remote surgery or surgical procedure on an individual or patient, or to remotely administer a treatment to an individual or patient.

Intelligent agents, software agents, mobile agents, and/or related technologies, can be utilized in conjunction with the present invention. The respective intelligent agent(s), software agent(s), mobile agent(s), (hereinafter referred to collectively as "intelligent agent" or "intelligent agents") can be programmed and/or designed to act on behalf of the respective users, individuals, patients, caregivers, providers, insurers or payers, and/or intermediaries, so as to act on behalf of the respective party as well as to perform any of processing functions and/or other functions described herein.

In another preferred embodiment, the intelligent agent can act on behalf of the respective person or party in various related interactions and/or other activities which are described as being performed herein and/or which may be incidental and/or related thereto. Therefore, the present invention also provides an agent-based apparatus and method for providing healthcare information and/or healthcare-related information.

The apparatus of the present invention, in any and/or all of the embodiments described herein, can also be programmed to be self-activating and/or activated automatically.

In any and/or all of the embodiments described herein, the apparatus of the present invention can also be utilized in a same, similar, or analogous manner, in order to process and/or to provide veterinary healthcare information and/or veterinary healthcare-related information for and regarding any kind or type of animal or animals or any type or kind of pet or pets. In this regard, it is to be understood that the present invention can be utilized by any user, individual, caregiver, provider, insurer or payer, or intermediary, in order to process healthcare or healthcare-related information for any animals and/or pets.

The present invention can also provide for cloud-based healthcare or healthcare-related data and/or information processing and/or storage, cloud-based electronic healthcare records, cloud-based electronic healthcare records storage and/or retrieval, a cloud-based electronic healthcare records system or platform, and/or cloud based processing and/or storage of any and/or all of the data and/or information described herein as being processed by the apparatus and methods of the present invention.

Any data and/or information regarding any of the herein-described insurance claims, claims for payment, and/or any other request for a payment, for, regarding, or relating to, any video call, video chat session, or videoconference, can contain, or can contain as an attachment, a copy of a recording of the video call, the video chat session, or the videoconference.

Further, any data and/or information regarding any of the herein-described insurance claims, claims for payment, and/or any other request for a payment, for, regarding, or relating to, any video call, video chat session, or videoconference, can be stored in the electronic healthcare record of or for the individual or the patient using the distributed ledger and/or blockchain technology system.

DESCRIPTION OF THE PREFERRED EMBODIMENTS

Figure 1:
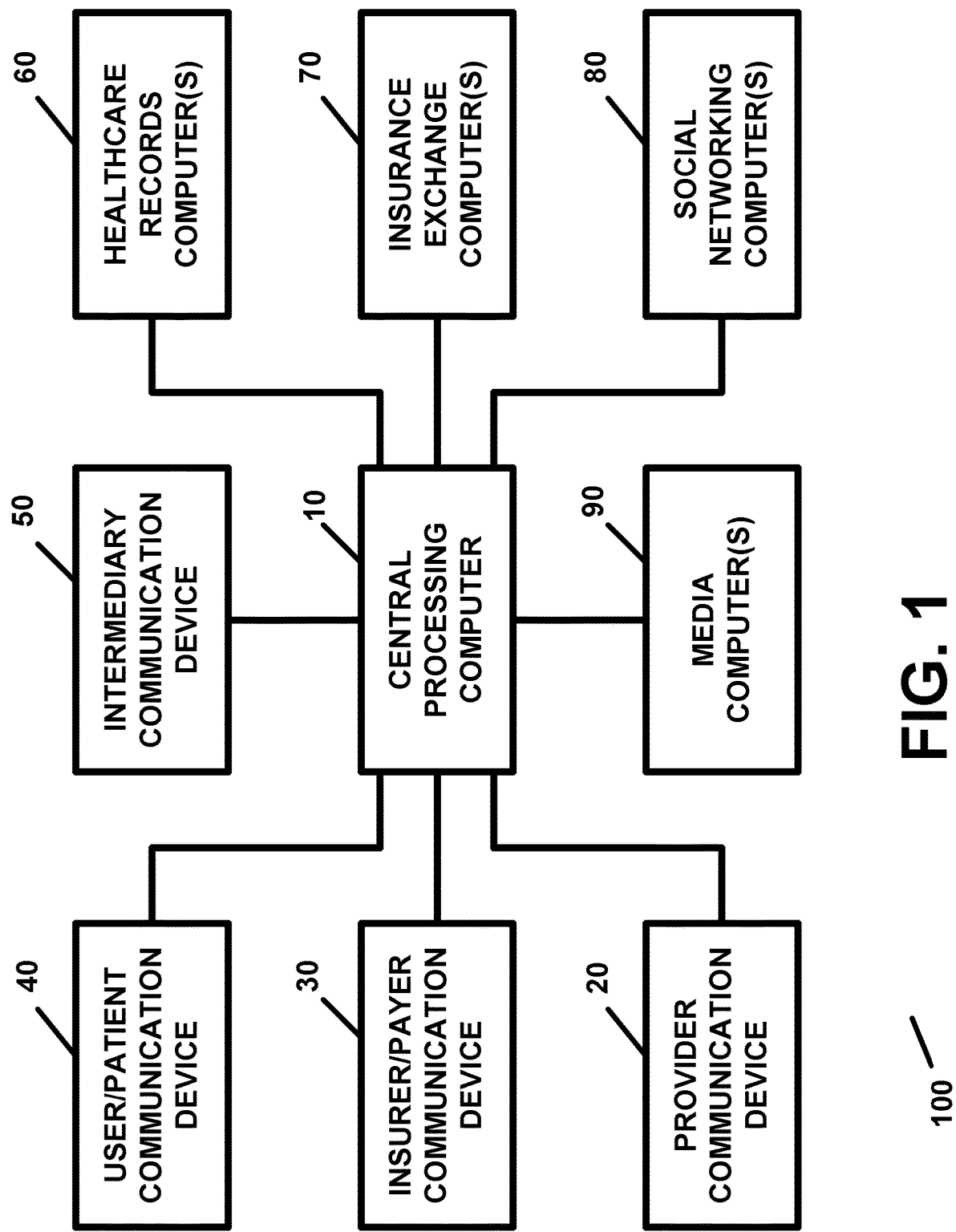
FIG. 1 illustrates a preferred embodiment of the apparatus of the present invention, in block diagram form.

The present invention pertains to an apparatus and a method for providing healthcare services remotely or virtually with or using an electronic healthcare record and/or a communication network and, in particular, to an apparatus and a method for providing healthcare services remotely or virtually with or using an electronic healthcare record and/or a communication network which can facilitate communications and data and/or information exchange with and/or between an individual or a patient and a healthcare provider or a healthcare professional.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus and method of the present invention can be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribed a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

As used herein, the term "electronic healthcare record" or "EHR" means any electronic healthcare record, electronic healthcare file, electronic medical record, electronic dental record, electronic pharmacy record, electronic behavioral health record, and/or any other record or record keeping system, software, hardware, or device, or any combination of same or group of same, which can contain healthcare information or healthcare-related information.

As used herein, the terms "individual", "patient", "client", "user" or the like, or their plural forms, refers to any person, individual, patient, entity, and/or client, who or which uses the present invention, and/or who seeks and/or who receives healthcare services, healthcare-related services, healthcare-related information, and/or any of the other services and/or products provided by the present invention. The terms "individual", "patient", "client", "user" or the like, or their plural forms, also refer to any athlete or participant of or in any sport or sports or any activity or activities, an athlete or a sports participant of any age, a professional athlete, a minor league athlete, an Olympic athlete, a competitive athlete, a government team athlete, a world class competition athlete, an amateur athlete, a college athlete, a high school age athlete, a child athlete, a secondary school athlete, a recreational organization athlete or member, a child recreational organization athlete or member, an adult recreational organization athlete or member, a little league athlete or member, a boys club athlete or member, a girls club athlete or member, a hobbyist athlete, or any other individual, male or female, who participate in athletic endeavors, sporting events, exercise activities, martial arts, mixed martial arts, boxing, wrestling, or physical activities, or any team sport or activity or individual sport or activity.

As used herein, the term "caregiver" or the plural of same, refers to any parent, child, agent, attorney, representative, guardian, legal guardian, or any other person or entity who or which is responsible for caring for, looking after, or otherwise taking care of any healthcare needs of any individual or patient. The term "caregiver" also refers to any organization, governmental entity, business, team, league, club, network, or any other entity, or any employee or agent of same, which or who oversees, manages, uses, employs, provides oversight over, owns or otherwise has playing or managing rights over, provides control over, or provides or is responsible for the healthcare of, any of the herein-described or other athletes or sports participants.

As used herein, the terms "doctor", "healthcare provider", "provider", "therapist", "healthcare information specialist", etc., or their plural forms, refers to any medical doctor, including any and all of the various medical specialists and/or specialties, including, but not limited to internists, orthopedists, opthamalogists, cardiologists, hematologists, endocrinologists, oncologists, ears, nose and throat specialists, neurologists, urologists, gastrointerologists, dermatologists, pediatricians), medical specialist, surgeon, surgical specialists, including any and/or forms and/or types of surgeons), physician, dentist, psychiatrist, psychologist, optometrist, podiatrist, osteopath, chiropractor, pharmacist, therapist, physical therapist, respiratory therapist, nurse, healthcare aid, nutritionist, and/or any other person, individual and/or professional who can provide healthcare, healthcare-relate, wellness and/or wellness-related services and/or products.

As used herein, the terms "insurer", "payer", "insurance provider", "heath insurance provider", "life insurance provider", "disability insurance provider", etc., or their plural forms, refers to any insurance companies, healthcare insurance companies, disability insurance companies, property or casualty insurance companies, health maintenance organizations, healthcare providers, and any other payer and/or provider of healthcare services and/or products, who which provide and/or pay for healthcare and/or healthcare-related benefits, services, and/or products, and/or who or which provide respective health insurance, life insurance and/or disability insurance benefits, services and/or products. The terms "insurer" or "payer" can also refer to any government or governmental agency, department, of entity, which provides healthcare services or which provides payment(s) for healthcare and/or healthcare services.

As used herein, the terms "broker", "agent", "billing service", "collection agent", "manager", "intermediary", "assistant", etc., or their plural forms, refer to any broker, insurance broker, agent, insurance agent, intermediary, third party, billing service provider, collection agent, claim processing agent, and/or any other person, individual, and/or entity, which acts on behalf of, or for, any of the individuals, patients, doctors, healthcare providers, insurers, payers, etc., described herein.

Applicant hereby incorporates by reference herein the subject matter and teachings of U.S. patent application Ser. No. 14/638,934, filed Mar. 4, 2015, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

Applicant hereby incorporates by reference herein the subject matter and teachings of U.S. Provisional Patent Application Ser. No. 61/971,225, filed Mar. 27, 2014, and entitled "APPARATUS AND METHOD FOR PROVIDING HEALTHCARE SERVICES REMOTELY OR VIRTUALLY WITH OR USING AN ELECTRONIC HEALTHCARE RECORD AND/OR A COMMUNICATION NETWORK", the subject matter and teachings of which are hereby incorporated by reference herein in their entirety.

FIG. 1 illustrates the apparatus of the present invention, in block diagram form. The apparatus of the present invention is denoted generally by the reference numeral 100. In the preferred embodiment, the apparatus 100 of the present invention includes a central processing computer or central processing computer system 10 (hereinafter referred to as the "central processing computer 10"). In the preferred embodiment the central processing computer 10 can be a network or server computer.

In the preferred embodiment, the central processing computer 10 can provide control over the apparatus 100 and can perform any of the various processing services and/or functions described herein. The central processing computer 10 may be a single computer or system of computers and/or may be include a plurality of computers or computer systems which are utilized in conjunction with one another. The central processing computer 10, in the preferred embodiment can provides services for any of the other computers and/or computer systems described herein as being associated with any of the individuals, patients, healthcare providers, insurers, payers, brokers, agents, and/or intermediaries, described herein.

The apparatus 100 also includes a healthcare provider communication device or computer 20 (hereinafter referred to as "provider communication device 20" or "provider computer 20") which is associated with a healthcare provider such as a healthcare professional, a hospital, a clinic, and/or any other provider of services described herein. A provider computer 20 can also be associated with, or can be used by, any research institution, research facility, teaching institution, teaching hospital, college, university, school, or other institution or entity which may perform research, or provide research information or any related information regarding studies, findings, or developments, in the healthcare field or in healthcare-related fields. A provider computer 20 can also be associated with, or can be used by, any public health department, public health agency, public health facility, or other public health entity, on any one or more of a national level, a country level, a state level, a provincial level, a county level, a city level, a municipal level, or any other level, which is entrusted to provide for the public health and/or to perform services or oversight regarding public health. A provider computer 20 can also be associated with, or can be used by, any immunization registry or immunization registries. A provider computer 20 can also be associated with, or can be used by, any source or provider of educational or instructional information, or information regarding instructions or procedures, or links or hyperlinks to same.

Any number or amount of healthcare provider computers 20 can be utilized in conjunction with a healthcare provider and/or group of providers. The healthcare provider communication device(s) 20 can communicate with, and operate in conjunction with, the central processing computer 10 and/or any of the other computers and/or computer systems associated with any of the other individuals and/or entities which utilize and/or operate in conjunction with the present invention.

The apparatus 100 can also include a healthcare insurer or payer communication device or computer 30 (hereinafter referred to as "payer communication device 30" or "payer computer 30") which is associated with a healthcare payer such as a healthcare insurer, insurance company, health maintenance organization, a clinic, and/or any other payer of healthcare services and products described herein. Any number or amount of healthcare payer computers 30 can be utilized in conjunction with a healthcare payer and/or group of payers. The healthcare payer communication device(s) 30 can communicate with, and operate in conjunction with, central processing computer 10 and/or any of the other computers and/or computer systems associated with any of the other individuals and/or entities which utilize and/or operate in conjunction with the present invention.

The apparatus 100 can also include a user, patient, or individual, communication device or computer 40 (which may hereinafter be referred to either as "user communication device 40", "user or patient communication device 40", "user computer 40", "patient computer 40", or "user or patient computer or communication device 40") which is associated with any user of the apparatus 100 or any individual or healthcare patient or client who seeks or who is provided with healthcare and/or related services, products and/or related information. The user or user or patient communication device 40 can also be utilized by any individual, party, or entity, who or which may merely utilize the present invention in order to care or another individual or to obtain information of interest.

A user or user or patient communication device 40 may also be located at public places or locations, such as at kiosks or other publicly available computer or communication devices. Any number or amount of user or patient computers 40 can be utilized in conjunction with a user, patient, group of users, and/or group of patients. The user or patient communication device 40 can communicate with, and operate in conjunction with, the central processing computer 10 and/or any of the other computers and/or computer systems associated with any of the other individuals and/or entities which utilize and/or operate in conjunction with the present invention. The user or patient communication device 40 can also be utilized by any other individual or entity desiring to utilize and/or to obtain information from the apparatus 100.

The apparatus 100 can also include an intermediary communication device or computer 50 (hereinafter referred to as "intermediary communication device 50" or "intermediary computer 50") which is associated with an intermediary, a broker, an agent, and/or any other individual and/or entity, that can utilize the present invention in order to act for and/or on behalf of any other individual, party, or entity, described herein. Any number or amount of intermediary computers 50 can be utilized in conjunction with an intermediary and/or group of intermediaries. The intermediary computer(s) 50 can communicate with, and operate in conjunction with, the central processing computer 10 and any of the other computers and/or computer systems associated with any of the other individuals and/or entities which utilize and/or operate in conjunction with the present invention.

In the preferred embodiment, any of the provider communication device(s) 20, the payer computer(s) 30, the patient computer(s) 40, and/or the intermediary computer(s) 50, can be any computer or communication device, including, but not limited to, a personal computer, a home computer, a server computer, a network computer, a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch.

Each of the central processing computer(s) 10, the provider communication device(s) 20, the payer communication device(s) 30, the patient computer(s) 40, and/or the intermediary computer(s) 50, can transmit information to, as well as receive information from, any of the computers 10, 20, 30, 40, and 50, described herein. In this regard, each of the computers 10, 20, 30, 40, and 50, can communicate with, process information from, and/or share data and/or information with, each other and/or any other computer or computers 10, 20, 30, 40, and 50, described herein and/or utilized in conjunction with the present invention. In this manner, data and/or information transfer between any of the computers 10, 20, 30, 40, and 50, can communicate with any other computer or computers 10, 20, 30, 40, and 50, in a bi-directional manner.

The central processing computer(s) 10, the provider communication device(s) 20, the payer computers(s) 30, the patient computer(s) 40, and the intermediary computer(s) 50, can communicate with one another, and/or be linked to one another, over a communication network, a telecommunication network, a telephone network, a line-connected network, and/or a wireless communication network. Each of the computers 10, 20, 30, 40, and 50, can be linked with any other computer or computers directly or indirectly directly or indirectly with one another so as to facilitate a direct or indirect bi-directional communication said respective computers. Communications between each of the computers 10, 20, 30, 40, or 50 can also involve an e-mail server or e-mail servers in those instances when e-mails are described as being used to transmit or send any of the information, signals, messages, reports, notification messages, or any other communications, described herein, by or between any of the computers 10, 20, 30, 40, or 50, or when any of the information, signals, messages, reports, notification messages, or any other communications, described herein, are transmitted by and/or between any of the parties described herein and/or by or between any of the computers 10, 20, 30, 40, or 50, or any other computers or communication devices, computer systems, communication network equipment, server computers, etc., or any other devices used or needed in order to facilitate communications or the transmission of any of the herein-described information, signals, messages, reports, notification messages, or any other communications.

The apparatus 100 can also include a healthcare records computer 60 or computers (hereinafter referred to as "healthcare records computer 60" or "healthcare records computer(s) 60) which can be or can include a computer or computer system, or any number of computers or computer systems, or a cloud computer system or cloud system. The healthcare records computer can serve to store and house an electronic healthcare record or electronic healthcare files or any number of electronic healthcare records or electronic healthcare files. In the preferred embodiment, the healthcare records computer 60 can be associated with any provider, insurer, payer, intermediary, insurance exchange, or any user, individual, patient, organization, or entity, who or which utilizes the apparatus 100 and method of the present invention.

Each healthcare records computer 60 can be utilized to store an electronic healthcare record or electronic healthcare file or any number of electronic healthcare records or electronic healthcare files which can be accessed by the central processing computer 10, by any provider communication device 20, by any insurer or payer communication device 30, by any user or patient communication device 40, by any intermediary communication device 50, or by any other computer, communication device or other device described herein as being utilized in connection with the apparatus 100 and method of the present invention. The healthcare records computer 60 can also be utilized to facilitate cloud storage of any electronic healthcare record(s) or electronic healthcare file(s).

The apparatus 100 can also include an insurance exchange computer 70, or any number of insurance exchange computers 70 which can be utilized to process and store information regarding the selling of healthcare insurance, disability insurance, and life insurance, policies, products, and/or services, to any of the herein-described users, individuals, patients, or entities, who or which utilize the apparatus 100 and method of the present invention. The insurance exchange computer 70 can be utilized to advertise, provide information regarding, sell, and/or maintain records regarding, and process any other information regarding, group insurance as well as individual or family insurance policies, products, or services. The insurance exchange computer 70 can also be utilized to sell automobile, homeowners, business, and/or liability insurance policies, products, or services.

The apparatus 100 can also include a social networking computer 80. The social networking computer 80 can be linked with, and utilized in connection with, the apparatus 100 so as to allow and/or facilitate integrating the apparatus 100 of the present invention with social networks, social networking, and social media. In a preferred embodiment, for example, the social networking computer 80 can be associated with a social networking company, a social networking website, or social networking entity, website, group, organization, or association. The social networking computer 80 can be associated with any one or any number of social networking companies, social networking websites, or social networking entities, websites, groups, organizations, or associations. The social networking computer 80 can also provide links to any computers associated with any one or any number of social networking companies, social networking websites, or social networking entities, websites, groups, organizations, or associations. In the preferred embodiment, the social networking computer 80 can perform any and all of the functions performed by any social networking company, a social networking website, or social networking entity, website, group, organization, or association. In a preferred embodiment, any number of social networking computers 80 can be utilized in connection with the apparatus 100 of the present invention.

The apparatus 100 can also include a media computer 90. In the preferred embodiment, the media computer 90 can provide, and be a source of, news information, current events information, healthcare information, healthcare or healthcare-related news, current events, advertisements, and/or marketing information or materials, which can be disseminated via the apparatus 100 of the present invention, In a preferred embodiment, any number of media computers 90, with each being dedicated to providing any number, types, or kinds of, news information, current events information, healthcare information, healthcare or healthcare-related news, current events, advertisements, and/or marketing information or materials, can be utilized in connection with the apparatus 100.

In a preferred embodiment, each of the central processing computer(s) 10, the provider communications devices 20, the payer communication devices 30, the user or patient communication devices 40, the intermediary communication devices 50, the healthcare records computers 60, the insurance exchange computers 70, the social networking computers 80, and the media computers 90 can communication in a bi-directional manner with, and/or can send and/or receive signals, messages, reports, notification messages, alerts, or any other communications or electronic communication transmissions, to, from and/or between, any other, or any number of, other central processing computer(s) 10, if utilized, provider communications devices 20, payer communication devices 30, user or patient communication devices 40, intermediary communication devices 50, healthcare records computers 60, insurance exchange computers 70, social networking computers 80, and/or the media computers 90.

In a preferred, each of the central processing computer(s) 10, the provider communications devices 20, the payer communication devices 30, the user or patient communication devices 40, the intermediary communication devices 50, the healthcare records computers 60, the insurance exchange computers 70, the social networking computers 80, and the media computers 90 can be linked to or with any other central processing computer(s) 10, if utilized, provider communications devices 20, payer communication devices 30, user or patient communication devices 40, intermediary communication devices 50, healthcare records computers 60, insurance exchange computers 70, social networking computers 80, and/or the media computers 90 via a wired link or line or a wireless link.

In a preferred embodiment, each of the provider communications devices 20, payer communication devices 30, user or patient communication devices 40, intermediary communication devices 50, healthcare records computers 60, insurance exchange computers 70, social networking computers

80, and/or the media computers 90 can be connected with or linked with the central processing computer 10 as shown in FIG. 1.

In a preferred embodiment, any and/or all of the signals, messages, reports, notification messages, or any other communications, described herein as being transmitted from one device, computer, or communication device, to another, can be, or can be included in, or be attached to, an e-mail message, an instant messaging message, an electronic transmission, or an electronic data transmission or electronic data interchange, or can be transmitted via any other data or information transmission, and can be transmitted via or using any appropriate or necessary computer(s) or device(s).

In the preferred embodiment, the present invention is utilized on, and/or over, the Internet and/or the World Wide Web. The present invention, in the preferred embodiment, can also utilize wireless Internet and/or World Wide Web services, equipment and/or devices. The central processing computer(s) 10, in the preferred embodiment, has a web site or web sites associated therewith. Each of the other computers or communication devices described herein can also have a web site or web sites associated with same.

Although the Internet and/or the World Wide Web is a preferred communication system and/or medium utilized, the present invention, in all of the embodiments described herein, can also be utilized with any appropriate communication network or system including, but not limited to, a communication network or system, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

In the preferred embodiment, each of the central processing computer(s) 10, the provider communication device(s) 20, the payer communication device(s) 30, the patient computer(s) 40, the intermediary computer(s) 50, the healthcare records computer(s) 60, the insurance exchange computer(s) 70, the social networking computer(s) 80, and the media computer(s) 90, can transmit data and/or information using TCP/IP, as well as any other Internet and/or World Wide Web, and/or communication, protocols.

The apparatus 100 of the present invention can utilize electronic commerce technologies and security methods, techniques and technologies, in any and/or all of the instances of data and/or information processing, and/or data and/or information transmission described herein.

Figure 2:
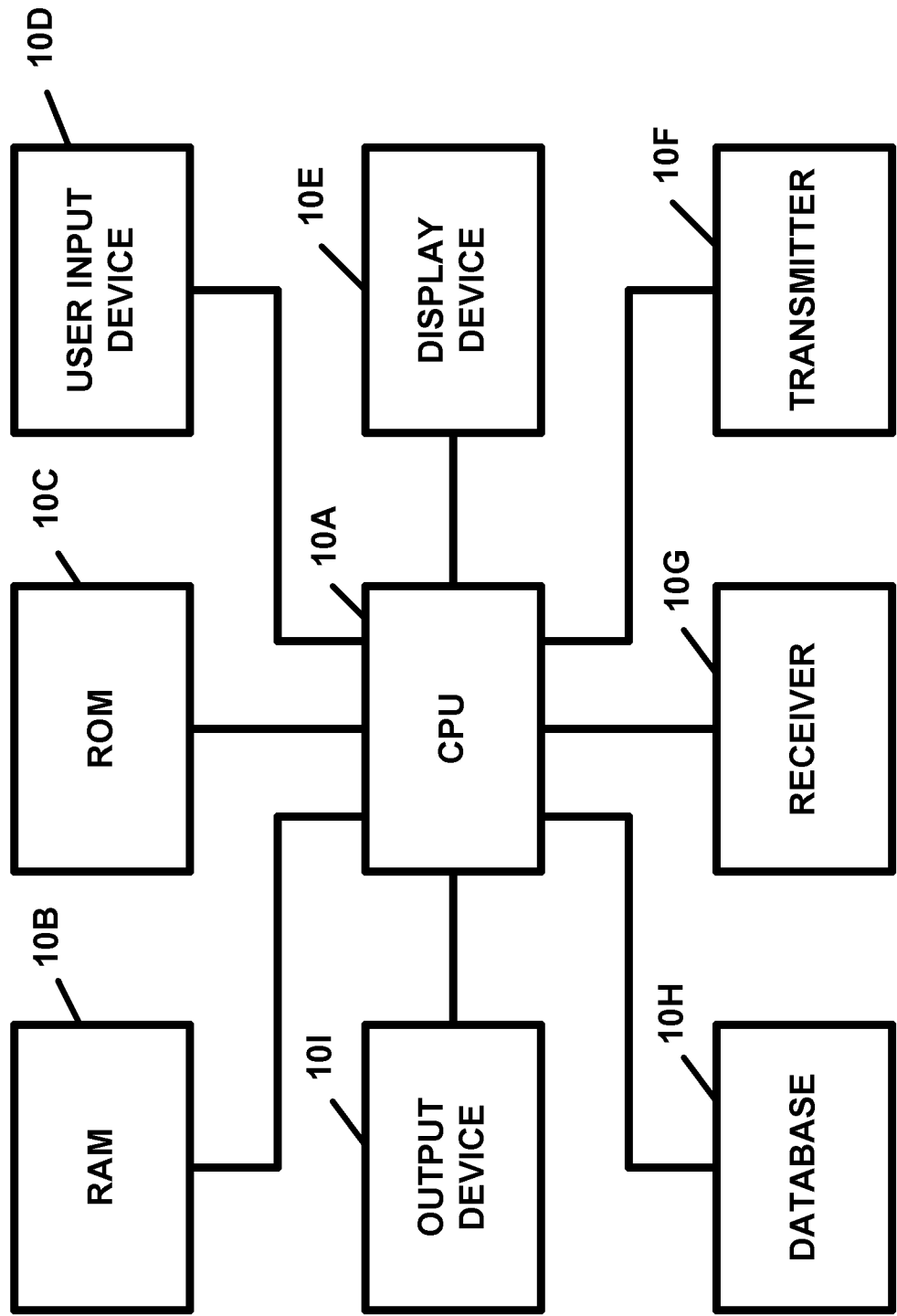
FIG. 2 illustrates the central processing computer of FIG. 1, in block diagram form.

FIG. 2 illustrates the central processing computer 10, in block diagram form. The central processing computer 10, in the preferred embodiment, is a network computer or computer system, or any other communication device which can provide the functionality of, and which can be utilized as a central processing computer such as an Internet server computer and/or a web site server computer. In the preferred embodiment, the central processing computer 10 includes a central processing unit or CPU 10A, which in the preferred embodiment, is a microprocessor. The CPU 10A may also be a microcomputer, a minicomputer, a macro-computer, and/or a mainframe computer, depending upon the application.

The central processing computer 10 also includes a random access memory device(s) 10B (RAM) and a read only memory device(s) 10C (ROM), each of which is connected to the CPU 10A, a user input device 10D, for entering data and/or commands into the central processing computer 10, which includes any one or more of a keyboard, a scanner, a user pointing device, such as, for example, a mouse, a touch pad, and/or an audio input device and/or a video input device, a microphone or audio recording device, a camera or a video recording device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 10A. The central processing computer 10 also includes a display device 10E for displaying data and/or information to a user or operator.

The central processing computer 10 also includes a transmitter(s) 10F, for transmitting signals and/or data and/or information to any one or more of the central processing computer(s) 10, the provider communication device(s) 20, the payer computers(s) 30, the patient computer(s) 40, and the intermediary computer(s) 50, the healthcare records computer(s) 60, the insurance exchange computer(s) 70, the social networking computer(s) 80, and the media computer(s) 90, or any other individual computer(s), which may be utilized in conjunction with the present invention. The central processing computer 10 also includes a receiver 10G, for receiving signals and/or data and/or information from any one or more of the central processing computer(s) 10, the provider communication device(s) 20, the payer computers(s) 30, the patient computer(s) 40, and the intermediary computer(s) 50, the healthcare records computer(s) 60, the insurance exchange computer(s) 70, the social networking computer(s) 80, and the media computer(s) 90, which may be utilized in conjunction with the present invention.

The central processing computer 10 also includes a database(s) 10H which contains data and/or information pertaining to the patients, providers, payers, and intermediaries who or which are serviced by the present invention and/or who or which utilize the present invention.

The database 10H can contain any one or any number of electronic healthcare records (EHRs), which electronic healthcare records definition includes electronic healthcare records or electronic healthcare files, electronic medical records or electronic healthcare files (EMRs), electronic dental records or files (EDRs), electronic pharmacy records or files (EPRs), electronic behavioral health records or files (EBHRs), as well as any personal health records or files (PHRs). The database 10H can also contain any links or hyperlinks to any of the above electronic healthcare records or electronic healthcare files, electronic medical records or files, electronic dental records or files, electronic pharmacy records or files, electronic behavioral health records or files, and/or personal health records or files, which may be located or stored on any computer or computers external from the central processing computer 10, for any number of users, individuals, or patients.

Each of the herein-described electronic healthcare records, electronic medical records, electronic dental records, electronic pharmacy records, and/or electronic behavioral health records can also contain a personal health record portion. The apparatus 100 and method of the present invention can store a personal health record for each individual or patient. The personal health record can be stored in each individual's or patient's respective electronic healthcare record(s), electronic medical record(s), electronic dental record(s), electronic pharmacy record(s), and/or electronic behavioral health record(s), as well as in any user or patient communication device 40. The personal healthcare record can be updated as described herein or in any other appropriate manner.

The database 10H can also contain a look-up table or look-up tables and/or data and/or information relating thereto, for identifying and locating a respective electronic healthcare record(s), an electronic medical record, an electronic dental records, an electronic pharmacy record, an electronic behavioral health record, or a personal health records, for or associated with any user, individual, patient, or person who may utilize the apparatus 100 of the present invention. In this regard, the database 10H can store any healthcare data and/or information or healthcare-related data and/or information for any user, individual, patient, or person who may utilize the apparatus 100 of the present invention, whether that information is stored in the central processing computer 10, the database 10H, or any provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90, regardless of where these computers or communications devices are located and regardless of what data and/or information is stored on same.

In the preferred embodiment, the database 10H contain data and/or information for locating, retrieving, storing, or providing a comprehensive healthcare record of healthcare file for any individual, user, patient, or person. The database 10H can also contain any necessary data or information for locating, identifying, retrieving, storing, any information from any of the various types of kinds of electronic healthcare records or electronic healthcare files regarding of the type, kind, and/or vendor or supplier of same, regardless of where these electronic healthcare records or electronic healthcare files are located or stored. In a preferred embodiment, the database 10H can also contain an index or other information for identifying data fields in the respective databases of the various respective electronic healthcare records for enabling the central processing computer 10 to identify data and/or information in each of the respective electronic healthcare records or electronic healthcare files.

The database 10H can also contain any data and/or information for allowing any herein-described user, individual, patient, person, provider, payer, intermediary, or entity, to access or obtain any of the herein-described data and/or information, wherever such data and/or information is located or stored, as well as to perform any function described herein as being capable of being performed by the apparatus 100 of the present invention.

The database 10H can also contain any data and/or information for integrating, linking to or with, and/or accessing data and/or information stored or located in, any number, type, or kind, of any of the herein-described electronic healthcare records or electronic healthcare files, electronic medical records or files, electronic dental records or files, electronic pharmacy records or files, electronic behavioral health records or files, as well as any personal health records or files.

The database 10H can contain any of the herein-described data and/or information for any number of individuals, users, patients, or persons. The database 10H can also contain data and/or information regarding a name, relationship, and authorization for any parent, relative, legal guardian, caregiver, healthcare proxy holder, or any person, individual, or entity, who or which may be responsible for caring for, accessing, updating, or maintaining healthcare records or files for, making decisions for, or making healthcare-related decisions for, taking actions for, providing care for, or performing any task or activity for, any other individual(s), user(s), patient(s), or person(s). For example, the database 10H can, for a child, contain information regarding the child's parent or legal guardian, and for the database 10H, for an elderly person of any other person, contain information regarding the person's child, caregiver, healthcare proxy holder, or any other authorized person or entity, or for individuals who belong to a school or club's athletic program, or a sports team, a club, a social or other organization, the database 10H can contain information regarding a coach, team doctor, trainer or other authorized individual.

The database 10H can contain any and/or all of the information needed and/or required in order to perform any and/or all of the functions, services and/or operations described herein as being performed by the central processing computer 10 or the apparatus 100 of the present invention. In this regard the database 10H can contain data and/or information regarding patient name, patient identification information, patient social security number or other identification information, date of birth, sex, gender, race, nationality, ethnicity, spoken language, preferred language, other languages, religion or religious affiliation, next-of-kin, relatives, emergency contact person, doctors or providers, therapists, nutritionists, insurance or payer information, group insurance information, group health insurance information, life insurance information, disability insurance information, patient address, phone number, e-mail and/or other contact information, medical history, psychological history, dental history, family history, family medical, psychological, and/or dental history, past and/or current or active symptoms, past and/or current or active diagnoses, past and/or current or active treatments or treatment plans, care management plan or plans, allergies, active or current medications or prescription drugs, active or current medication allergies, past, active, or current allergies, smoking status, insurance coverage, insurance co-payment and/or deductible information, co-payment information regarding any payer or insurer insurance policy or payment plan, deductible information regarding any payer or insurer insurance policy or payment plan, benefit eligibility information, insurance information, insurance claim procedures, insurance claim forms, doctor or provider appointment schedules, past treatments, past diagnosis, symptoms, insurance claim forms, employer information, lifestyle information, treatment plans, treatment progress, broker/agent/intermediary information, education information, age, sex, marital status, employee benefits information, types or services and/or treatments needed, and any other data and/or information regarding the patient which would be needed and/or desired in order to perform any and/or all of the functions, services and/or operations described herein.

The database 10H can also contain provider office visit summaries, hospital discharge summaries, hospital discharge instructions, and/or any examination, treatment, testing, or procedure, summary, and any instructions, treatment plan or instructions, care management plan or instructions, or any other information which can be provided to any individual, patient, provider, payer, insurer, third party or intermediary, or caregiver, described herein as using the apparatus 100 and method of the present invention, or described herein as being able to receive services, provide services, or otherwise use or be serviced by, the apparatus 100 and method of the present invention.

In the case of deceased patients or individuals, the database 10H can contain information regarding date of death, place of death, preliminary cause of death, and/or final determination of cause of death. The database 10H can also contain information regarding any other information regarding a deceased patient or individual and can also contain information regarding final resting place.

The database 10H can also contain, for each patient or individual, information regarding dates of appointments or services with or from healthcare providers or other providers, dates of laboratory tests, dates of treatments, operations, or procedures, dates of doctor visits, therapy sessions, vital signs, healthcare chart changes, or information regarding height, weight, blood pressure, heart rate, pulse rate, body-mass index, growth charts, and/or any other related or pertinent data or information.

The database(s) 10H can also contain healthcare and/or medical video, image, and/or audio, and/or text, data and/or information, and/or surgical video, image, and/or audio, and/or text, data and/or information, and/or dental video, image, and/or audio, and/or text, data and/or information, such as, for example, x-rays, Magnetic Resonant Images (MM), CAT scans, digital x-ray files, digital Magnetic Resonant Imaging (MM) files, digital CAT scan files, and/or any other video, imaging, and/or audio, healthcare data and/or information which can be utilized by healthcare providers, payers, intermediaries, patients, and/or other users of the present invention. In this manner, the present invention can facilitate the availability of any of the above-described video, image, and/or audio, data and/or information in a network environment. For example, a medical specialist can have access to, and/or review, an MM or a CAT scan for a patient, from any location and at any time.

The database 10H can also contain data and/or information regarding providers including provider name, provider social security number or identification number, type of professional or service provider, address, phone number, fax number, e-mail and/or other contact information, experience, specialties, insurances accepted, schedule of charges, financial account identification information, resume information, education, work experience, claim forms, appointment schedules, procedures performed, and/or any other data and/or information concerning the providers for providing any and/or all of the functions, services, and/or operations described herein as being performed by the present invention.

The database 10H can also contain data and/or information regarding all possible fields of medicine, surgery, psychiatry, psychology, dentistry, oral surgery, optometry, podiatry, physical therapy, respiratory therapy, hypnosis, osteopathy, nutrition, wellness, and/or any other possible healthcare fields and/or subject matter which can possibly by utilized in the processing and/or operation of the present invention.

The database 10H can also contain information on illnesses, symptoms, diseases and/or sicknesses, theories, scientific theories, research data and/or information, diagnosis information, treatment information, treatment plans, treatment processes, treatment progresses, treatment interactions, side effects, expected treatment results, treatment providers, treatment durations, treatment costs, pre-treatment information, post-treatment information, treatment monitoring information, statistical information regarding diagnoses, treatments, treatment success rates, treatment failure rates, treatment centers, therapy plans, therapy success rates, therapy failure rates, treatment procedures, medications treatments, non-medication treatments, healthcare institutions, treatment evaluating criteria, treatment mistakes and/or mishaps, indicators of mistakes and/or mishaps, corrective actions, links to providers, links to treatment centers or institutions, reimbursement rates, nutrition information, diet information, exercise information, exercise routines, treatment options, healthcare advise, wellness advice, preventive care, preventive procedure, health maintenance, drug and medication information, drug interaction information, video information, including video files or clips and other information, regarding illnesses, diseases, treatments and follow-up care, audio information, including audio files or clips and other information, regarding illnesses, diseases, treatments and follow-up care, treatment and/or procedure information and/or narratives, treatment analysis, diagnosis analysis, diagnosis monitoring, diagnosis confirmation and/or checking, and/or other information for providing the herein-described functions, services, and/or operations.

The database 10H can also contain information regarding the insurance companies and payers described herein, including, but not limited to, payer name, address, phone number, fax number, e-mail address, identification number(s), coverage types, policies and/or coverages provided, reimbursement rates, patients and/or providers serviced and/or covered by the payer, policy information, claim forms, claim procedures, claim status, claim processing information, claim submission procedures and policies, reasonable and customary charges, co-payment information, pre-approval information and/or procedures, claim form information, electronic form claim forms, insurance and/or coverage requirements, guidelines, and/or triggering events, covered procedures and/or treatments, uncovered procedures and/or treatments, claim approval information, claim approval history, claim approval statistics, claim rejection or denial information, claim rejection or denial history, claim rejection or denial statistics, financial account information, network provider information, network patient information, claim statistics, preventative care and/or benefits information, benefits information, benefits request information and/or claim forms, claim submission information, claim processing information, claim status information, payment information and statistics, and/or any other data and/or information regarding and/or related to payers which are needed and/or desired for providing any and/or all of the functions, services, and/or operations described herein.

The database 10H can also contain data and/or information regarding the brokers, agents and/or intermediaries described herein, including, but not limited to, intermediary name, address, phone number, fax number, e-mail address, clients, patients services, insurance policies, policy information, policy quote information, policy proposal information, any and/or all of the above information described herein regarding patients, providers, payers, etc. which may be of interest to the intermediaries described herein which may be useful and/or beneficial to the intermediaries in providing any of the functions, services, and/or operation described herein.

The database 10H can also contain contact information such as phone numbers, fax numbers, pager numbers, beeper numbers, e-mail addresses, hyperlinks to, and/or any other information which can facilitate contact between any of the parties described herein. The database 10H also includes electronic signature data and/or information for any of the parties, patients, providers, payers, and/or intermediaries, described herein for facilitating transactions, claim submissions, financial transactions, etc., by and/or between any of the above patients, providers, payers, and/or intermediaries.

The database 10H can also contain and notes, comments, or messages, which can be provided by any user, individual, patient, caregiver, provider, insurer, payer, third party, intermediary, or any other person or entity who or which utilizes the apparatus 100 and method of the present invention.

The database 10H can also contain any number of electronic healthcare records, electronic medical records, electronic dental records, electronic pharmacy records, electronic behavioral health records, and/or links to other electronic healthcare records, electronic medical records, electronic dental records, electronic pharmacy records, electronic behavioral health records which might be located in healthcare records computers 60 or other computers or computer systems located remote from the central processing computer 10. Any and/or all of these electronic healthcare records, electronic medical records, electronic dental records, electronic pharmacy records, electronic behavioral health records can contain data and/or information and/or link or hyperlinks to data and/or information regarding any individuals, patients, his or her caregivers, children, parent, relatives, friends, social networking friends, connections, of followers, providers, insurers or payers. The databases 10H can also contain any and/or all information regarding the data and/or information fields in each electronic healthcare record, electronic medical record, electronic dental record, electronic pharmacy record, and/or electronic behavioral health record, information for mapping common or like data fields for each and information or links or hyperlinks for accessing like data or like information fields in each of the different electronic healthcare records, electronic medical records, electronic dental records, electronic pharmacy records, electronic behavioral health records.

The data and/or information in the database 10H can also include links to any other information, information sources, news sources, and/or other information and/or data which can or may be utilized by the present invention and/or by any of the patients, providers, payers, intermediaries and/or any other users of the present invention.

The database 10H can also contain data and/or information regarding healthcare news, healthcare developments, healthcare discoveries, etc., for and including the medical field, surgical field, psychological field, dental field, nutrition field, fitness field, etc., and/or any other healthcare field or fields.

The database 10H, in the preferred embodiment, can also contain video and/or audio files which can be utilized for training of healthcare professionals as well as for providing general information to any user of the present invention. In this manner, and as will be described hereinbelow, the apparatus 100 can be utilized as a simulator for providing training in medical diagnosing, medical training, surgical training, psychiatric training, psychological training, dental training, oral surgery training, therapist training, and/or for training any of the healthcare providers described herein and/or envisioned.

For example, the present invention can be utilized to provide a medical doctor with a set of symptoms, evaluate the diagnosis and treatment prescribed and provide follow-up patient conditions which may or may not call for the medical doctor to re-evaluate his or her diagnosis and/or treatment. In a similar fashion, the present invention can be used for training and continuing education and training for any of the healthcare providers described herein and/or otherwise envisioned utilizing the present invention.

The database 10H can also contain data and/or information restricting access by any of the providers, payers, patients, intermediaries, and/or other users, to any of the data and/or information stored in the database 10H.

The database 10H can also contain information correlating symptoms and/or conditions with diagnoses, prognoses, and/or treatments, treatment methods, procedures, etc. The database 10H also contains any and/or all information needed and/or desired for facilitating the processing of symptoms, conditions, medical histories, family histories, and other information, in order to arrive at diagnoses and/or prognoses, treatments, prescriptions, procedures and/or any other healthcare and/or healthcare-related information.

The database 10H can also contain information regarding medical records, medical charts, x-rays, MRIs, and/or any other information, described herein and/or otherwise, which can be associated with an individual's or patient's medical history, medical record, or medical file, for any individual or patient who utilizes the apparatus 100 and method of the present invention.

The database 10H can also contain information regarding surgical records, surgical charts, x-rays, MRIs, and/or any other information, described herein and/or otherwise, which can be associated with an individual's or patient's surgical history, surgical record, or surgical file, for any individual or patient who utilizes the apparatus 100 and method of the present invention.

The database 10H can also contain information regarding dental records, dental charts, x-rays, and/or any other information, described herein and/or otherwise, which can be associated with an individual's or patient's dental history, dental record, or dental file, for any individual or patient who utilizes the apparatus 100 and method of the present invention.

The database 10H can also contain information regarding a prescription drug record, file, or account, for an individual or patient for any individual or patient who utilizes the apparatus 100 and method of the present invention.

The database 10H can also contain information regarding a healthcare spending account or healthcare spending accounts for any individual or patient, or for any of the individuals or patients, described herein or otherwise, who utilize the apparatus 100 and method of the present invention. For example, the healthcare spending account is or can be an account which can be a deposit account, a credit account, a debit account, an electronic money or an electronic cash account, or any combination of same, which can be held by any individual, patient, employer, bank, credit union, financial institution, investment institution, healthcare insurer, healthcare payer, or any other third party, and which can be used as a source of funds for payment for any type of healthcare service or healthcare product which is provided to, or administered to, or sought by, any individual or patient who utilizes the apparatus 100 and method of the present invention. In a preferred embodiment, the healthcare spending account can be used by the individual or patient to pay for any healthcare service, treatment, procedure, or product, at any time a payment is desired to be made for same.

The database 10H can also contain and/or include, for each individual, patient, caregiver, healthcare provider, or any other provider, healthcare insurer or healthcare payer, or any intermediary, who or which utilizes the apparatus 100 of the present invention, information regarding, or a link or a hyperlink, to any information regarding a telephone number or an IP address, or other contact information, for to regarding any communication device or computer which can be utilized by the respective individual, patient, caregiver, healthcare provider, or any other provider, healthcare insurer or healthcare payer, or any intermediary, in making and/or in engaging in any of the video calls, video chat sessions, or videoconferences, described herein.

The database 10H can also contain and/or include, for each healthcare provider who or which utilizes the apparatus 100 of the present invention and who or which desires to engage in video calls, video chat sessions, or videoconferences, and/or in remote or virtual office visits or in remote or distance examinations, any data and/or information or a link or hyperlink to any data and/or information regarding or containing the healthcare provider's work schedule(s) as well any information for allowing any individual, patient, or caregiver, to schedule and/or conduct a video call, a video chat session, or a videoconference, and/or a remote or a virtual office visit or a remote or a distance examination, with the healthcare provider.

The database 10H can also contain and/or include, for each healthcare provider who or which utilizes the apparatus 100 of the present invention and who or which desires to engage in video calls, video chat sessions, or videoconferences, any data and/or information or a link or hyperlink to any data and/or information regarding or containing the healthcare provider's work schedule(s) as well any information for allowing any healthcare insurer or healthcare payer, or any intermediary, to schedule and/or conduct a video call, a video chat session, or a videoconference, with the healthcare provider.

The database 10H can also contain and/or include, for each healthcare insurer or healthcare payer who or which utilizes the apparatus 100 of the present invention and who or which desires to engage in video calls, video chat sessions, or videoconferences, any data and/or information or a link or hyperlink to any data and/or information regarding or containing the healthcare insurer's or healthcare payer's work schedule(s) as well any information for allowing any individual, patient, or caregiver, or any healthcare provider, or any intermediary, to schedule and/or conduct a video call, a video chat session, or a videoconference, with the healthcare insurer or the healthcare payer.

The database 10H can also contain and/or include, for each intermediary who or which utilizes the apparatus 100 of the present invention, and who or which desires to engage in video calls, video chat sessions, or videoconferences, any data and/or information or a link or hyperlink to any data and/or information regarding or containing the intermediary's work schedule(s) as well any information for allowing any individual, patient, or caregiver, or any healthcare provider, or any healthcare insurer or healthcare payer, to schedule and/or conduct a video call, a video chat session, or a videoconference, with the intermediary.

The database 10H can also contain and/or include, for each healthcare provider who or which has registered with the apparatus 100 in order to engage in video calls, video chat sessions, or videoconferences, in order to provide remote or virtual office visits or in order to provide remote or distance consultations or examinations with and for any individuals or patients, or caregivers, any data and/or information regarding the healthcare provider's name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

The database 10H can also contain, for each individual or patient who utilizes the apparatus 100 and method of the present invention, information regarding, or a record of, each and every instance of a provider office visit involving the individual or patient, a communication(s) with a provider or providers involving or regarding the individual or patient, a payment(s) made by or on behalf of the individual or patient, an insurance claim(s) made by a provider or providers on a healthcare insurance policy or account for or regarding the individual or patient, including information regarding date of claim, time of claim, or the provider making the claim, a co-payment(s) made by or on behalf of the individual or patient, a payment(s) made on an insurance claim, a denial(s) of an insurance claim or insurance claims, or a resolution(s) of an insurance claim or insurance claims. The database 10H can also contain information regarding a history or record of insurance claims made by a provider or providers, or made by an individual or patient, for each individual or patient who utilizes the apparatus 100 and method of the present invention.

The database 10H can also contain and/or include, for each individual, patient, or caregiver of or for the individual or the patient, any recordings of any of the herein-described video calls, video chat sessions, or video conferences, in which the individual, patient, or caregiver of or for the individual or the patient, was a party to or participated in.

The database 10H can also contain and/or include for each individual, patient, or caregiver of or for the individual or the patient, any of the herein-described video call reports, remote or virtual office visit reports, remote or distance examination reports, insurance claim forms, request for payment forms, and/or request for payment of co-payment forms, generated for, pertaining to, or associated with, the each individual, patient, or caregiver of or for the individual or the patient.

The database 10H can also contain credit report data or information, a credit report, credit reports, or a credit history, for any individual or patient, or for any of the individuals or patients, described herein or otherwise, who utilize the apparatus 100 and method of the present invention. The credit report or credit reports, or credit history, can contain any of the information which is typically provided by, or which may be provided by, any commercial or other credit reporting company or agency, such as, for example, but not limited to, credit reporting companies such as TransUnion LLC, Experian Information Solutions, Inc., Equifax, Inc., or any other credit reporting company, agency, or bureau, or any credit card company or financial institution. The database 10H can also contain any data or information which is typically found in a credit report database or credit history database, and/or any data and/or information which is, or which can be, utilized in generating, and/or analyzing, a credit report or credit reports, or a credit history, for, or on behalf of, any individual or patient, or for any of the individuals or patients, described herein or otherwise, who utilize the apparatus 100 and method of the present invention. The database 10H can also contain e-mail contact information, telephone contact information, cellular telephone contact information, and/or any other suitable contact information, for an individual or patient which can be utilized to notify the individual or patient when information regarding his or her credit report or credit reports, or credit history, is accessed, obtained, changed, or when a new entry of information is made in same.

The database 10H can also include advertisements, advertisement materials and information, marketing materials or information, commercials, video clips, infomercials, and any other information, which can include text information, video information, audio information, or any combination of same, which can be used to provide an advertisement, or advertisement material or information, to or for any individual, patient, provider, healthcare provider, payer, healthcare payer, insurer, healthcare insurer, product provider, service provider, third party provider, or any other person or entity, who or which utilizes the apparatus 100 and method of the present invention. A respective advertisement, advertisement material and information, marketing material or information, commercial, video clips, infomercials, and/or any other information, can be used to advertise or market any product(s) or service(s) which can be used by, provided to, provided by, advertised to, advertised by, marketed to, or marketed by, any individual, patient, provider, healthcare provider, payer, healthcare payer, insurer, healthcare insurer, product provider, service provider, third party provider, or any other person or entity, who or which utilizes the apparatus 100 and method of the present invention.

The database 10H can also contain news information, news reports, published reports, theses, study reports, or any other data or information regarding health issues, healthcare issues, health conditions, diseases, treatments, drugs, medications, healthcare procedures, medical procedures, surgical procedures, dental procedures, prescription products or services, non-prescription products or services, over-the-counter products or services, health or wellness issues or recommendations, exercise issues or recommendations, alternate therapy or treatment types or recommendations, herbal therapies or recommendations, or any other data or information which can be used by or provided to any individual, patient, provider, healthcare provider, payer, healthcare payer, insurer, healthcare insurer, product provider, service provider, third party provider, or any other person or entity, who or which utilizes the apparatus 100 and method of the present invention. The news information, news reports, published reports, theses, study reports, or any other data or information can include text information, video information, audio information, or any combination of same.

The news information, news reports, published reports, theses, study reports, or any other data or information, stored in the database 10H, can be transmitted to, or fed to, the central processing computer 10, for storage in the database 10H, by or from any appropriate computer or communication device, which is associated with or used by any news source, news organization, research institution, research professional, healthcare facility, an author, researcher, academician, or any other individual, person, or entity. An intermediary communication device 50 can also be utilized to transmit the news information, news reports, published reports, theses, study reports, or any other data or information to the central processing computer 10.

The database 10H can also contain prescription drugs information, prescription medication information, over-the-counter drug or medication information, wellness information, exercise and fitness information, and/or any other information pertinent to an individual's or a patient's heath, well-being, or treatment.

The database 10H can also include language translation information or software so that any of the data or information described herein as being stored in the database 10H, or as being provided in any of the messages, reports, or other communications, described herein can be translated into any language.

The database 10H can also contain, for each individual, patient, provider, and/or insurer or payer who or which utilize the apparatus 100, data and/or information regarding charges made to an individual or patient, charges made by a provider, charges made by an insurer or payer, amounts paid to an individual or patient, amounts paid by an individual or patient to a provider, amounts paid by an insurer or payer to a provider, amounts paid by an insurer or patient to an individual or patient, amounts paid by an individual or patient to an insurer or payer, a charges-back(s) made regarding a payment to, for, or by, a provider, a charge-back(s) made regarding a payment to, for, or by, an individual or patient, and/or a charge-back(s) made regarding a payment to, for, or by, an insurer.

The database 10H can also contain any notes, comments, or messages, which can be provided in text, in audio recordings or audio clips, and/or in video recordings or video clips. The database 10H can also contain any data, information, and/or software programs for translating audio information to text information and for translating test information to audio information. The database 10H can also contain any data, information, and/or software programs for translating text information or audio information from one language to another so as to provide a multi-lingual healthcare information and records keeping system. The database 10H can also contain any notes, comments, or messages, which can be provided by any of the herein-described users, individuals, patients, providers, insurers, payers, third parties, intermediaries, and/or any other person or entity who or which utilizes the apparatus 100 and method of the present invention.

The database 10H can also contain any notes, comments, or messages, which can be stored in any and/or all of the electronic healthcare records or electronic healthcare files, electronic medical records or files, electronic dental records or files, electronic pharmacy records or files, electronic behavioral health records or files, and/or personal health records or files, described herein as being utilized in connection with the apparatus 100 and method of the present invention. In this regard, it is important to note that, in a preferred embodiment of the present invention, any and/or all of the electronic healthcare records or electronic healthcare files, electronic medical records or files, electronic dental records or files, electronic pharmacy records or files, electronic behavioral health records or files, and/or personal health records or files, described herein as being utilized in connection with the apparatus 100 are or can be designed to receive, store, and/or provide, any notes, comments, and/or messages, provided by any of the herein-described users, individuals, patients, providers, insurers, payers, third parties, intermediaries, and/or any other person or entity, as text information or in text form, as audio information or in audio form, or as video information or in video form. Any text or audio information can be translated to from text to audio or from audio to text, and any text or audio information can be translated from one language to any one of more of any other language.

The database 10H can also contain sports medicine-related data and/of information for and including healthcare records, histories, or files, of and for athletes or sports participants of any age and in or for any sport or athletic activity. The database 10H can also contain data and/or information regarding healthcare records, histories, and/or files, for any athletes or sport participants and their respective organizations, teams, clubs, leagues, or other entities. The database 10H can also contain data and/or information for creating and for maintaining a comprehensive and/or centralized sports medicine healthcare record, history, and/or file, system for athletes or participants of any sport or sports or any activity or activities, athletes or sports participants of any age, professional athletes, minor league athletes, Olympic athletes, competitive athletes, government team athletes, world class competition athletes, amateur athletes, college athletes, high school age athletes, children athletes, secondary school athletes, recreational organization athletes or members, child recreational organization athletes or members, adult recreational organization athletes or members, little league athletes or members, boys club athletes or members, girls club athletes or members, hobbyist athletes, or any other individuals, male or female, who participate in athletic endeavors, sporting events, exercise activities or programs, the martial arts, mixed martial arts, boxing and other fighting or combat sports, any and/or all team sports, including but not limited to baseball, football, basketball, hockey, soccer, lacrosse, track and field, gymnastics, car racing, skiing and winter sports, swimming and aquatic sports, weightlifting, dancing, and/or any other sports or sporting activities, and/or other physical activities, or any team sporting activities or individual sporting activities.

The database 10H can also contain data and/or information regarding any organization, governmental entity, business, team, league, club, network, or any other entity, which oversees, manages, uses, employs, provides oversight over, owns or otherwise has playing or managing rights over, provides control over, or provides or is responsible for the healthcare of, any of the herein-described or other athletes or sports participants.

The database 10H can also contain data and/or information for or regarding sports-related injuries or athletic related injuries, or conditions, or other healthcare information relating to sports-related injuries, athletic injuries, sport-related conditions, and/or athletics-related conditions.

The database 10H can also contain data and/or information for diagnosing, treating, treatment planning, curing, rehabilitating, and/or for performing therapy or therapies for, sports-related injuries or conditions or athletic-related injuries or conditions. The database 10H can also contain information regarding diagnoses, treatments, treatment plans, procedures, corrective procedures or surgical procedures, cures, rehabilitation, therapies, physical therapies, exercise therapies, drug or medicinal therapies, diets, nutritional therapies, alternate medicine therapies, herbal therapies, and/or any other information which can or which may be utilized or needed for monitoring and/or managing the health and well-being of athletes or sports participants.

The database 10H can also contain data, information, or algorithms, for devising and planning treatments, treatment plans, procedures, operations, rehabilitation programs, plans, or regimens, physical therapy programs, plans, or regimens, occupational therapy programs, plans, or regimens, exercise programs, plans, or regimens, massage therapy programs, plans, or regimes, and/or any other programs, plans, or regimens for treating, curing, or otherwise dealing with, a sports-related injury or diagnosis.

The database 10H can also contain data and/or information regarding, for identifying or locating, healthcare providers, doctors, specialists, dentists, dental specialists, psychiatrists, psychologists, chiropractors, podiatrists, optometrists, or any other providers, hospitals, treatments facilities, therapists, nurses, physical therapists, massage therapists, occupational therapists, trainers, and/or any other providers or care givers, and/or testing laboratories, who or which can provide services for any other athletes and/or sports participants who may or which my utilize or be serviced by the apparatus 100 and method of the present invention, or any of their respective organizations, teams, clubs, or other entities.

The database 10H can also contain information, text information, audio, audio information or audio clips, video, video information, video clips, audio and video information, audio and video clips, news story, television programs, and/or information in any other form or type regarding fitness, fitness exercises, exercises, fitness routines, fitness regimens, wellness, wellness exercises, wellness routines, wellness regimens, diets, diet exercises, diet or dieting routines, diet or dieting regimens, training, training principals, training exercises, training routines, training regimens, nutrition, health and well being, meditation and any other information.

The database 10H can also contain statistical and/or other probabilistic and/or mathematical information for assigning and/or correlating certain levels and/or estimates for any and/or all of the information, diagnoses, prognoses, treatments, procedures, and/or any other information processed and/or generated by the central processing computer 10 and/or the apparatus 100.

The database 10H, in the preferred embodiment, can be a database which may include individual databases or collections of databases, with each database being designated to store any and all of the data and/or information described herein. The database 10H, or collection of databases, may be updated by each of the respective patients, providers, payers, users, and/or intermediaries, and/or by any other third party, in real-time, and/or via dynamically linked database management techniques.

The data and/or information stored in the database 10H can also be updated by and/or dynamically linked to, various external sources, including but not limited to news services, research publications, research facilities, healthcare laboratories, providers of healthcare goods and/or services, pharmaceutical companies, research institutions, schools. The database 10H will contain any and all information deemed necessary and/or desirable for providing all of the processing and/or services and/or functions described herein.

The database 10H can also contain data and/or information regarding any and/or all International Classification of Diseases (ICD) codes, ICD-10 codes, ICD-9, or any other ICD codes, or other codes, billing codes, diagnostic codes, treatment codes, or symptom codes, as well as any other codes or coding information which pertains to healthcare, the administration of healthcare services, healthcare record keeping, healthcare billing, healthcare diagnostics, healthcare treatments, or any other healthcare or healthcare-related functions or services, or any information or function, described-herein as capable of being provided by the apparatus 100 and method of the present invention. The database 10H can also contain data and/or information regarding the foreign language translations or conversions of or for, or for the foreign language translation or converting, of any of the herein-described International Classification of Diseases (ICD) codes, ICD-10 codes, ICD-9, any other ICD codes, or other codes, billing codes, diagnostic codes, treatment codes, symptom codes, as well as any other codes or coding information which pertains to healthcare, the administration of healthcare services, healthcare record keeping, healthcare billing, healthcare diagnostics, healthcare treatments, or any of the healthcare or healthcare-related functions or services, or any information or function described herein as capable of being provided by the apparatus 100 and method of the present invention, into any one or any number of foreign languages.

The database 10H can contain any look-up tables, or information for use in a look table, for translating or converting any of the data, information, or codes, described herein, into any one or any number of foreign languages. The database 10H can also contain any language translation software or language conversion software which can be used to perform any of the foreign language translation or foreign language conversion processing or functionality described as being performed by the apparatus 100 and method of the present invention.

The database 10H can also contain any information or software, or rules algorithms, which can be used in generating insurance claim forms which can be submitted error-free to any of the insurers or payers described herein.

The database 10H can also contain digital pictures, photographs, images, video, or video clips, of individuals or patients, as well as digital pictures, photographs, images, video, or video clips, of physical conditions of or regarding an individual or patient, which can be accessed or retrieved by any of the individuals, patients, providers, payers, or intermediaries, described herein as utilizing the apparatus 100 and method of the present invention.

For example, in instances where photographs or images can be useful to see a state of a physical condition of a patient or individual, or to compare a state of a physical condition from one point in time to another, or to track the state of a physical condition, a photograph(s), picture(s), or image(s), or video clip, can be digitally recorded, with a camera or video recording device, and stored in the database 10H and/or in the patient's or individual's healthcare record or healthcare file for later retrieval, use, and/or review.

For example, a dermatologist seeking to determine if a skin condition has or is changing in size, shape, or color, can take and store, in the database 10H and/or in the patient's or individual's healthcare record or healthcare file, one or more photographs, pictures, or images, or a video clips, of the skin condition. In an analogous manner, a plastic surgeon can obtain and store, in the database 10H and/or in the patient's or individual's healthcare record or healthcare file, photographs, pictures, or images, or video clips, showing physical conditions of an individual or patient before, after, or during a procedure or procedures. A dentist or an oral health professional can obtain and store, in the database 10H and/or in the patient's or individual's healthcare record or healthcare file, in addition to x-rays, a photograph(s), picture(s), or image(s), or a video clip(s), showing physical conditions of an individual's or patient's mouth, teeth, gums, or other physical oral state, for later retrieval, use, or review. In an analogous manner, any healthcare provider can obtain and store, in the database 10H and/or in a patient's or individual's healthcare record or healthcare file, a photograph(s), picture(s), or image(s), or a video clip(s), obtained in or during an office visit, an examination, a procedure, an operation, a treatment, or during any other occasion, event, occurrence, or happening, for later retrieval and use as needed or desired by any provider, payer, patient, individual, or intermediary, described herein as being able to utilize the apparatus 100 and method of the present invention.

The database 10H can also contain video and/or audio clips or recordings of office visits, examinations, procedures, operations, or any other healthcare, healthcare-related, or any other event(s), occurrence(s), or happening(s), which may or which can be of interest to any provider, insurer, payer, patient, individual, or intermediary, described herein as being able to utilize the apparatus 100 and method of the present invention.

The database 10H can also contain transcripts of office visits, examinations, procedures, operations, or any other healthcare, healthcare-related, or any other event(s), occurrence(s), or happening(s), or any video calls, video chat sessions, or videoconferences of any a remote or virtual office visits or any remote or distance examinations, which may or which can be of interest to any provider, insurer, payer, patient, individual, or intermediary, described herein as being able to utilize the apparatus 100 and method of the present invention.

The database 10H can also contain data, information, links, or hyperlinks, which can allow a healthcare provider to create or generate and/or transmit prescriptions or electronic prescriptions, or prescription forms, to pharmacies or other providers, for a patient or individual, or prescriptions or electronic prescriptions for tests, analyses, analysis workups, procedures, therapy, physical therapy, or other healthcare or healthcare-related services, for a patient or individual, or which can allow a healthcare provider to transmit a referral or an electronic referral or referral form to other healthcare providers or other providers of goods or services for a patient or individual.

The database 10H can also contain data, information, links, or hyperlinks, which can allow a healthcare provider to perform remote control or monitoring of healthcare devices or equipment used in the treatment of, a care of, or a monitoring of, a patient or individual, while the patient or individual is at home, in a hospital, in a nursing home, in a care facility, or traveling in or on, respectively, a car, automobile, train, subway train, boat, helicopter, airplane, aircraft, or any other vehicle. The database 10H can also contain data, information, a link(s), or a hyperlink(s) which can allow a healthcare provided to remotely control healthcare devices or equipment, instruments, surgical instruments, and/or any other devices which can be used in performing a procedure, a surgery, or a surgical procedure, on an individual or patient, and/or to administer a treatment to the individual or patient, via data, information, link(s), or a hyperlink(s), contained in the individual's or patient's electronic healthcare record.

The database 10H can also contain data and/or information regarding artificial limbs, artificial organs, implanted or implantable devices, and/or prosthetic devices, and/or dental implants, dental braces, and/or any other devices associated with an individual or patient. The data and/or information regarding artificial limbs, artificial organs, implanted or implantable devices, and/or prosthetic devices, and/or dental implants, dental braces, and/or any other devices associated with an individual or patient can include manufacturer information, model information, date put into use or installed, if applicable, maintenance instructions, provider who or which prescribed, installed, implanted, or fitted same, dates examined or checked, and/or any other data or information regarding same.

The database 10H can also contain data, information, or software, for performing healthcare audits, for performing meaningful use information processing routines, for identifying or selecting individuals for clinical trials, experimental procedures, experimental treatments, healthcare focus groups, healthcare surveys, or other activities or events, or for performing any other processing routines which can advantageously use any of the information stored in the database 10H, any information stored in any of the herein-described healthcare records, files, or histories, described herein, or any other information, stored by the apparatus 100 of the present invention or any of its computers, communication devices, component parts, or devices, or any other information stored in, provided by, generated by, or used by, the apparatus 100 of the present invention. For example, with regards to clinical trials, experimental procedures, experimental treatments, healthcare focus groups, healthcare surveys, or other activities or events, the database 10H can contain information regarding whether or not an individual or patient can or may be a candidate for, be eligible to participate in, has agreed to be candidate for, or has agreed to participate in, clinical trials, experimental procedures, experimental treatments, healthcare focus groups, healthcare surveys, or other activities or events, or has agreed to be candidate for, or has agreed to participate in, a particular clinical trial(s), experimental procedure(s), experimental treatment(s), healthcare focus group(s), healthcare survey(s), or other activities or events.

The database 10H can also contain any data and/or information needed or used to determine or measure the effectiveness of, or side effects experienced or associated with, any medication(s), medicine(s), drug(s), dietary supplement(s), supplement(s), vitamin(s), nutrient(s), over-the-counter product(s) or substance(s), or the effectiveness of a procedure(s), treatment(s), treatment plan(s), care management plan(s), or any other good(s) or service(s) which can be offered in the marketplace.

The database 10H can also contain data and/or information relating to information regarding health conditions, healthcare conditions, illnesses, diagnoses, symptoms, treatments, treatment plans, care management plans, care management practices, insurance information, information regarding type of insurance, wellness information, healthcare practices, healthcare history patterns, healthcare trends, treatment trends, care management trends, statistics, statistical analyses, studies, study trends, or any other healthcare or healthcare-related information, for or regarding any number or type of groups of individuals or patients, and any data or information for determining same. The database 10H can also contain data or information regarding, or for determining, any of the above-described information for any number of groups of individuals or patients based on sex, gender, age, occupation, education, ethnicity, nationality, country of origin, religion, or any demographic or demographics, or any other criteria. The database 10H can also contain data or information regarding, or for determining statistical information or probability information regarding, any of the herein-described information.

The database 10H can also contain data or information for implementing and for performing drug formulary checks or analyses, as well as data or information for performing medication, medicine, or drug, reconciliation.

The database 10H can also contain immunization data or information.

The database 10H can also contain educational or instructional information, links or hyperlinks to same, information regarding instructions or procedures, or links or hyperlinks to same, in order to allow for the providing of patient-specific educational or instructional information or resources to patients or individuals, as well as to any of the herein-described healthcare providers, other providers, payers or insurers, or intermediaries or caregivers.

The database 10H can also contain data or information necessary or desired for administering employee benefits for any of the individuals or patients who utilize the apparatus 100 and method of the present invention.

The database 10H can also contain data or information necessary or desired for purchasing or enrolling in employee benefits for any of the individuals or patients who utilize the apparatus 100 and method of the present invention.

The database 10H can also contain data or information necessary or desired for allowing any individual or patient to make a request or a claim for, or pursuant to, or to file a request or a claim for, an employee benefit or employee benefits, for any of the individuals or patients who utilize the apparatus 100 and method of the present invention.

The database 10H can also contain data or information for facilitating, or for providing for, the portability of healthcare insurance or health insurance benefits, life insurance or life insurance benefits, or disability insurance or disability insurance benefits, or for providing for the portability of any other employee benefit or employee benefits.

The database 10H can also contain any of the messages or reports described herein as being generated by or provided by the apparatus 100 and method of the present invention, for later use by any provider, insurer, payer, patient, individual, or intermediary, or any other person or entity, described herein as being able to utilize the apparatus 100 and method of the present invention.

The database 10H can also contain any data, information, or software, for performing any of the processing routines or functionality described herein as being capable of being performed by, or provided by, the apparatus 100 of the present invention.

The data and/or information which is contained and/or stored in the database 10H as well as any of the other databases 20H, 30H, 40, and 50H, described herein can be obtained from the various patients, individuals, providers, payers, and/or intermediaries, who or which utilize and/or who or which are serviced by the present invention. For example, the respective patients, providers, payers, intermediaries, and/or other users, could fill out questionnaires, forms, narratives, claim forms, and/or any other information medium, in written form, electronically, and/or otherwise.

Data and/or information stored in the database 10H as well as any of the other databases described herein can be updated by multiple parties. For example, a patient may provide a medical history for his or her individual file, his or her medical doctor can update the medical history information for the patient upon examining and/or treating him or her. The payer may also update the file with any associated payment or payment-related information. Should the patient go to another doctor or different type of doctor, all previous information would be available for, and can be updateable by, the next doctor.

The database 10H can also contain information regarding alternate medicine techniques, herbal techniques, meditation techniques, exercise techniques, self healing, faith healing, and/or other non-medicine treatments and/or techniques.

The database 10H can also include statistical data and/or information regarding diagnoses, and/or alternate diagnoses, treatment success, treatment failure, as well as statistical data and/or information regarding misdiagnoses. The database 10H also contains data and/or information regarding experimental treatments as well as statistical information regarding same, successes of same and failures of same.

The database 10H can also contain any other data and/or information, including software for performing any and all of the operations, routines, processing routines, and other functions and/or functionality described herein as being capable of being performed by the apparatus 100, the central processing computer(s) 10 and any of the herein-described provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90.

The database 10H can also contain any and/or all of the herein-described information for providing electronic veterinary healthcare records or filed (EVHRs) which can be used for maintaining healthcare records or file for any types or kinds f animals, high value animals, exotic animals, pet of any kind or type, or any other types or kinds of animals. For example, electronic veterinary healthcare records or files can be maintained and used for race horses, circus animals, animals used in shows, service animals, animals used for breeding, household pets, dogs, cats, fish, birds, mammals of any kind or types, birds of any kinds or types, and/or any other animal for which an owner, caregiver, or other responsible person or entity, may find it desirable or necessary to keep a healthcare record or file. In a preferred embodiment, the database 10H can also contain, any of the data and/or information, or any analogous data and/or information, described herein as being stored or contained in the database 10H, for any animal for which an electronic veterinary healthcare record or file is maintained.

It is important to note that the apparatus 100 and method of the present invention can be utilized, in any and or all of the embodiments described herein, in order to process and/or to provide veterinary healthcare information and/or veterinary healthcare-related information for and regarding any kind or type of animal or animals. In this regard, when used in veterinary applications, the terms "individual", "patient", "client", "user" or the like, or their plural forms, also refer to any of the herein-described animals or pets or any other animals or pets.

The database 10H can also contain any data and/or information, as well as any links or hyperlinks to any of the herein-described provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90 described herein as being used in connection with the present invention, and/or can contain data and/or information and/or links or hyperlinks to any data and/or information located or stored on, at, or in any of the provider communication device(s) 20, payer communication device(s) 30, user or patient communication device(s) 40, intermediary communication device(s) 50, healthcare records computer(s) 60, insurance exchange computer(s) 70, social networking computer(s) 80, and/or media computer(s) 90 described herein.

The database 10H can also contain information, links and/or hyperlinks, to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The database 10H can also contain data and/or information regarding any animals or pets associated with any individual, patient, or caregiver as well as any data and/or information regarding any electronic healthcare record for respective animal or pet.

The database 10H can also contain, for each or any of the herein-described individuals, patients, or caregiver, or for each provider or payer or insurer of a respective individual, patient, or caregiver, financial information regarding insurance premiums or payments, or premiums or payments for an insurer or payer policy, plan or program, which are or were made by or on behalf of the individual, patient, or caregiver, any and/or any insurance claim(s) or request(s) for payment(s) made by or on behalf of the individual, patient, or caregiver, provider bills or provider charges submitted in an insurance claim or a request for payment, provider amounts or provider charges billed for goods, products, or services, amounts paid by an insurer or payer for the amounts billed or charged by a provider, amounts paid or amounts of co-payments paid by or on behalf of the individual, patient, or caregiver, for the amounts billed, deductibles paid by or on behalf of the individual, patient or caregiver, and/or any other data and/or information regarding charges, bills, insurance claims, requests for payments, amounts paid by insurers or payers, and/or any amounts paid by or on behalf of the respective individual, patient, or caregiver.

The database 10H can also contain, for each individual, patient, or caregiver, any data and/or information regarding any vehicle(s) owned or operated by the individual, patient, or caregiver, along with data and/or information, and/or a link(s) or hyperlink(s) to any manufacturer of the vehicle or to any telematics, on-line service provider, or other services provider for the vehicle, such as for example, a telematics, on-line services provider, or other services provider who or which provides products and services such as those offered and provided in connection with automobiles and other motor vehicles as of the filing data of this application.

In any and/or all of the embodiments described herein, any of the data and/or information which is or which may be stored in the database 10H, and/or any of the other databases described herein, can be utilized and/or can appear in any of the reports, diagnostic reports, treatment reports, evaluation reports, provider reports, payer reports, patient reports, training reports, and/or any other reports, described herein.

The central processing computer 10 also includes an output device 10I for output any data, information, report, etc., described herein. In the preferred embodiment, the output device 10I can be a printer, a display, a transmitter, a modem, a speaker, and/or any other device which can be used to output data.

Any of the data and/or information for any of the patients, individuals, providers, payers, and/or intermediaries, can be updated by different parities and which such updated data and/or information being made available to other respective parties so as to provide and ensure comprehensive and up-to-date healthcare and healthcare-related information.

Figure 3:
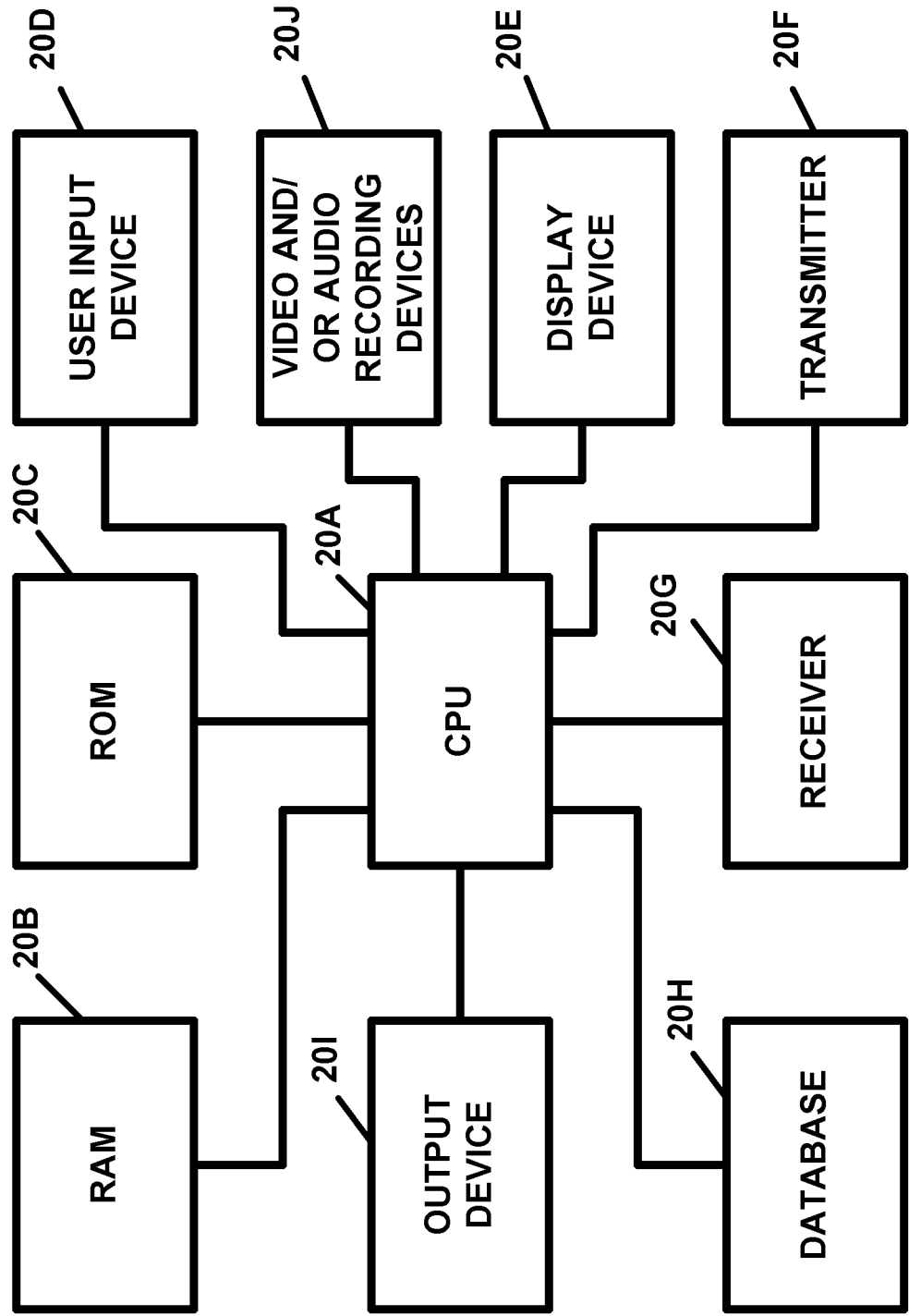
FIG. 3 illustrates the provider communication device of FIG. 1, in block diagram form.

FIG. 3 illustrates the provider communication device 20, in block diagram form. The provider communication device 20, in the preferred embodiment, can be personal computer, a network computer or computer system, or any other computer or communication device, which is utilized as a provider computer 20. In the preferred embodiment, the provider communication device 20 includes a central processing unit or CPU 20A, which in the preferred embodiment, is a microprocessor. The CPU 20A may also be a microcomputer, a minicomputer, a macro-computer, and/or a mainframe computer, depending upon the application.

The provider communication device 20 also includes a random access memory device(s) 20B (RAM) and a read only memory device(s) 20C (ROM), each of which is connected to the CPU 20A, a user input device 20D, for entering data and/or commands into the provider communication device 20, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, which an also include, for example, pulse rate monitors, blood pressure monitors, electrocardiograms, blood-sugars monitors, etc., if desired, or any other devices, measuring or measurement devices or equipment, or any other equipment used for obtaining information regarding an individual or patient, which input device(s) are also connected to the CPU 20A. In another preferred embodiment, the pulse rate monitors, blood pressure monitors, electrocardiograms, blood-sugars monitors, etc., if desired, or any other devices, measuring or measurement devices or equipment, or any other equipment used for obtaining information regarding an individual or patient, can also be integrated into the provider communication device 20.

The user input device 20D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 20D can be a keyboard for allowing a user to input information into the provider communication device and/or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 20D can also be, or can include, any one or more of, and/or any combination of, a thermometer, a digital thermometer, a stethoscope, a heart rate monitor or measurement device, a pulse rate monitor or measurement device, a blood pressure monitor or measurement device, a blood pressure measurement device, blood analysis device or machine, a respirator, a respiration monitoring or measurement device, a dialysis machine, a dialysis device, electrocardiograph (EKG) machine or device, electroencephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laprascopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, a PET scan device, an optical metabolism measurement or monitoring device, a radiotelemetric device, a doppler medical device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, microscopic camera probing device, any scope having a camera and/or a light, a laparoscopic device, a laparoscopic camera device, a camera used in or associated with equipment for performing visual probing of the body or any portions, parts, or organs, thereof, such as, but not limited to, a colonoscopy, an endoscopy, an esophagoscopy, a gastroscopy, or any devices used in laparoscopic surgery or other surgeries, an ingestible or implantable pill, capsule, or device, containing a camera and/or a light and equipment or circuitry for transmitting information as well as images to equipment inside or outside the body, and/or any other bio-metric or physiological data measuring device(s) and/or data acquisition device (hereinafter referred to generally or collectively as "healthcare equipment input device", "healthcare measurement input device", or "healthcare monitoring input device").

The user input device 20D can also be, or can include, a pacemaker, a device for monitoring blood pressure or blood flow, or an ingestible or implantable pill, capsule, or device, containing a camera and/or a light and equipment or circuitry for transmitting information as well as images to equipment inside or outside the body.

The user input device 20D can also be, or can include, a global positioning device which an be utilized for determining a position or location of the provider communication device 20 and/or the provider who or which is using the same.

The provider communication device 20 also includes a display device 20E for displaying data and/or information to a user or operator.

The provider communication device 20 also includes a transmitter(s) 20F, for transmitting signals and/or data and/or information to any one or more of the central processing computer(s) 10, any other provider communication device(s) 20, the communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention. The provider communication device 20 also includes a receiver 20G, for receiving signals and/or data and/or information from any one or more of the central processing computer(s) 10, any other provider communication device(s) 20, the payer communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The provider communication device 20 also includes a database(s) 20H. The database 20H can contain and/or be linked to any of the data and/or information described herein as being stored in the database 10H.

The provider communication device 20 also includes an output device 20I for output any data, information, report, etc., described herein. In the preferred embodiment, the output device 20I can be a printer, a display, a transmitter, a modem, a speaker, and/or any other device which can be used to output data.

The provider communication device 20 also includes a video and/or audio recording device(s) 20J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 4:
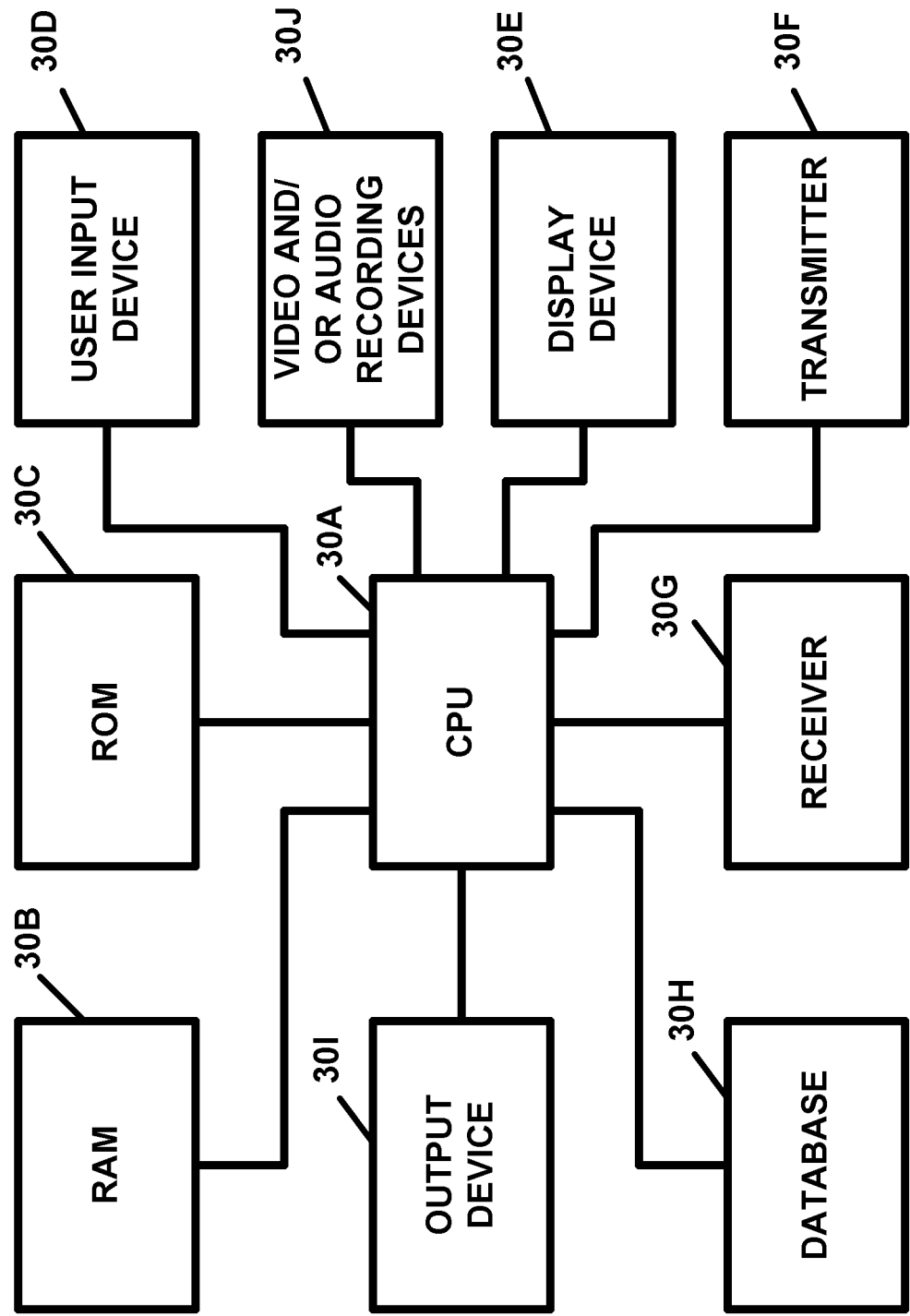
FIG. 4 illustrates the insurer or payer communication device of FIG. 1, in block diagram form.

FIG. 4 illustrates the payer communication device 30, in block diagram form. The payer communication device 30, in the preferred embodiment, can be personal computer, a network computer or computer system, or any other computer or communication device, which is utilized as a payer computer 30. In the preferred embodiment, the payer communication device 30 includes a central processing unit or CPU 30A, which in the preferred embodiment, is a microprocessor. The CPU 30A may also be a microcomputer, a minicomputer, a macro-computer, and/or a mainframe computer, depending upon the application.

The payer communication device 30 also includes a random access memory device(s) 30B (RAM) and a read only memory device(s) 30C (ROM), each of which is connected to the CPU 30A, a user input device 30D, for entering data and/or commands into the payer communication device 30, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electro-cardiograms, blood-sugars monitors, etc., if desired, which input device(s) are also connected to the CPU 30A. The payer communication device 30 also includes a display device 30E for displaying data and/or information to a user or operator.

The payer communication device 30 also includes a transmitter(s) 30F, for transmitting signals and/or data and/or information to any one or more of the central processing computer(s) 10, the provider communication device(s) 20, any other payer communication device(s) 30, the user or patient communication device(s) 40, and the intermediary computer(s) 50, the healthcare records computer(s) 60, the insurance exchange computer(s) 70, the social networking computer(s) 80, and/or the media computer(s) 90 described herein, which may be utilized in conjunction with the present invention. The payer communication device 30 also includes a receiver 30G, for receiving signals and/or data and/or information from any one or more of the central processing computer(s) 10, the provider communication device(s) 20, any other payer communication device(s) 30, the user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The payer communication device 30 also includes a database(s) 30H. The database 30H can contain and/or be linked to any of the data and/or information described herein as being stored in the database 10H.

The payer communication device 30 also includes an output device 30I for output any data, information, report, etc., described herein. In the preferred embodiment, the output device 30I can be a printer, a display, a transmitter, a modem, a speaker, and/or any other device which can be used to output data.

The payer communication device 30 also includes a video and/or audio recording device(s) 30J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 5:
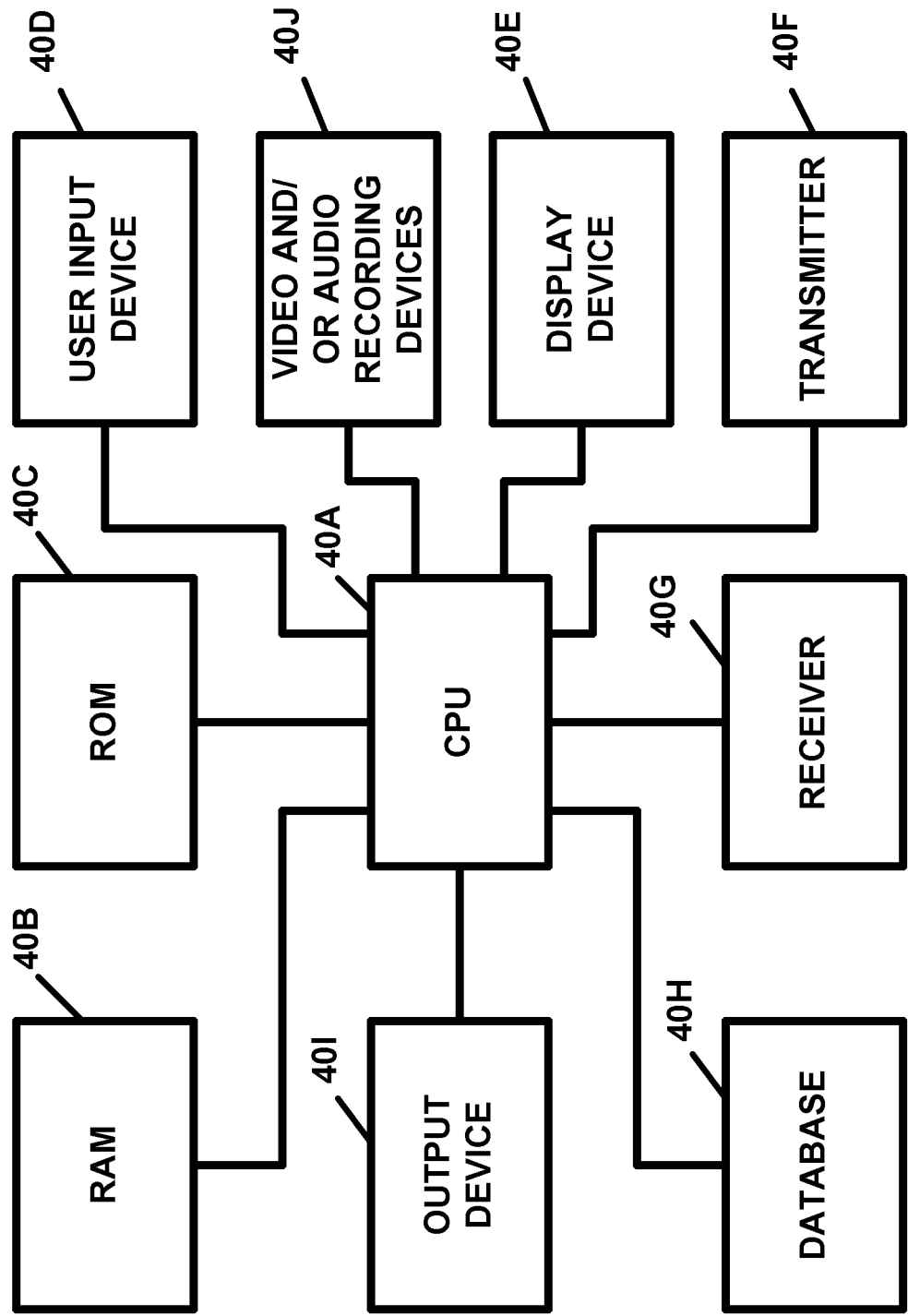
FIG. 5 illustrates the user or patient communication device of FIG. 1, in block diagram form.

FIG. 5 illustrates the user or patient communication device 40, in block diagram form. The user or patient communication device 40, in the preferred embodiment, can be personal computer, a network computer or computer system, or any other computer or communication device, which is utilized as a patient computer. In the preferred embodiment, the user or patient communication device 40 includes a central processing unit or CPU 40A, which in the preferred embodiment, is a microprocessor. The CPU 40A may also be a microcomputer, a minicomputer, a macro-computer, and/or a mainframe computer, depending upon the application.

The user or patient communication device 40 also includes a random access memory device(s) 40B (RAM) and a read only memory device(s) 40C (ROM), each of which is connected to the CPU 40A, a user input device 40D, for entering data and/or commands into the user or patient communication device 40, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electro-cardiograms, blood-sugars monitors, etc., if desired, which input device(s) are also connected to the CPU 40A.

The user input device 40D can also acquire, receive, generate and/or provide, data which can be entered by a user or individual and/or can be a device which can acquire, receive, generate and/or provide, digital data such as medical, healthcare, bio-metric, physiological, and/or any other kind of healthcare data and/or healthcare-related data. For example, a user input device 40D can be a keyboard for allowing a user to input information into the patient communication device and/or a user input device can, for example, by a heart rate monitor or EKG machine which can receive information from a patient or individual and generate a digital signal, digital data, analog data, and/or any other signal, data, and/or information, which is representative of the patient's or individual's heart rate, pulse rate, and/or cardiac activity.

The user input device 40D can also be, or can include, or the user or patient communication device 40 can include, any one or more of, and/or any combination of, a thermometer, a digital thermometer, a stethoscope, a heart rate monitor or measurement device, a pulse rate monitor or measurement device, a blood pressure monitor or measurement device, a blood pressure measurement device, a blood analysis device or machine, a respirator, a respiration monitoring or measurement device, a dialysis machine, a dialysis device, electrocardiograph (EKG) machine or device, electrocephalograph (EEG) machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laprascopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedence measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, microscopic camera probing device, and/or any other bio-metric or physiological data measuring device(s) and/or data acquisition device data acquisition device (hereinafter referred to generally or collectively as "healthcare equipment input device", "healthcare measurement input device", or "healthcare monitoring input device").

The user input device 40D can also be, or can include, a global positioning device which an be utilized for determining a position or location of the user or patient communication device 40 and/or the user or operator of the same and/or any individual or healthcare patient or client who uses the same.

The user or patient communication device 40 also includes a display device 40E for displaying data and/or information to a user or operator.

The user or patient communication device 40 also includes a transmitter(s) 40F, for transmitting signals and/or data and/or information to any one or more of the central processing computer(s) 10, the provider communication device(s) 20, the payer communication device(s) 30, any other user or patient communication device(s) 40, and the intermediary computer(s) 50, the healthcare records computer(s) 60, the insurance exchange computer(s) 70, the social networking computer(s) 80, and/or the media computer(s) 90 described herein, which may be utilized in conjunction with the present invention. The user or patient communication device 40 also includes a receiver 40G, for receiving signals and/or data and/or information from any one or more of the central processing computer(s) 10, the provider communication device(s) 20, the payer communication device(s) 30, any other user or patient communication device(s) 40, the intermediary computer(s) 50, the healthcare records computer(s) 60, the insurance exchange computer(s) 70, the social networking computer(s) 80, and/or the media computer(s) 90 described herein, which may be utilized in conjunction with the present invention.

The user or patient communication device 40 also includes a database(s) 40H. The database 40H can contain and/or be linked to any of the data and/or information described herein as being stored in the database 10H.

The user or patient communication device 40 also includes an output device 40I for output any data, information, report, etc., described herein. In the preferred embodiment, the output device 40I can be a printer, a display, a transmitter, a modem, a speaker, and/or any other device which can be used to output data.

The user or patient communication device 40 also includes a video and/or audio recording device(s) 40J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

Figure 6:
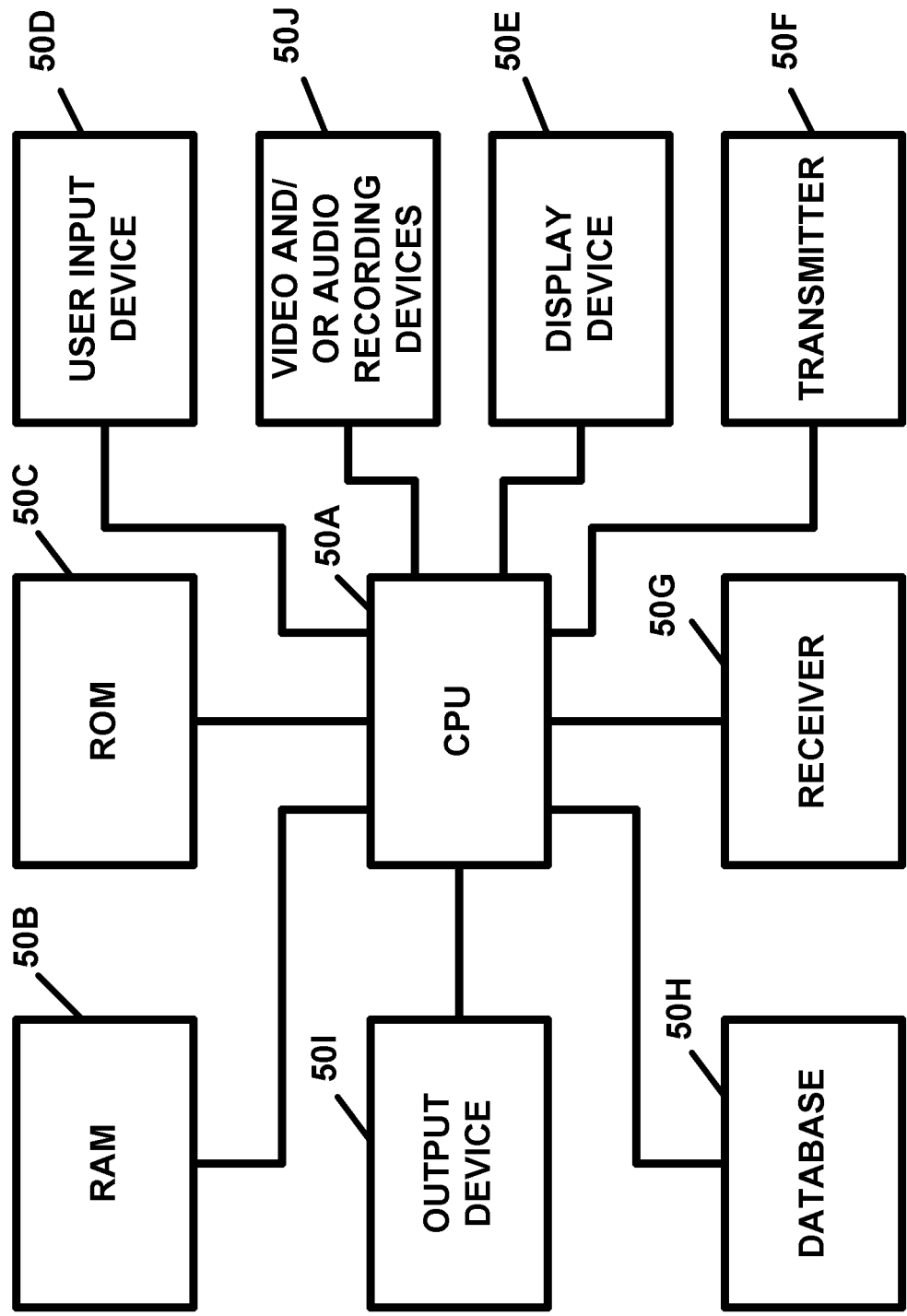
FIG. 6 illustrates the intermediary communication device of FIG. 1, in block diagram form.

FIG. 6 illustrates the intermediary computer 50, in block diagram form. The intermediary computer 50, in the preferred embodiment, can be personal computer, a network computer or computer system, or any other computer or communication device, which is utilized as an intermediary computer 50. In the preferred embodiment, the intermediary computer 50 includes a central processing unit or CPU 50A, which in the preferred embodiment, is a microprocessor. The CPU 50A may also be a microcomputer, a minicomputer, a macro-computer, and/or a mainframe computer, depending upon the application.

The intermediary computer 50 also includes a random access memory device(s) 50B (RAM) and a read only memory device(s) 50C (ROM), each of which is connected to the CPU 50A, a user input device 50D, for entering data and/or commands into the intermediary computer 50, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information, for example pulse rate monitors, blood pressure monitors, electrocardiograms, blood-sugars monitors, etc., if desired, which input device(s) are also connected to the CPU 50A. The intermediary computer 50 also includes a display device 50E for displaying data and/or information to a user or operator.

The intermediary computer 50 also includes a transmitter(s) 50F, for transmitting signals and/or data and/or information to any one or more of the central processing computer(s) 10, the provider communication device(s) 20, the payer communication device(s) 30, the user or patient communication device(s) 40, any other intermediary computer(s) 50, the healthcare records computer(s) 60, the insurance exchange computer(s) 70, the social networking computer(s) 80, and/or the media computer(s) 90 described herein, which may be utilized in conjunction with the present invention. The intermediary computer 50 also includes a receiver 50G, for receiving signals and/or data and/or information from any one or more of the central processing computer(s) 10, the provider communication device(s) 20, the payer communication device(s) 30, the user or patient communication device(s) 40, any other intermediary computer(s) 50, the healthcare records computer(s) 60, the insurance exchange computer(s) 70, the social networking computer(s) 80, and/or the media computer(s) 90 described herein, which may be utilized in conjunction with the present invention. which may be utilized in conjunction with the present invention.

The intermediary computer 50 also includes a database(s) 50H. The database 50H can contain and/or be linked to any of the data and/or information described herein as being stored in the database 10H.

The intermediary communication device 50 also includes an output device 50I for output any data, information, report, etc., described herein. In the preferred embodiment, the output device 50I can be a printer, a display, a transmitter, a modem, a speaker, and/or any other device which can be used to output data.

The intermediary communication device 50 also includes a video and/or audio recording device(s) 50J which can include a camera and/or a video recording device for recording pictures or video and/or video clips and/or a microphone or an audio recording device for recording audio or audio clips which can be stored in any of the electronic healthcare, electronic medical, electronic dental, electronic pharmacy, and/or electronic behavioral healthcare, records or files described herein, and/or which can be otherwise used for communicating with other users, individuals, patients, providers, payers, or persons or entities who or which utilize the apparatus 100 and method of the present invention.

In any and/or all of the embodiments described herein, any one of the central processing computers 10, the provider communication devices 20, the payer communication devices 30, the patient communication devices 40, and/or the intermediary communication devices 50, can include input devices (not shown) for facilitating the data entry of a patients vital signs and or other medical data such as, but not limited to, pulse rate, blood pressure, blood-sugar level, etc., and any other data and or information which can be input into the respective computer and/or communication device and be transmitted to the central processing computer consistent with the utilization of the present invention as described herein.

Figure 7:
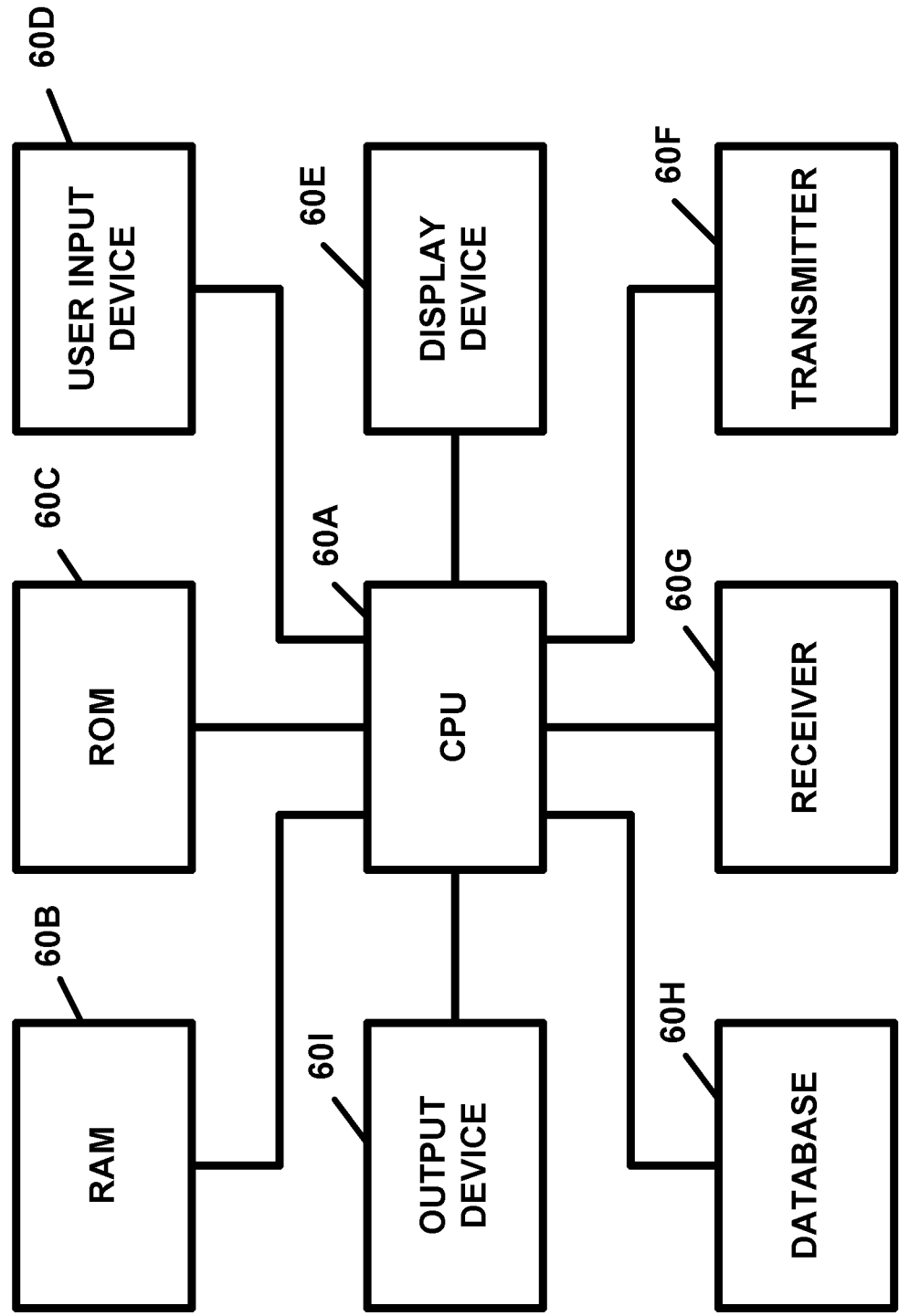
FIG. 7 illustrates an exemplary healthcare records cloud system computer of FIG. 1, in block diagram form.

FIG. 7 illustrates the healthcare records computer 60, in block diagram form. The healthcare records computer 60, in the preferred embodiment, can be server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to store an electronic healthcare record, an electronic medical record, an electronic dental record, an electronic pharmacy record, or an electronic behavioral healthcare record or any one or any number of electronic healthcare records, electronic medical records, electronic dental records, electronic pharmacy records, and/or electronic behavioral healthcare records. In a preferred embodiment, the healthcare records computer 60 can be any computer or computer system for storing any an electronic healthcare record, an electronic medical record, an electronic dental record, an electronic pharmacy record, or an electronic behavioral healthcare record which is store somewhere else other than the central processing computer. The healthcare records computer 60 can be used by, maintained by, or associated with any individual, provider, user, patient, payer, intermediary, or any other entity or third party.

In the preferred embodiment, the healthcare records computer 60 includes a central processing unit or CPU 60A, which in the preferred embodiment, is a microprocessor. The CPU 60A may also be a microcomputer, a minicomputer, a macro-computer, and/or a mainframe computer, depending upon the application.

The healthcare records computer 60 also includes a random access memory device(s) 60B (RAM) and a read only memory device(s) 60C (ROM), each of which is connected to the CPU 60A, a user input device 60D, for entering data and/or commands into the healthcare records computer 60, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering healthcare data and/or information which input device(s) are also connected to the CPU 60A. The healthcare records computer 60 also includes a display device 60E for displaying data and/or information to a user or operator.

The healthcare records computer 60 also includes a transmitter(s) 60F, for transmitting signals and/or data and/or information to any one or more of the central processing computer(s) 10, the provider communication device(s) 20, the payer computers(s) 30, the user or patient communication device(s) 40, and the intermediary computer(s) 50, any other healthcare records computer(s) 60, the insurance exchange computer(s) 70, the social networking computer(s) 80, and/or the media computer(s) 90 described herein, which may be utilized in conjunction with the present invention. The healthcare records computer 60 also includes a receiver 60G, for receiving signals and/or data and/or information from any one or more of the central processing computer(s) 10, the provider communication device(s) 20, the payer computers(s) 30, the user or patient communication device(s) 40, the intermediary computer(s) 50, any other healthcare records computer(s) 60, the insurance exchange computer(s) 70, the social networking computer(s) 80, and/or the media computer(s) 90 described herein, which may be utilized in conjunction with the present invention.

The healthcare records computer 60 also includes a database(s) 60H. The database 60H can contain and/or be linked to any of the data and/or information described herein as being stored in the database 10H and can also contain any data and/or information regarding and including any of the of electronic healthcare records, electronic medical records, electronic dental records, electronic pharmacy records, and/or electronic behavioral healthcare records which are stored in the healthcare records computer 60.

The healthcare records computer 60 also includes an output device 60I for output any data, information, report, etc., described herein. In the preferred embodiment, the output device 60I can be a printer, a display, a transmitter, a modem, a speaker, and/or any other device which can be used to output data.

Figure 8:
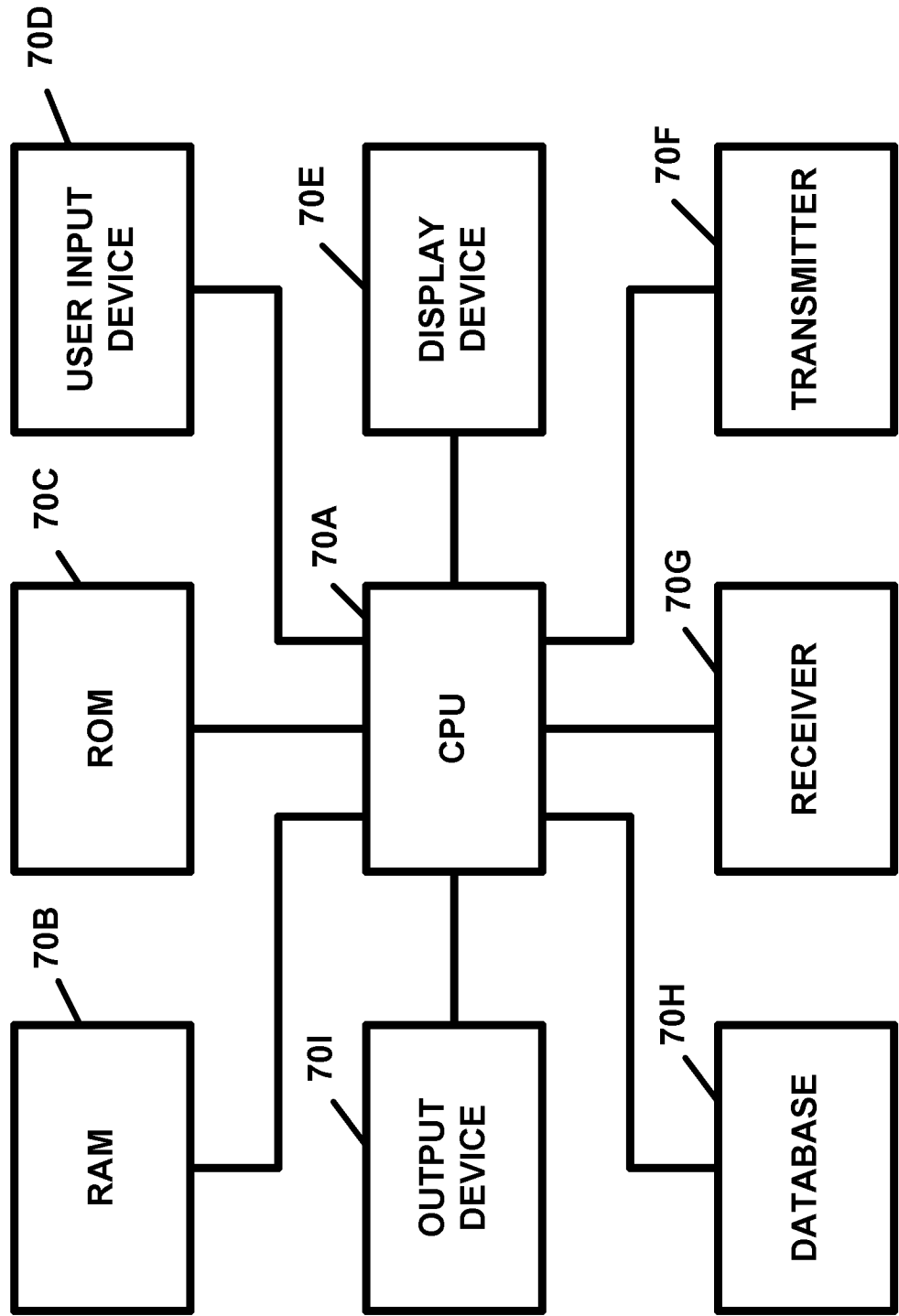
FIG. 8 illustrates the an exemplary insurance exchange computer of FIG. 1, in block diagram form.

FIG. 8 illustrates the insurance exchange computer 70, in block diagram form. The insurance exchange computer 70, in the preferred embodiment, can be server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to function as an insurance exchange computer 70. In a preferred embodiment, the insurance exchange computer 70 can be any computer or computer system for providing the functionality described herein as being provided by the insurance exchange computer 70.

The insurance exchange computer 70 can be used by, maintained by, or associated with any provider of any of the herein-described insurance policies, products, or services, described herein as being provided via the apparatus 100 and method of the present invention.

In the preferred embodiment, the insurance exchange computer 70 includes a central processing unit or CPU 70A, which in the preferred embodiment, is a microprocessor. The CPU 70A may also be a microcomputer, a minicomputer, a macro-computer, and/or a mainframe computer, depending upon the application.

The insurance exchange computer 70 also includes a random access memory device(s) 70B (RAM) and a read only memory device(s) 70C (ROM), each of which is connected to the CPU 70A, a user input device 70D, for entering data and/or commands into the insurance exchange computer 70, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 70A. The insurance exchange computer 70 also includes a display device 70E for displaying data and/or information to a user or operator.

The insurance exchange computer 70 also includes a transmitter(s) 70F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, any other insurance exchange computer(s) 70, the social networking computer(s) 80, and/or the media computer(s) 90 described herein, which may be utilized in conjunction with the present invention. The insurance exchange computer 70 also includes a receiver 70G, for receiving signals and/or data and/or information from any one or more of the central processing computer(s) 10, the provider communication device(s) 20, the payer communication device(s) 30, the user or patient communication device(s) 40, the intermediary computer(s) 50, the healthcare records computer(s) 60, any other insurance exchange computer(s) 70, the social networking computer(s) 80, and/or the media computer(s) 90 described herein, which may be utilized in conjunction with the present invention.

The insurance exchange computer 70 also includes a database(s) 70H. The database 70H can contain and/or be linked to any of the data and/or information described herein as being stored in the database 10H and can also contain any data and/or information regarding and including any of the various insurance policies, products, or service, which can be offered for sale by the insurance exchange computer 70, as well as any data and/or information regarding insured individuals or entities, their insurance policies, products, and/or services, claims made, claims paid, and any other records typically stored or maintained by an insurance company computer, an insurance exchange computer, an electronic commerce computer or any other data and/or information for providing any of the functions or functionality described herein as being performed by the insurance exchange computer 70.

The insurance exchange computer 70 also includes an output device 70I for output any data, information, report, etc., described herein. In the preferred embodiment, the output device 70I can be a printer, a display, a transmitter, a modem, a speaker, and/or any other device which can be used to output data.

Figure 9:
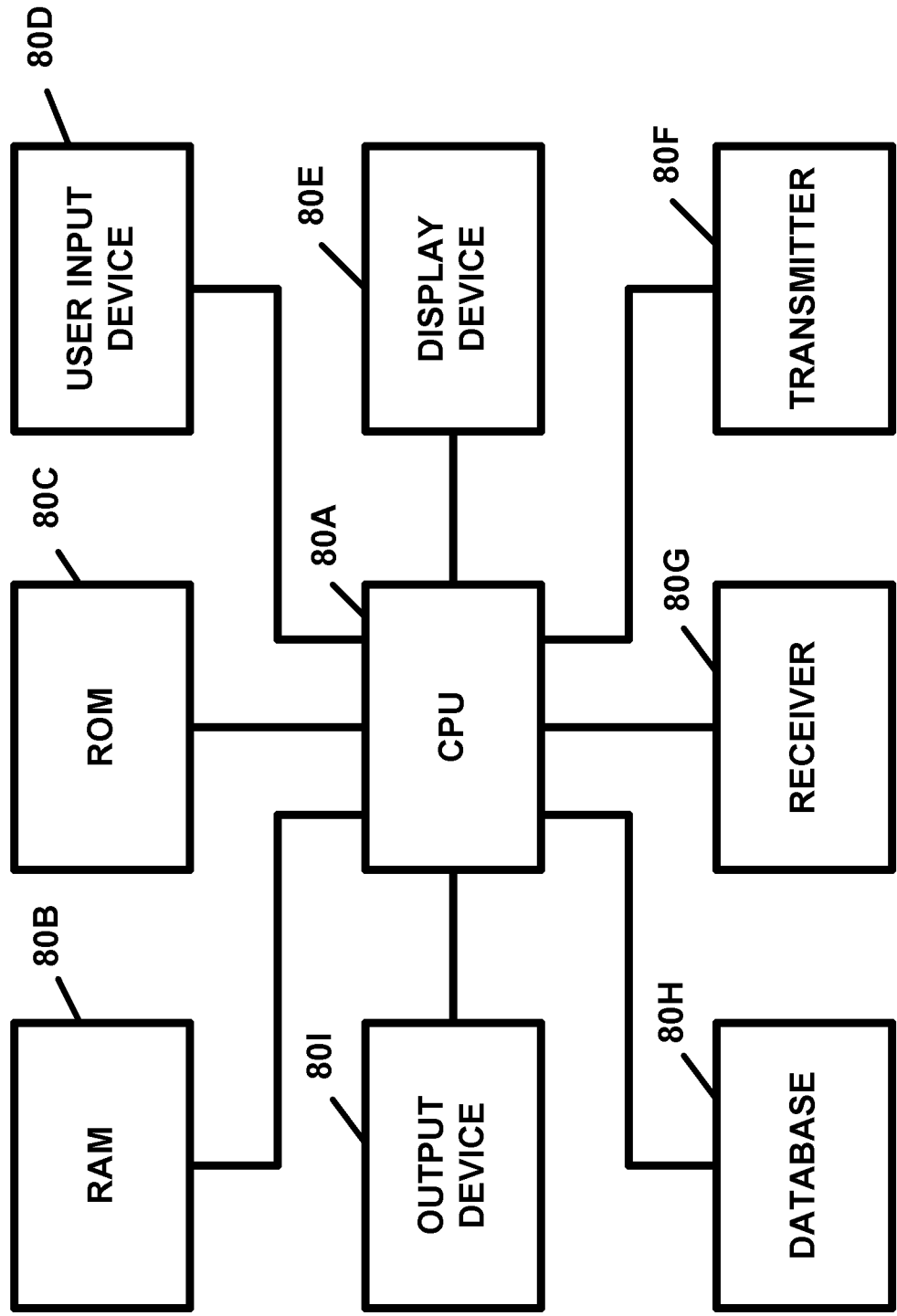
FIG. 9 illustrates an exemplary social networking computer of FIG. 1, in block diagram form.

FIG. 9 illustrates the social networking computer 80, in block diagram form. The social networking computer 80, in the preferred embodiment, can be any social networking computer or computer system or any computer or computer system used by or associated with any social networking company or social networking website, or can be any suitable server computer or server computer system, a cloud computer or cloud computer system, a network computer or computer system, a personal computer or any other computer or communication device, or any cellular telephone, tablet, personal digital assistant, wireless communication device or wireless computer, a watch, or any other communication device, which is utilized to function as a social networking computer 80. In a preferred embodiment, the social networking computer 80 can be any computer of computer system for providing the functionality described herein as being provided by the social networking computer 80 or any social networking computer or website.

The social networking computer 80 can be used by, maintained by, or associated with social networking company, website, or other entity and can provide any of the herein-described social networking information, activities, and/or functionality, described herein as being provided via the apparatus 100 and method of the present invention and which can be provided by any social networking company, website, or other entity.

In the preferred embodiment, the social networking computer 80 includes a central processing unit or CPU 80A, which in the preferred embodiment, is a microprocessor. The CPU 80A may also be a microcomputer, a minicomputer, a macro-computer, and/or a mainframe computer, depending upon the application.

The social networking computer 80 also includes a random access memory device(s) 80B (RAM) and a read only memory device(s) 80C (ROM), each of which is connected to the CPU 80A, a user input device 80D, for entering data and/or commands into the social networking computer 80, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 80A. The social networking computer 80 also includes a display device 80E for displaying data and/or information to a user or operator.

The social networking computer 80 also includes a transmitter(s) 80F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, the insurance exchange computer(s) 70, any other social networking computer(s) 80, and/or the media computer(s) 90 described herein, which may be utilized in conjunction with the present invention. The social networking computer 80 also includes a receiver 80G, for receiving signals and/or data and/or information from any one or more of the central processing computer(s) 10, the provider communication device(s) 20, the payer communication device(s) 30, the user or patient communication device(s) 40 the intermediary computer(s) 50, the healthcare records computer(s) 60, the insurance exchange computer(s) 70, any other social networking computer(s) 80, and/or the media computer(s) 90 described herein, which may be utilized in conjunction with the present invention.

The social networking computer 80 also includes a database(s) 80H. The database 80H can contain and/or be linked to any of the data and/or information described herein as being stored in the database 10H and can also contain any data and/or information typically found in or utilized by a social networking computer or any members of the social network serviced thereby as well as any data and/or information typically utilized in providing or performing the functionality and/or services provided or offered by the social network associated with the social networking computer 80.

The social networking computer 80 also includes an output device 80I for output any data, information, report, etc., described herein. In the preferred embodiment, the output device 80I can be a printer, a display, a transmitter, a modem, a speaker, and/or any other device which can be used to output data.

Figure 10:
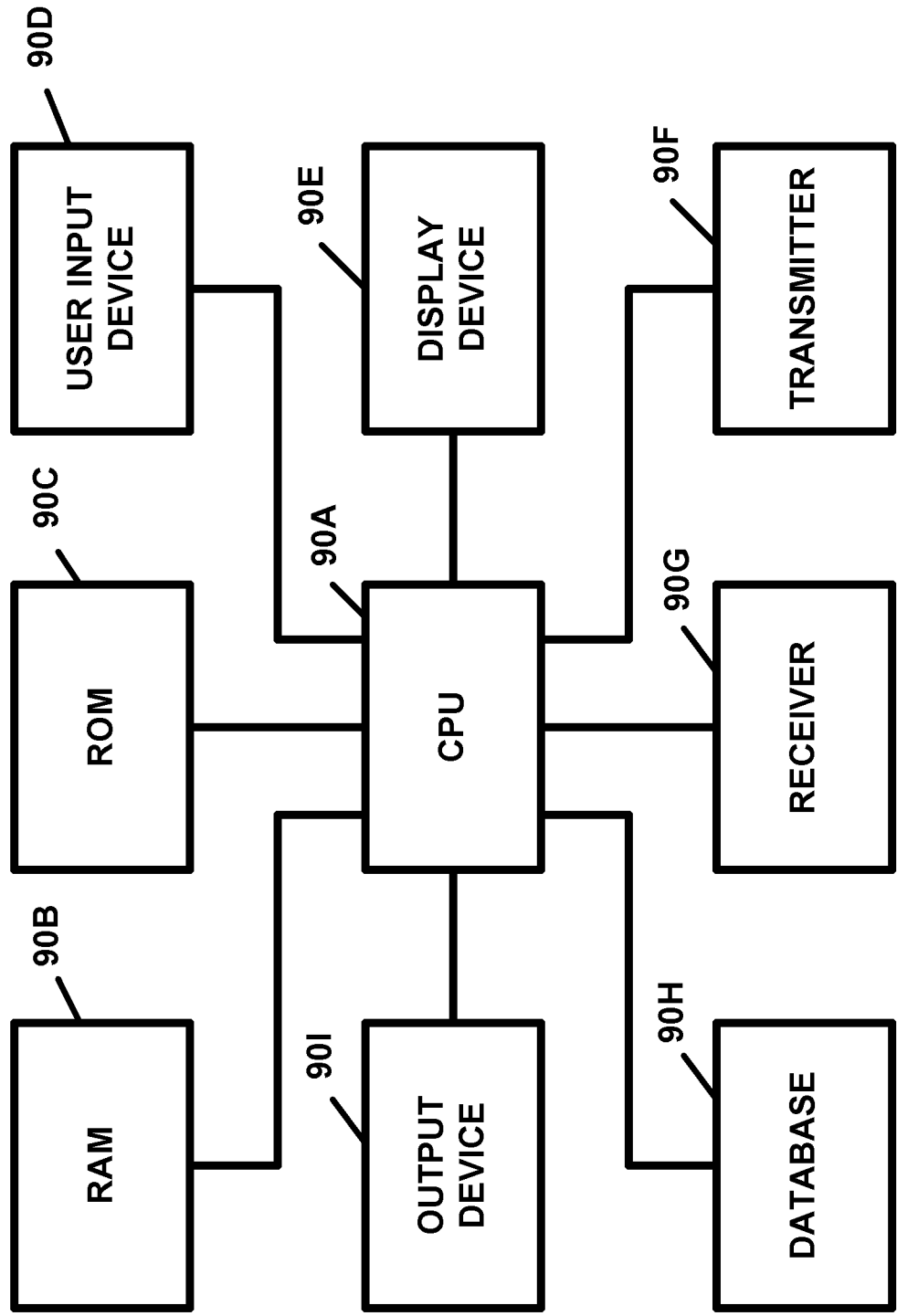
FIG. 10 illustrates an exemplary media computer of FIG. 1, in block diagram form.

FIG. 10 illustrates the media computer 90, in block diagram form. The media computer 90, in the preferred embodiment, can be any computer or computer system used by or associated with any news information source, individual, company, or entity, any external information source, individual, company, or entity, any advertiser or advertisement source, individual, company or entity, or any marketing materials source, individual, company, or entity.

The media computer 90 can be any computer or computer system which can provide, to any of the herein-described users, individuals, patients, providers, payers, intermediaries, third parties, and/or entities who or which utilized the apparatus 100 and method of the present invention, any news, information, advertisements, or marketing materials, of any kind, nature, or type, which can include, but which is not limited to, any healthcare or healthcare-related news, information, advertisements, or marketing materials, any fitness or fitness-related news, information, advertisements, or marketing materials, any wellness or wellness-related news, information, advertisements, or marketing materials, as well as any non-healthcare or non-healthcare-related news, information, advertisements, or marketing materials. The media computer 90 provides news, information, advertisements, or marketing materials, via the apparatus 100 and method of the present invention. In a preferred embodiment, the media computer 90 can be any computer or computer system for providing the functionality described herein as being provided by the media computer 90.

The media computer 90 can be used by, maintained by, or associated with a media company or entity, a news service, information source or service, an advertiser, an advertisement company, agency, or entity, a marketer, a marketing company or entity, or any individual providing a media, news, information, advertisements, or marketing materials of or on behalf of themselves or another, The media computer 90 can provide any of the herein-described media, news, information, advertisements, or marketing materials, and/or any other information and/or can provide any o the functionality described herein as being provided via the apparatus 100 and method of the present invention.

In the preferred embodiment, the media computer 90 includes a central processing unit or CPU 90A, which in the preferred embodiment, is a microprocessor. The CPU 90A may also be a microcomputer, a minicomputer, a macrocomputer, and/or a mainframe computer, depending upon the application.

The media computer 90 also includes a random access memory device(s) 90B (RAM) and a read only memory device(s) 90C (ROM), each of which is connected to the CPU 90A, a user input device 90D, for entering data and/or commands into the media computer 90, which includes any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information which input device(s) are also connected to the CPU 90A. The media computer 90 also includes a display device 90E for displaying data and/or information to a user or operator.

The media computer 90 also includes a transmitter(s) 90F, for transmitting signals and/or data and/or information to any one or more of the central processing computer(s) 10, the provider communication device(s) 20, the payer communication device(s) 30, the user or patient communication device(s) 40, and the intermediary computer(s) 50, the healthcare records computer(s) 60, the insurance exchange computer(s) 70, the social networking computer(s) 80, and/or any other media computer(s) 90 described herein, which may be utilized in conjunction with the present invention. The media computer 90 also includes a receiver 90G, for receiving signals and/or data and/or information from any one or more of the central processing computer(s) 10, the provider communication device(s) 20, the payer communication device(s) 30, the user or patient communication device(s) 40 the intermediary computer(s) 50, the healthcare records computer(s) 60, the insurance exchange computer(s) 70, the social networking computer(s) 80, and/or any other media computer(s) 90 described herein, which may be utilized in conjunction with the present invention.

The media computer 90 also includes a database(s) 90H. The database 90H can contain and/or be linked to any of the data and/or information described herein as being stored in the database 10H and can also contain any data and/or information typically found in or utilized by a media computer as well as any of the respective media, news, information, advertisements, or marketing materials, and/or any data and/or information typically utilized in providing or performing the functionality and/or services provided or offered by the media computer 90.

The media computer 90 also includes an output device 90I for output any data, information, report, etc., described herein. In the preferred embodiment, the output device 90I can be a printer, a display, a transmitter, a modem, a speaker, and/or any other device which can be used to output data.

The apparatus and method of the present invention can be utilized in numerous preferred embodiments in order to provide a vast array of healthcare and healthcare-related services for any one or more of the various parties described herein. While certain of the preferred embodiments may be described with regards to utilization by a particular party, it is important to note that any individual, patient, user, provider, payer, and/or intermediary or third party, may utilize the present invention in the same, similar and/or analogous manner. For example, a preferred embodiment for determining and/or ascertaining a medical diagnosis can be described as being utilized by a treating physician as well as be utilized by a provider to verify and/or check a diagnosis as well as by a patient or other user or individual in order to perform a self-diagnosis or double check a doctors diagnosis. In the same manner, any other preferred embodiment and/or other uses of the present invention can be utilized by any of the parties described herein.

The apparatus 100 of the present invention can also be utilized in order to allow an individual or a patient, or a caregiver, or one responsible for the care of an individual or patient, to enter notes, comments, or messages regarding or relating to the individual or patient into one or more of any of the individual's, patient's, or caregiver's, electronic healthcare record(s), electronic healthcare file(s), electronic medical record(s), electronic dental record(s), electronic pharmacy record(s), and/or electronic behavioral healthcare record(s). Any respective note, comment, or message can be in text form, audio form, or video form, and can contain information regarding a symptom, an illness, an experience, a treatment, a diagnosis, a treatment plan, an activity, a problem, a concern, a thought or an idea, a question, a question for a healthcare provider, or any other information which the individual or patient, or one caring for the individual or patient, may deem important to be recorded or noted in the respective electronic healthcare record(s), electronic medical record(s), electronic dental record(s), electronic pharmacy record(s), and/or electronic behavioral healthcare record(s), or which can be communicated to, or otherwise made available to, a provider or an insurer or payer.

A healthcare provider can access, obtain, and/or use, the information provided or contained in the note, comment, or message, or provided or contained in multiple notes, comments, or messages, for any suitable purpose, such as, but not limited to, for preparing for, or for use during, a remote or virtual office visit with, or a remote or distance examination of, an individual, a patient, or a caregiver for or an individual or a patient, during a video telephone call, a video chat session, or a videoconference, with the individual, the patient, or the caregiver for or the individual or the patient, or for use during a conversation, discussion, or consultation, during a video telephone call, a video chat session, or a videoconference, with the individual, the patient, or the caregiver for the individual or the patient, or for use during a conversation, discussion, or consultation, during a video telephone call, a video chat session, or a videoconference, with and between, the healthcare provider, and the individual, the patient, or the caregiver for or the individual or the patient, or another healthcare provider or any other provider, or an insurer or a payer, or an intermediary, or for use during reviewing, updating, modifying, or performing any other activity in connection with, an individual's or patient's healthcare records, files, or histories, for use while making a diagnosis, for use while formulating a treatment or a treatment plan, for use in reviewing or evaluating an individual's or patient's diagnosis or treatment, for use in treatment planning and/or the evaluating of same, for use in care management, for use in monitoring or evaluating a recovery, for use in providing continuing or on-going care or treatment, for use in connection with the providing of a remote healthcare services or tele-health services, and/or for any other suitable use or purpose.

Any notes, comments or messages, can be provided by the individual, patient, or caregiver, or by any person caring for the individual or patient, while making an appointment, in advance of a video telephone call, a video chat session, or a videoconference, or a remote or virtual office visit with, or a remote or distance examination of, or in advance of a video telephone call, a video chat session, or a videoconference, or a remote or distance examination of, with the individual, the patient, or the caregiver for the individual or the patient, or a video telephone call, a video chat session, or a videoconference, with another provider, or a payer or insurer or any third party or intermediary, in connection with any tele-health related activity, or for the purpose of making and entering a note, comment, or message, into the individual's or patient's respective electronic healthcare record(s), electronic medical record(s), electronic dental record(s), electronic pharmacy record(s), and/or electronic behavioral healthcare record(s). In this regard, the present invention can allow an individual or patient, or a caregiver, or one responsible for caring for the individual or patient, to make and enter any notes, comments, or messages, into the individual's or patient's respective electronic healthcare record(s), electronic medical record(s), electronic dental record(s), electronic pharmacy record(s), and/or electronic behavioral healthcare record(s) so as to facilitate accurate and complete healthcare information record keeping.

The apparatus 100 of the present invention can be utilized to provide healthcare services, such as, but not limited to, a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 100 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 100 and method of the present invention can also be utilized to facilitate remote or virtual provider visits, consultations, and/or examinations, via and/or through the use of video calls, video chat sessions, and/or videoconferences, with and between an individual, a patient, and/or a caregiver for the individual or the patient, and a healthcare provider. The apparatus 100 and method of the present invention can also be utilized to facilitate remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

The apparatus 100 of the present invention can be utilized to provide healthcare services, such as, but not limited to a consultation with a healthcare provider, a discussion with a healthcare provider, a remote or virtual office visit with a healthcare provider, a healthcare examination by a healthcare provider, remotely or virtually via a video telephone call, a video chat session, or a videoconference, with and between an individual, a patient, or a caregiver for or an individual or a patient, and a healthcare provider. The apparatus 100 of the present invention can also be utilized to provide healthcare services, such as, but not limited to a consultation with a healthcare insurer, a healthcare payer, or an intermediary or a discussion with a healthcare insurer, a healthcare payer, or an intermediary, remotely or virtually via a video telephone call, a video chat session, or a videoconference, with and between an individual, a patient, or a caregiver for or an individual or a patient, and a healthcare insurer or a healthcare payer or an intermediary.

The apparatus 100 of the present invention can also be utilized to provide a healthcare provider with access to the individual's or the patient's healthcare records, files, or history, before or during a video call, a video chat session, or a videoconference, before, in or during, and/or after, a remote or a virtual provider visit or in or during a remote or a distance examination. In this regard, the healthcare provider can be provided with any and/or all information regarding the individual or the patient in order to conduct a full and complete examination or evaluation of the individual or the patient, or to make or arrive at a diagnosis based on any and/or all information regarding the individual or the patient, or to prescribed a treatment based on any and/or all any and/or all information regarding the individual or the patient. As a further result, the healthcare provider can be provided with access to the individual's or the patient's healthcare records, files, or history, in order to properly or completely enter notes or any other information regarding the individual or the patient as well as any information, observations, examination findings, or examinations results, obtained by, made by, or obtained during, the remote or the virtual provider visit or in or during the remote or the distance examination, so as to assure that any and/or all interactions with or between the individual or the patient and any healthcare provider, including information obtained from or during remote or the virtual provider visits or in or during remote or the distance examinations are documented in the individual's or the patient's healthcare records, files, or history.

In a preferred embodiment, the apparatus 100 and method of the present invention can be utilized to allow an individual, a patient, or a caregiver of or for the individual or the patient to engage in a video call, a video chat session, or a videoconference, with a healthcare provider in order to facilitate or to provide for a remote or virtual office visit with the healthcare provider or in order to facilitate or to provided for a remote or distance consultation or examination with or by a healthcare provider.

In a preferred embodiment, it is envisioned that any number, kinds, or types, of healthcare providers, who or which have registered with the apparatus 100 in order to engage in video calls, video chat sessions, or videoconferences, in order to provide remote or virtual office visits or in order to provide remote or distance consultations or examinations with and for any individuals or patients, or caregivers, can store any data and/or information regarding his, or her name, address, telephone number, e-mail address, text messaging information or number(s), or any other contact information, credentials, education, practice area(s), insurance(s) accepted, fees, telephone number(s) or IP address(es) for video calls, video chat sessions, videoconferences, work schedule(s), appointment schedule(s), and/or any other information needed or desired for providing information regarding the healthcare provider to an individual, a patient, or a caregiver of or for the individual or the patient, and/or for allowing the individual, the patient, or the caregiver of the individual or the patient, to schedule a video call, a video chat session, or a videoconference, with the healthcare provider.

In a preferred embodiment, any of the above-described or herein-described data and/or information regarding the healthcare provider, for any number of healthcare providers, can be stored in, and can be searchable from, the database 10H of the central processing computer 10. In the preferred embodiment, any of the above-described or herein-described data and/or information regarding the healthcare provider, for any number of healthcare providers, can be also be stored in, and can be searchable from, the database 20H of any provider communication device 20. In the preferred embodiment, any of the above-described or herein-described data and/or information regarding the healthcare provider, for any number of healthcare providers, can be also be stored in, and can be searchable from, the database 40H of any user communication device 40.

In a preferred embodiment, it is envisioned that the individual, the patient, or the caregiver of or for the individual or the patient, can access the central processing computer 10 or a respective provider communication device 20 with or using his or her user communication device 40, or by accessing data and/or information stored in his or her communication device 40, at any time, in order to search for and/or to select a healthcare provider(s) with whom he or she can schedule a video call, a video chat session, or a videoconference. The individual, the patient, or the caregiver of or for the individual or the patient, can select the individual's or the patient's current healthcare provider, current primary care provider, or a new or different healthcare provider, or a healthcare provider having a certain specialization, or a certain availability. The individual or the patient, or the caregiver of or for the individual or the patient, can make an appointment for a video call, a video chat session, or a videoconference, with the healthcare provider with or using the user communication device 40. At the time of making the appointment the individual, patient, or caregiver, can provide a telephone number, a call number, a conference call number, or an IP address, associated with the user communication device 40 which the individual, the patient, or the caregiver, will use for the video call, the video chat session, or the videoconference. At the time of making the appointment, the individual, the patient, or the caregiver, can also be provided with the telephone number, the call number, the conference call number, or the IP address, associated with the provider communication device 20 which will be used by the healthcare provider for the video call, the video chat session, or the videoconference. At the time of making the appointment, the individual, the patient, or the caregiver, can also be provided with an instruction as to whether he or she is to call the healthcare provider at the appointment time, or whether the healthcare provider will call the individual, the patient, or the caregiver, at the appointment time.

In instances when the appointment is being made via the central processing computer 10, the appointment can be made via the individual's or the patient's electronic medical record, file, or history, which is stored in the database 10H of the central processing computer 10, and information regarding the appointment can be stored in the individual's or the patient's electronic medical record, file, or history as well as in the healthcare provider's work schedule or in an appointment schedule of the healthcare provider. In instances when the appointment is being made via a provider communication device 20, the appointment can be made via the individual's or the patient's electronic medical record, file, or history, which is stored in the database 20H of the provider communication device 20, and information regarding the appointment can be stored in the individual's or the patient's electronic medical record, file, or history as well as in the healthcare provider's work schedule or in an appointment schedule of the healthcare provider. In instances when the appointment is being made via a user communication device 40, the appointment can be made via the individual's or the patient's electronic medical record, file, or history, or personal healthcare record, which is stored in the database 40H of the user communication device 40, and information regarding same can be automatically transmitted to and stored in the individual's or the patient's electronic medical record, file, or history in the database 10H of the central processing computer 10 as well as in the healthcare provider's work schedule or in an appointment schedule of the healthcare provider.

In a preferred embodiment, the central processing computer 10 can be programmed so that, once an appointment for a video call, a video chat session, or a videoconference, has been made, the central processing computer 10 can automatically generate a message (hereinafter an "appointment message") containing information regarding the appointment, and/or the time and date of same, which has been scheduled and will transmit same to the provider communication device 20 of or associated with the healthcare provider with whom the appointment has been made, and will also transmit same to the user communication device(s) 40 of or associated with the individual, the patient, or the caregiver. In a preferred embodiment, the provider communication device 20 with which an appointment has been made can also be programmed so that, once an appointment for a video call, a video chat session, or a videoconference, has been made, the provider communication device 20 can automatically generate a message (hereinafter an "appointment message") containing information regarding the appointment, and/or the time and date of same, which has been scheduled and will transmit same to any other provider communication device 20 of or associated with the healthcare provider with whom the appointment has been made, and will also transmit same to the user communication device(s) 40 of or associated with the individual, the patient, or the caregiver. In a preferred embodiment, the user communication device 40 with which an appointment has been made can also be programmed so that, once an appointment for a video call, a video chat session, or a videoconference, has been made, the user communication device 40 can automatically generate a message (hereinafter an "appointment message") containing information regarding the appointment, and/or the time and date of same, which has been scheduled and will transmit same to the central processing computer 10, to any provider communication device 20 of or associated with the healthcare provider with whom the appointment has been made, and/or to any other user communication device(s) 40 of or associated with the individual, the patient, or the caregiver.

In a preferred embodiment, the central processing computer 10 can also be programmed so that, once an appointment for a video call, a video chat session, or a videoconference, has been made, the central processing computer 10 can automatically generate a reminder message(s) (hereinafter an "reminder message") containing information for reminding each of the individual, the patient, or the caregiver, and the healthcare provider of the appointment for the video call, the video chat session, or the videoconference. The reminder message or reminder messages can be transmitted to each of the user communication device(s) 40 of or associated with the individual, the patient, or the caregiver, and to the provider communication device 20 of or associated with the healthcare provider.

In a preferred embodiment, any of the appointment messages and/or reminder messages described herein can include the appointment time, the name of the healthcare provider, and the telephone number, the call number, the conference call number, or the IP address, associated with the provider communication device 20 which will be used by the healthcare provider for the video call, the video chat session, or the videoconference, and the name of the individual, the patient, or the caregiver, and the telephone number, the call number, the conference call number, or the IP address, associated with the user communication device 40 which the individual, the patient, or the caregiver, will use for the video call, the video chat session, or the videoconference, and an instruction, if any, as to who is to initiate the video call, the video chat session, or the videoconference, such as, for example, whether the individual, the patient, or the caregiver, is to call the healthcare provider at the appointment time or whether the healthcare provider is to call the individual, the patient, or the caregiver, at the appointment time.

In a preferred embodiment, any of the herein-described appointment messages and/or reminder messages can be stored in the individual's or the patient's electronic healthcare record, file, or history, in the database 10H of the central processing computer 10 and/or in the database 40H of the user communication device 40, such as in a healthcare provider appointments section or field of same. Likewise, any of the herein-described appointment messages and/or reminder messages can be stored in the healthcare provider's records or files which can also be stored in the database 10H of the central processing computer 10 and/or in the database 20H of the provider communication device 20 such as in an appointments section or field of same.

In a preferred embodiment, any of the herein-described appointment messages or reminder messages can also contain a link or a hyperlink to the electronic healthcare record, file, or history, of the individual or the patient. Any of the herein-described appointment messages or reminder messages can also contain a link or a hyperlink for allowing each of the individual, the patient, or the caregiver of or for the individual or the patient to initiate a video call, a video chat session, or a videoconference, described herein via the link or the hyperlink.

In another preferred embodiment, a healthcare provider or any number of healthcare providers can be available for a video call, a video chat session, or a videoconference, at any given time and an individual, a patient, or a caregiver for the individual or the patient, can simply access the central processing computer 10, see which healthcare provider or healthcare providers are available and can immediately initiate a video call, a video chat session, or a videoconference, with an available healthcare provider.

In a preferred embodiment, the apparatus 100 can be utilized to in order to the healthcare provider to gain authorized access to the individual's or the patient's electronic healthcare records, files, or history, prior to and/or during the video call, the video chat session, or the videoconference, with the individual, the patient, or the caregiver of or for the individual or the patient. In this regard, the healthcare provider can review the individual's or the patient's electronic healthcare records, files, or history, prior to and/or during the video call, the video chat session, or the videoconference, obtain information from same, enter notes, observations, or examination findings, into same, and/or enter information regarding a diagnosis, a treatment, or a treatment plan into same, and/or enter information regarding and/or prescribe a medication or a drug, prescribed a therapy or any kind or type, prescribed a treatment of any kind or kind, and/or make a referral to another healthcare provider. In a preferred embodiment, any and/or all information, including a video or a video clip, and/or an audio, a video, and/or an audio and video recording, of the video call, the video chat session, or the videoconference, can be recorded and stored in the individual's or the patient's electronic healthcare records, files, or history.

Figure 11:
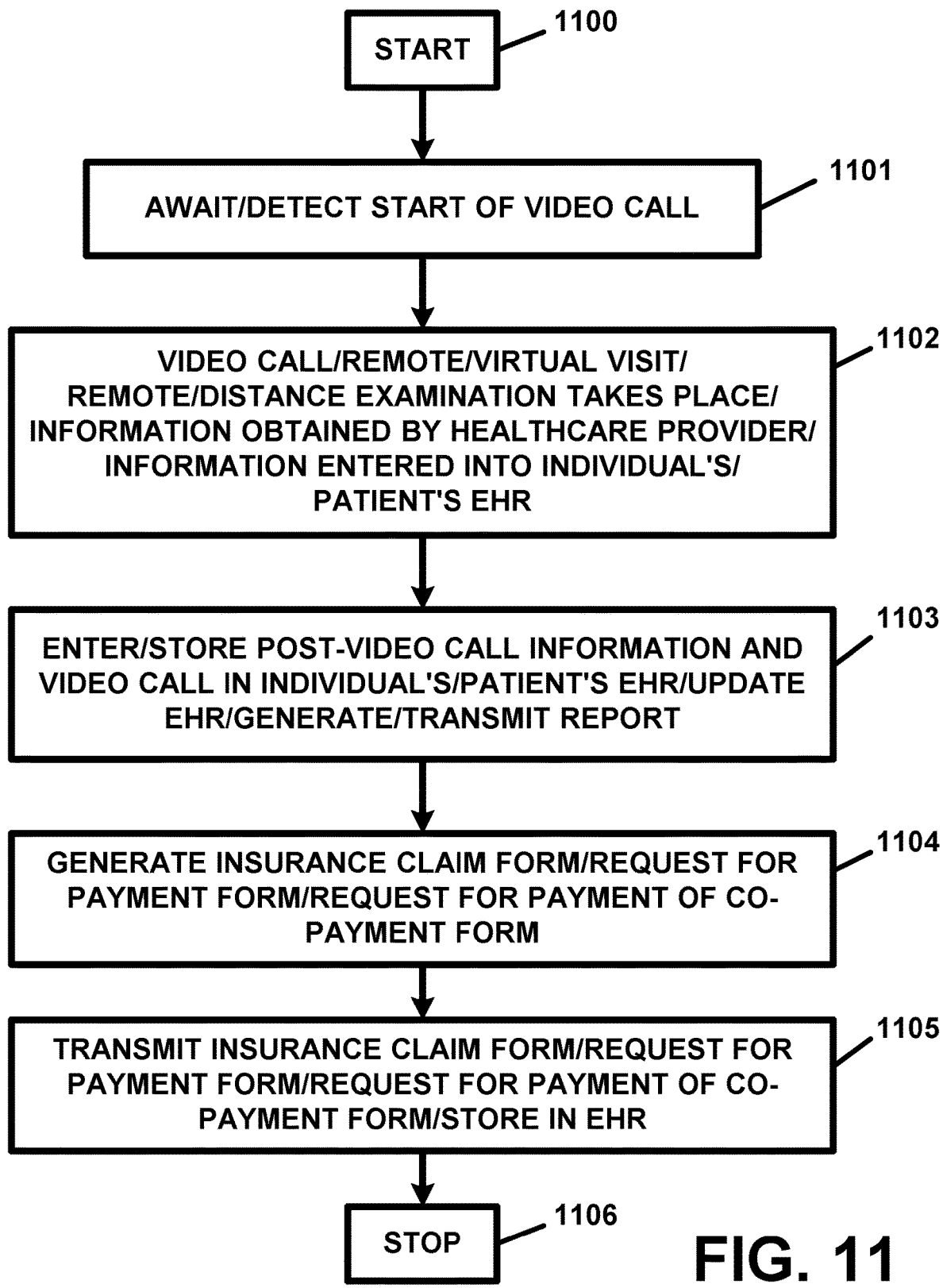
FIG. 11 illustrates a preferred embodiment method of utilizing the apparatus of the present invention, in flow diagram form.

FIG. 11 illustrates a preferred embodiment method for utilizing the apparatus 100 and method of the present invention, in flow diagram form. The preferred embodiment of FIG. 11 will be described as being utilized in connection with a video call between an individual, a patient, or a caregiver, and a healthcare provider. However, it is to be understood and is important to note that the preferred embodiment of FIG. 11 can also be utilized in a same, a similar, and/or an analogous, manner in connection with a video chat session or a videoconference with and/or between an individual, a patient, or a caregiver, and a healthcare provider. It is also to be understood and is important to note that, although described as being utilized in connection with a video call between an individual, a patient, or a caregiver, and a healthcare provider, the embodiment of FIG. 11 can also be utilized in a same, a similar, and/or an analogous, manner in connection with any video call, video chat session, or videoconference, involving and/or with and/or between any of the herein-described individuals, patients, caregivers, healthcare providers, other providers, healthcare insurers, healthcare payers, and/or intermediaries.

With reference to FIG. 11, the operation of the apparatus 100 commences at step 1100. At step 1101, the apparatus 100 will await and detect the start of the video call. In a preferred embodiment, depending on what may be pre-arranged or pre-selected, the individual, the patient, or the caregiver, can call the healthcare provider by using the his or her user communication device 40 to call the provider communication device 20 of or associated with the healthcare provider, or the healthcare provider can call the individual, the patient, or the caregiver, by using his or her provider communication device 20 to call the user communication device 40 of or associated with the individual, the patient, or the caregiver of or for the individual or the patient. In another preferred embodiment, the video call can be initiated and/or can take place via the central processing computer 10. In another preferred embodiment, the video call can be initiated via a link or a hyperlink in any of the herein-described appointment messages or reminder messages. Any of the herein-described links or hyperlinks in any of the herein-described appointment messages or reminder messages can provide, or be, a link or a hyperlink to, for, or associated with the telephone number, the call number, the conference call number, or the IP address, associated with the provider communication device 20 which will be used by the healthcare provider for the video call as well as the telephone number, the call number, the conference call number, or the IP address, associated with the user communication device 40 which will be used by the individual, the patient, or the caregiver.

In another preferred embodiment, then database 10H of the central processing computer 10 can contain, in the electronic healthcare record, file, or history, of the individual or the patient, and/or in the records or files of the healthcare provider, a link or a hyperlink to, for, or associated with the telephone number, the call number, the conference call number, or the IP address, associated with the provider communication device 20 which will be used by the healthcare provider for the video call as well as the telephone number, the call number, the conference call number, or the IP address, associated with the user communication device 40 which will be used by the individual, the patient, or the caregiver.

In this preferred embodiment, the video call can be initiated by either the individual, the patient, or the caregiver of or for the individual or the patient using either the telephone number, the call number, the conference call number, or the IP address, associated with the provider communication device 20 or by using the link or the hyperlink provided in the electronic healthcare record, file, or history, of the individual or the patient, or by using the link or the hyperlink provided in the records or files of the healthcare provider, and/or by using the link or the hyperlink provided in the appointment message or any reminder message. In this preferred embodiment, the video call can be initiated by either the healthcare provider using either the telephone number, the call number, the conference call number, or the IP address, associated with the user communication device 40 of or associated with the individual, the patient, or the caregiver, or by using the link or the hyperlink provided in the electronic healthcare record, file, or history, of the individual or the patient, or by using the link or the hyperlink provided in the records or files of the healthcare provider.

Once the video call has been initiated and detected by the apparatus 100 and/or the central processing computer 10, at step 1101, the operation of the apparatus 100 will proceed to step 1102 and the video call can proceed. In a preferred embodiment, the video call can take place with a cellular telephone, a smart phone, a Smartphone, or a personal digital assistant being utilized as the user communication device 40 used by the individual, the patient, or the caregiver, and/or as the provider communication device 20 used by the healthcare provider. In another preferred embodiment, the video call can take place with a personal computer, a laptop computer, a tablet, a tablet computer, a cellular telephone, a smart phone, a Smartphone, or a personal digital assistant, or a watch being utilized as the user communication device 40 used by the individual, the patient, or the caregiver, and/or as the provider communication device 20 used by the healthcare provider. In a preferred embodiment, the video call can take place, and any and/or all data and information can be provided, via the display device 20E of the healthcare provider communication device 20 and via the display device 40E of the user communication device 40.

In a preferred embodiment, the video call can be initiated via a link or a hyperlink contained in the individual's or the patient's electronic healthcare record, file, or history, and the video call can take place via the central processing computer 10 and/or via the individual's or the patient's electronic healthcare record, file, or history, so that information regarding the time and date of the video call, and/or any information regarding any actions taken by the individual, the patient, or the caregiver, or the healthcare provider, and/or any information regarding any information accessed from or in the individual's or the patient's electronic healthcare record, file, or history, and/or any information regarding any notes or information or data entered into, recorded by, or stored in, the individual's or the patient's electronic healthcare record, file, or history, by the individual, the patient, or the caregiver, or the healthcare provider, and/or the video call itself, can be monitored, recorded, and/or stored, in the individual's or the patient's electronic healthcare record, file, or history. In another preferred embodiment, the video call can also take place by and between the provider communication device 20 and the user communication device 40, with each of the healthcare provider communication device 20 and/or the user communication device 40 being in communication with, and/or having access to, the central processing computer 10 and/or being in communication with and/or having access to, the individual's or the patient's electronic healthcare record, file, or history, in the database 10H of the central processing computer 10.

In a preferred embodiment, at the start of the video call, and at or during step 1102, the healthcare provider can take a picture or photograph of the individual, the patient, or the caregiver, using the healthcare provider communication device 20, which picture or photograph can be stored and can be used for verifying the identity of the individual, the patient, or the caregiver as described herein. In a preferred embodiment, at or during step 1102, the healthcare provider can also take a picture or photograph of the himself or herself, which picture or photograph can be stored and can be used for verifying the identity of the of the healthcare provider as described herein.

Thereafter, at step 1102, the video call can then proceed and the healthcare provider can conduct the remote office visit or the virtual office visit and/or the remote examination or the distance examination with the individual, the patient, or the caregiver. In instances where the individual or the patient is on the video call with out a caregiver, then the video call can take place between the individual or the patient and the healthcare provider. In instances where a caregiver is on the video call, then the video call can take place with the individual or the patient, the caregiver and the healthcare provider. In instances where only the caregiver is on the video call without the individual or the patient, then the video call can take place with the caregiver and the healthcare provider. In a preferred embodiment, the video call can be recorded by or with the central processing computer 10, by or with the provider communication device 20, and/or by or with the user communication device 40 for storage in each of the central processing computer 10, the provider communication device 20, and/or the user communication device 40. In this regard, the healthcare provider or another healthcare provider, or the individual, the patient, the caregiver, or another caregiver, can replay or review same at any time.

At step 1102, the healthcare provider can conduct the remote office visit or the virtual office visit and/or the remote examination or the distance examination with the individual, the patient, or the caregiver, by ascertaining the individual's or the patient's condition, symptoms, or the nature of the individual's or the patient's illness, sickness or state of health. At step 1102, the healthcare provider can also obtain information regarding a healthcare history of or for the individual or the patient or any information regarding a family healthcare history of or for the individual or the patient. At step 1102, the healthcare provider can also obtain information regarding any allergies the individual or the patient may have, any prescription medications or drugs the individual or the patient may be taking. At step 1102, the healthcare provider can also obtain any other information needed or desired for diagnosing and/or treating the individual or the patient during the video call.

At step 1102, the individual or the patient, or the caregiver, can also, if not previously provided to the healthcare provider, provide the healthcare provider with authorization and/or permission to access and review the individual's or the patient's electronic healthcare record, file, or history, and/or to review any data and/or information contained therein. In a preferred embodiment, the healthcare provider can also be provided with authorization or permission to access and review the individual's or the patient's electronic healthcare record, file, or history, prior to the video call. Such authorization or permission can also be provided at the time the appointment is scheduled by the individual, the patient, or the caregiver of or for the individual or the patient.

At step 1102, the healthcare provider can access, and can review or can obtain any data and/or information contained in, the individual's or the patient's electronic healthcare record, file, or history. At step 1102, the healthcare provider can also request and/or conduct a visual examination of the individual or the patient or of a body part of the individual or the patient in and/or under appropriate circumstances by asking the individual or the patient, or the caregiver, to use and/or position the camera associated with the user communication device 40 in order to allow the healthcare provider to look at or view the individual or the patient or any body part of the individual or the patient. At step 1102, the individual, the patient, or the caregiver, can also transmit any data and/or information stored in any personal health record of or for the individual or the patient which might be stored on or in the user communication device 40 which is being utilized for the video call. At step 1102, the individual, the patient, or the caregiver, can also transmit any data and/or information stored in any electronic healthcare record, file, or history, of or for the individual or the patient which might be stored on or in the user communication device 40 which is being utilized for the video call.

At step 1102, the healthcare provider can also ask that the individual, the patient, or the caregiver, obtain and/or transmit any data and/or information from any healthcare measuring device or equipment, any healthcare measurement device or equipment, or any healthcare monitoring device or equipment, or obtain and/or transmit any data and/or information from any healthcare equipment input device, healthcare measurement input device, or healthcare monitoring input device described herein, which can be utilized in connection or in conjunction with the user communication device 40 and/or which has been described herein as being utilized as an input device for or in connection with the user communication device 40. In this regard, the healthcare provider can also request that the individual, the patient, or the caregiver, obtain and/or transmit data and/or information obtained by a pulse rate monitor, a blood pressure monitor, an electro-cardiogram, a blood-sugars monitor, any device which can acquire, receive, generate and/or provide, digital data such as medical, healthcare, bio-metric, physiological, and/or any other kind of healthcare data and/or healthcare-related data, a heart rate monitor, a pulse rate monitor, or EKG machine, a thermometer, a digital thermometer, a stethoscope, a heart rate monitor or measurement device, a pulse rate monitor or measurement device, a blood pressure monitor or measurement device, a blood pressure measurement device, a blood analysis device or machine, a respirator, a respiration monitoring or measurement device, a dialysis machine, a dialysis device, electrocardiograph (EKG) machine or device, electrocephalograph (EEG)

machine or device, electromyograph (EMG) machine or device, a magnetic resonance imaging (MRI) machine or device, X-ray machine or device, medical imaging machine or device, thermal imaging machine or device, a heart sound monitor or measurement device, a lung sound monitoring or measurement device, respiration rate monitoring or measurement device, a laprascopic device, an arthroscopic device, a vascular testing device, a catheter device, a cardiac performance testing, monitoring, or measurement device, a pulmonary performance testing, monitoring, or measurement device, a vascular system performance monitoring or measurement device, a vascular system testing, monitoring, or measurement device, a metabolism monitoring or measurement device, a sonogram imaging device, a sonogram measurement device, a sonograph device, an optical response device, an optical response measurement device, an intravenous device, an arterial blood pressure measurement or monitoring device, a respiration rate measurement or monitoring device, an ultrasound imaging device, an ultrasound measurement device, a CAT SCAN device, an optical metabolism measurement or monitoring device, a radiotelemetric device, a doppler medical device, a mammogram device, a carbon dioxide detection or measurement device, a carbon monoxide detection or measurement device, a transvascular impedance measurement or monitoring device, an ultrasonic imaging device, a bone conduction device, a brain function scan analyzer device, external pulse cardiac monitoring or measurement device, a fetal heart rate measurement, monitoring, or probing, device, an endotrachial cardiac monitoring device, a finger tip blood pressure monitoring device, a psychological monitoring device, a surgical instrument, a vital signs measurement device, ear pressure regulating device, phonocardiograph device, acoustic aneurysm detector device, blood oxygen detection device, esophageal probing device, ultrasonic probing device, ausculoscope, vital signs monitoring system, heart activity monitoring device, pulmonary activity monitoring device, sphygmomanometer, esophageal stethoscope, venous pressure measuring device, differential doppler device, physiological data measuring device, body tissue movement device, breathalyzer device, camera probing device, microscopic camera probing device, or any other bio-metric or physiological data measuring device(s) and/or data acquisition device (each of which can be hereinafter also referred to herein as "healthcare equipment" or as a "healthcare measurement device").

At step 1102, the healthcare provider can also perform, during the video call, a remote control operation and/or a remote monitoring operation of, for, or regarding, any of the above-noted items of healthcare equipment or of any healthcare measurement device(s) via a respective link or hyperlink provided in the individual's or the patient's electronic healthcare record, file, or history. Any results or measurements obtained from any healthcare equipment or from any healthcare measurement device(s) can be provided to the healthcare provider via the display device 20E of the healthcare provider communication device 20.

At step 1102, the individual, the patient, or the caregiver, can also access the individual's or the patient's electronic healthcare record, file, or history, during the video call in order to view same along with the healthcare provider. In a preferred embodiment, any video call video and/or any electronic healthcare record, file, or history information, can be presented on the respective provider communication device 20 and/or the user communication device 40 in a split screen format so as to ensure that as much information as possible can be provided to healthcare provider and/or to the individual, the patient, or the caregiver, during the video call. In a preferred embodiment, any video call video and/or audio and/or any electronic healthcare record, file, or history information, can be presented on the respective provider communication device 20 by being displayed, in a split screen format or other suitable format, on the display device 20E and/or by being presented via a speaker of the output device 20I of the provider communication device 20 so as to ensure that as much information as possible can be provided to healthcare provider during the video call. In a preferred embodiment, and any video call video and/or audio and/or any electronic healthcare record, file, or history information, can be presented on the respective user communication device 40 by being displayed, in a split screen format or other suitable format, on the display device 40E and/or by being presented via a speaker of the output device 40I of the user communication device 40 so as to ensure that as much information as possible can be provided the individual, the patient, or the caregiver, during the video call.

At step 1102, the healthcare provider can obtain any other information from the individual, the patient, or the caregiver, or from the individual's or the patient's electronic healthcare record, file, or history, and/or any other data and/or information which the healthcare provider deems to be needed or desired during the video call and/or during the remote office visit or the virtual office visit and/or the remote examination or the distance examination with the individual, the patient, or the caregiver. At step 1102, the healthcare provider can enter any notes, comments, and/or observations, and/or any examination findings, regarding the individual or the patient and/or regarding any data and/or information obtained or reviewed during the video call, into the individual's or the patient's electronic healthcare record, file, or history. At step 1102, the healthcare provider can also make or arrive at a diagnosis for the individual or the patient, and/or can prescribe a treatment, or a course of treatment, or can provide a treatment plan, or can generate or issue a prescription for a drug or a medication, or can generate or issue a prescription for a test or procedure, or can make a referral to another healthcare provider, for the individual or the patient. In a preferred embodiment, the healthcare provider can utilize any information contained in the individual's or the patient's electronic healthcare record, file, or history, in order to take into account any allergies, possible drug or medication interactions, or any other information regarding the individual or the patient which must be considered in making or in arriving at a diagnosis, and/or in prescribing a treatment, or a course of treatment, or in providing a treatment plan, or in generating or issuing a prescription for a drug or a medication, or in generating or issuing a prescription for a test or a procedure, or in making a referral, to another healthcare provider, for the individual or the patient. In a preferred embodiment, any prescription(s) or referral(s) generated or issued during step 1102 can be electronically sent, such as by e-mail, instant message, SMS message, MMS message, or in any other suitable communication device to any provider communication device 20 of or associated with the individual's or the patient's pharmacy or to any other healthcare provider to whom the respective prescription or referral is to be sent.

The healthcare provider can also, as step 1102, recommend that the individual or the patient, or the caregiver of or for the individual or the patient, obtain information from, and/or join or participate in or with, any social network or social networks associated with any of the herein-described social networking computers 80 which are described herein as being utilized in connection with the apparatus 100 of the present invention. The healthcare provider can also, as step 1102, recommend that the individual or the patient, or the caregiver of or for the individual or the patient, obtain information from and/or subscribe to any of the herein-described media computers 90 which are described herein as being utilized in connection with the apparatus 100 of the present invention. Thereafter, the video call can end and the operation of the apparatus 100 will proceed to step 1103.

At step 1103, the healthcare provider can enter any information regarding any notes, comments, observations, examination findings, and/or any other information obtained during the video call into the individual's or the patient's electronic healthcare record, file, or history, so as to update same to include information regarding the video call and the remote office visit or the virtual office visit and/or the remote examination or the distance examination which was conducted during same with the individual, the patient, or the caregiver. At step 1103, the healthcare provider can also store the picture or photograph of the individual, the patient, or the caregiver, which was taken during the video call along with any other information regarding the video call and the remote office visit, for the video call and the remote office visit, in order provide verification regarding the identity of the individual, the patient, or the caregiver. At step 1103, the healthcare provider can also store the picture or photograph of the healthcare provider, which was taken during the video call along with any other information regarding the video call and the remote office visit, for the video call and the remote office visit, in order provide verification regarding the identity of the healthcare provider.

At step 1103, the video call, which can be recorded, can also be stored in the individual's or the patient's electronic healthcare record, file, or history, for retrieval at any time by the healthcare provider or another healthcare provider, or by the individual, the patient, the caregiver, or another caregiver, or by a healthcare insurer or a healthcare payer, or by an intermediary, or by any other authorized person or entity, at any time.

At step 1103, the central processing computer 10 can, after any and/or information obtained during and/or regarding the video call has been entered by the healthcare provider and stored in the individual's or the patient's electronic healthcare record, file, or history, can generate a video call report and/or a remote or virtual office visit report or a remote or distance examination report, containing information regarding the video call and/or information regarding the remote or virtual office visit or the remote of distance examination, any data and information obtained or entered or recorded during the video call, and/or the photograph of the individual, the patient, or the caregiver and/or the picture or photograph of the healthcare provider, and/or any other data and/or information regarding the video call and the remote office visit, and can transmit the video call report and/or the remote or virtual office visit report or a remote or distance examination report in, as, or attached to, an e-mail message or in, as, or attached to, an electronic communication transmission, to the provider communication device 20 of or associated with the individual's or the patient's primary care healthcare provider or any other healthcare provider of the individual or the patient, to a user communication device 40 of or associated with the individual, the patient, or the caregiver or any other caregiver of the individual or the patient, to a payer communication device 30 of or associated with a healthcare insurer or a healthcare payer of the individual or the patient, and/or to an intermediary communication device 50 of or associated with an intermediary.

In a preferred embodiment, the video call report and/or the remote or virtual office visit report or a remote or distance examination report, can contain or include any of the data and/or information obtained from the individual, the patient, or the caregiver, prior to, during or after, the video call, any other information obtained from the individual, the patient, or the caregiver, or any information obtained from the individual's or the patient's electronic healthcare record, file, or history, and/or any other data and/or information which the healthcare provider deems to be needed or desired during the video call and/or during the remote office visit or the virtual office visit and/or the remote examination or the distance examination with the individual, the patient, or the caregiver, any information regarding any of the healthcare provider's notes, comments, observations, or examination findings, regarding the individual or the patient and/or any information regarding any data and/or information obtained or reviewed during the video call, and/or entered into the individual's or the patient's electronic healthcare record, file, or history, or any information regarding any diagnosis arrived or made for the individual or the patient, and/or any information regarding any prescribed treatment or course of treatment, any treatment plan, or any prescription for a drug or a medication, or any prescription for a test or procedure, or any referral to another healthcare provider, for the individual or the patient. In a preferred embodiment, the video call report and/or the remote or virtual office visit report or a remote or distance examination report, can contain or include any information regarding any recommendation that the individual or the patient, or the caregiver of or for the individual or the patient, obtain information from, and/or join or participate in or with, any social network or social networks associated with any of the herein-described social networking computers 80 and/or any recommendation that the individual or the patient, or the caregiver of or for the individual or the patient, obtain information from and/or subscribe to any of the herein-described media computers 90.

In a preferred embodiment, any remote or virtual office visit report or a remote or distance examination report generated at step 1103 can also be stored in the individual's or the patient's electronic healthcare record, file, or history.

At step 1104, the central processing computer 10, which can be programmed to generate and transmit an insurance claim form or a request for payment form, can utilize the information stored at step 1103 in order to generate an insurance claim form or a request for payment form. At step 1104, the central processing computer 10, which can be programmed to generate and transmit a request for payment of co-payment form, can generate a request for payment of co-payment form. In a preferred embodiment, the insurance claim form or a request for payment form and/or the request for payment of co-payment form, can also include, or include as an attachment(s), any one or more of the photograph of the individual, the patient, or the caregiver, the picture or photograph of the healthcare provider, any data and/or information regarding the video call and the remote office visit, the video call report and/or the remote or virtual office visit report or a remote or distance examination report.

At step 1105, the central processing computer 10 can transmit the insurance claim form or a request for payment form, in, as, or attached to, an e-mail message, or in, as, or attached to any other suitable electronic communication transmission, to the payer communication device 30 of or associated with the healthcare insurer or the healthcare payer of the individual or the patient. At step 1105, the central processing computer 10 can also transmit the request for payment of co-payment form in, as, or attached to, an e-mail message, or in, as, or attached to any other suitable electronic communication transmission, to the user communication device 40.

At step 1105, any insurance claim form(s) or a request for payment form(s) and any request for payment of co-payment form(s) generated by, and/or transmitted by, the central processing computer 10, and any attachments, if applicable, can be stored in the individual's or the patient's electronic healthcare record, file, or history. Thereafter, the operation of the apparatus 100 will cease at step 1106.

In this regard, the apparatus 100 and method of the present invention can be utilized to facilitate and/or to conduct remote or virtual healthcare provider visits, consultations, and/or examinations, via and/or through the use of video calls, video chat sessions, and/or videoconferences, with and between an individual, a patient, and/or a caregiver for the individual or the patient. The apparatus 100 and method of the present invention can also be utilized to schedule remote or virtual provider visits, consultations, and/or examinations, via and/or through the use of video calls, video chat sessions, and/or videoconferences, with and between an individual, a patient, and/or a caregiver for the individual or the patient.

In another preferred embodiment, as well as in any and/or all of the embodiments described herein, the apparatus and methods of the present invention can also be utilized in connection with, or in conjunction with, a distributed ledger and with Blockchain technology. In a preferred embodiment, a distributed ledger and Blockchain technology can be utilized along with a central processing computer, in a combined system, wherein certain of the transactions, described herein as being performed by the apparatus, can be processed and/or performed by and/or with a central processing computer and/or certain other transactions can be processed and/or performed by and/or with, and/or using, a distributed ledger and Blockchain technology or Blockchain technologies. In another preferred embodiment, any and/or all transactions, described herein as being performed and/or processed by the apparatus, can also be processed and/or performed by and/or with, and/or using, a distributed ledger and Blockchain technology or Blockchain technologies, and/or using any cryptocurrency Blockchain technology or technologies.

In a preferred embodiment, any type of Blockchain technology can be utilized in connection with the apparatus and methods of the present invention. In a preferred embodiment, for example, the apparatus and methods of the present invention can utilize a distributed ledger(s) along with any Blockchain technology or technologies, Bitcoin Blockchain technology or technologies, Ethereum Blockchain technology or technologies, Bitcoin Cash Blockchain technology or technologies, Litecoin Blockchain technology or technologies, Privacy Coin Bitcoin technology or technologies, and/or any other suitable Blockchain technology or technologies, and/or Smart contracts and/or Smart contract technology or technologies and/or decentralized autonomous organizations (DAOs), decentralized autonomous organizations (DAOs) technology or technologies, and/or any combination of same.

Applicant incorporates by reference herein the subject matter and teachings of "Blockchain Technology Explained" by Alan T. Norman, "Blockchain" by Abraham K. White, "Blockchain—A Practical Guide To Developing Business, Law, And Technology Solutions" by Joseph J. Bambara and Paul R. Allen, and "Blockchain—Ultimate Guide To Understanding Blockchain, Bitcoin, Cryptocurrencies, Smart Contracts And The Future of Money" by Mark Gates, in their entirety, for all of their respective subject matter and teachings regarding distributed ledger technology and/or technologies, Blockchain technology and/or technologies, Bitcoin technology and/or technologies, Bitcoin Blockchain technology and/or technologies, Ethereum technology and/or technologies, Ethereum Blockchain technology and/or technologies, cryptocurrencies, cryptocurrency technology and/or technologies, and/or smart contract technology and/or technologies, and/or decentralized autonomous organizations (DAOs) technologies, and/or peer-to-peer technology and/or technologies, and/or any other technology or technologies related thereto or which can be utilized in conjunction distributed ledgers, Blockchain technologies, Smart contracts, decentralized autonomous organizations (DAOs), and/or cryptocurrencies.

By utilizing a distributed ledger and a suitable Blockchain technology, the apparatus and methods of the present invention can reduce the amount of processing performed by, and reliance on, a central processing computer and/or can eliminate the need for a central processing computer and any centralized entity which might operate the central processing computer.

It is important to note that the distributed ledger and the Blockchain technology utilized with same can also be referred to herein as a "distributed ledger/Blockchain technology", "distributed ledger and Blockchain technology", "distributed ledger/Blockchain technology system", or "distributed ledger and Blockchain technology system", or that the distributed ledger and the Blockchain technology utilized with same can also be referred by using any suitable phrase or terminology indicative of an application or system which utilizes or which includes a distributed ledger which is used with any Blockchain technology or which is used in connection, or in conjunction, with any Blockchain technology.

Figure 12:
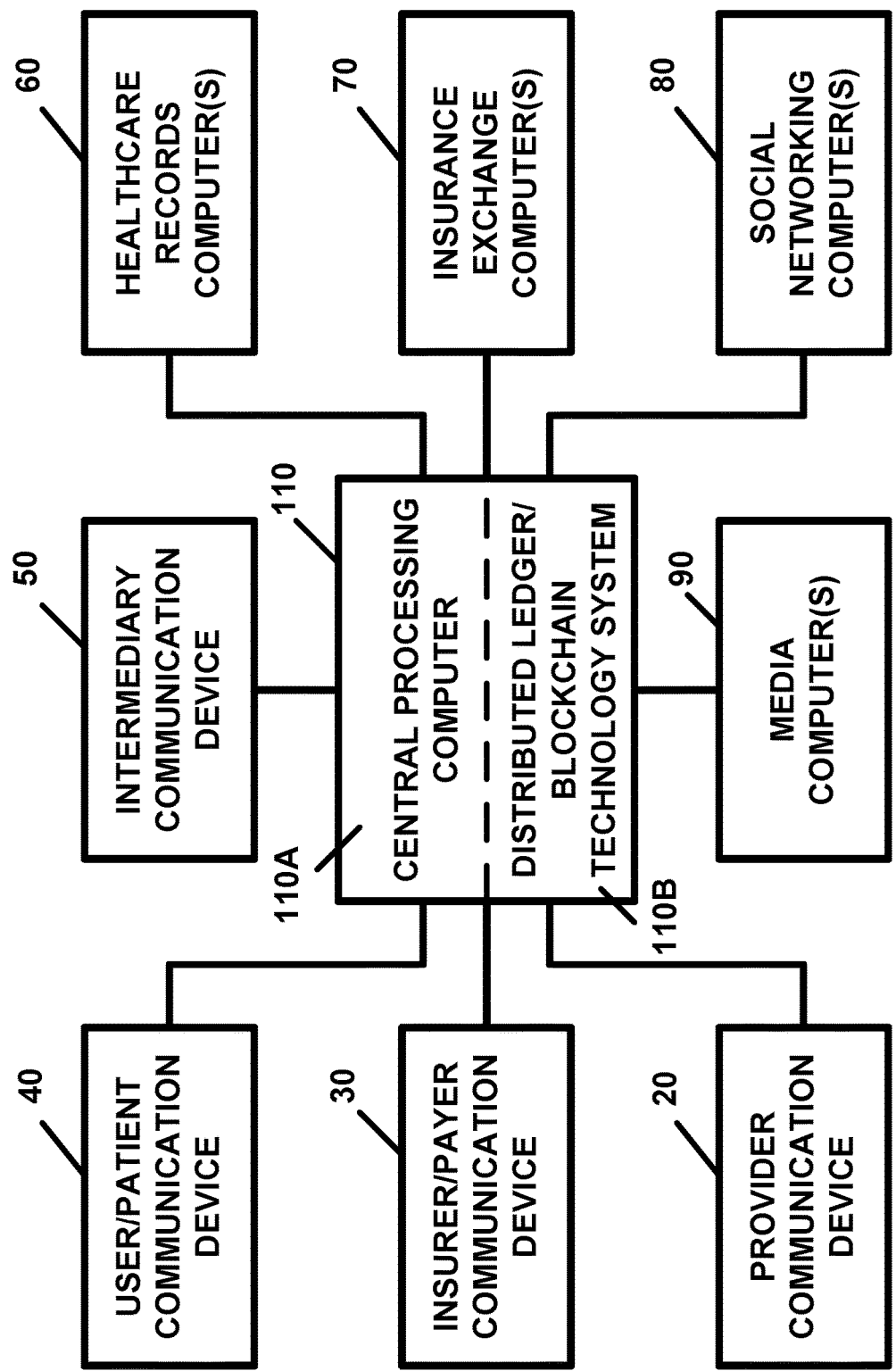
FIG. 12 illustrates another preferred embodiment of the apparatus of the present invention, in block diagram form.

FIG. 12 illustrates another preferred embodiment apparatus of the present invention, which is designated by the reference numeral 200, in block diagram form. With reference to FIG. 12, the apparatus 200 includes a central processing computer and distributed ledger and Blockchain technology system 110 (hereinafter "central processing computer/distributed ledger/Blockchain technology system 110") as well as any of, or each of, the other noted components of the apparatus 100 of FIG. 1. The central processing computer/distributed ledger/Blockchain technology system 110 includes a central processing computer component 110A, which can perform any and/or all of the functions described herein as being performed by the central processing computer 10 and/or the apparatus 100 of FIG. 1, and a distributed ledger and Blockchain technology system component 110B, which can also perform any and/or all of the functions described herein as being performed by the central processing computer 10 and/or the apparatus 100 of FIG. 1.

With reference once again to FIG. 12, the apparatus 200 can also include any number of provider communication devices 20, insurer/payer communication devices 30, user communication devices 40, intermediary communication devices 50, healthcare records computers 60, insurance exchange computers 70, social networking computers 80, and/or media computers 90.

In a preferred embodiment, any and/or all of the various operations, transactions, functions, and/or functionalities, described herein as being performed by the apparatus 100 in the preferred embodiment of FIG. 11 can also be performed by the apparatus 200 of FIG. 12 and, in particular, can be performed by either the central processing computer component 110A of the central processing computer/distributed ledger/Blockchain technology system 110 and/or by the distributed ledger and Blockchain technology system component 110B of the central processing computer/distributed ledger/Blockchain technology system 110. In a preferred embodiment, for example, any and/or all transactions involving any storing of any of the herein-described data and/or information, and/or any data and/or information regarding any video call(s) and/or remote office visit(s), and/or any video call reports and/or the remote or virtual office visit reports or any remote or distance examination reports, in the individual's or the patient's electronic healthcare record, file, or history, can be performed by the distributed ledger and Blockchain technology system component 110B of the central processing computer/distributed ledger/Blockchain technology system 110. In a preferred embodiment, any data and/or information regarding any transactions processed via the distributed ledger and Blockchain technology system component 110B can also be stored in the central processing computer component 110A.

In a preferred embodiment, transactions which are to be processed by the central processing computer component 110A and by the distributed ledger and Blockchain technology system component 110B can be pre-selected or pre-programmed into the central processing computer/distributed ledger/Blockchain technology system 110, and can be re-programmed at any time. In a preferred embodiment, the use of the distributed ledger and Blockchain technology system component 110B can be utilized to provide added security for the individual's or the patient's electronic healthcare record, file, or history, and can also be utilized to prevent healthcare identity theft involving the individual or patient.

The apparatus 100, the apparatus 200, and/or the method, of the present invention can also be utilized to facilitate and/or to conduct remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary. The apparatus 100, the apparatus 200, and/or the method, of the present invention can also be utilized to schedule remote or virtual conferences, discussions, and/or consultations, via and/or through the use of video calls, video chat sessions, and/or videoconferences, with and between an individual, a patient, and/or a caregiver for the individual or the patient, a healthcare provider, a healthcare insurer or a healthcare payer, and/or an intermediary.

Any provider of an individual or patient, any insurer or payer of an individual or patient, any caregiver of an individual or patient, or any other authorized third party, intermediary, person, or entity, can also enter and store any note(s), comment(s), or message(s) in the individual's or patient's electronic healthcare record.

Any insurance claim form or the payment request form can be date stamped and/or time stamped. In this manner, claim or payment request processing can be tracked or monitored so as to facilitate audits of the insurer or payer in order to ascertain if the insurer or payer is properly and/or efficiently handling a claim or payment request for the individual or patient, and/or if the insurer or payer is in compliance with any laws, rules, or regulations, governing claims or payment processing and/or handling. Information regarding the date stamped and/or time stamped claims, including the insurer's or the payer's processing or handling of same, and the response or reply to same, can also be stored by the present invention and can be accessed and/or obtained by any authorized user or entity.

The apparatus 100, the apparatus 200, and/or the method, of the present invention can also generate a co-payment message or a deductible message containing information regarding a co-payment due by the individual or patient to the provider under the individual's or patient's insurance policy or payment program or a deductible which has to be met by the individual or patient under the individual's or patient's insurance policy or payment program.

The apparatus 100, the apparatus 200, and/or the method, of the present invention can also be utilized in connection with or in conjunction with a personal healthcare record which an individual or patient can maintain for himself, herself, and/or for any children, parents, relatives, friends, or any other individuals whom the individual or patient may be providing care for as a caregiver or a person assisting a caregiver for another. In a preferred embodiment, the personal healthcare record can be stored on one or more user or patient communication devices 40 which can include, but which are not limited to a personal computer, a laptop computer, a tablet, a cellular telephone, a wireless telephone, a television, a digital television, a personal digital assistant (PDA), a smart phone, a watch, or any other of the herein-described devices, or other devices, which can be used as a user or patient communication device. The personal healthcare record can be stored in any number of user communication devices.

An individual or patient can utilize the apparatus 100 or the apparatus 200 of the present invention to enter notes, comments, messages, information regarding how they are feeling, information regarding a sickness, an illness, a symptom, information regarding types of medications they must take and time intervals for taking same, information regarding their diet, foods eaten, drinks ingested, exercise activity, provider information, allergies, and/or any other healthcare information, healthcare-related information, wellness information, fitness information, diet information, exercise of fitness information, nutritional information, and/or any other information which can find application in a healthcare or healthcare-related setting or scenario or any other information pertinent to the individual or patient as well as any individual(s) for whom the individual or patient is serving as a caregiver.

An individual or patient can utilize the apparatus 100 or the apparatus 200 of the present invention, at any time and with any suitable user or patient communication device, enter or input, and store in a personal healthcare record, any relevant healthcare information, healthcare-related information, wellness information, fitness information, diet information, exercise of fitness information, nutritional information, and/or any other information which can find application in a healthcare or healthcare-related setting or scenario. The patient communication device 40 can also be programmed to provide timed alerts or messages to remind the individual or patient to take medication, eat certain foods, intake certain liquids, schedule an appointment with a provider, check the status of an insurance claim or a payment claim, to exercise, provide diet or exercise reminders, or to perform any other action or activity for himself or herself or to perform any of the above for a person whom he or she is a caregiver.

The individual or patient can, at any time and from any location, access the apparatus 100 or the apparatus 200 of the present invention and upload or transmit to the central processing computer 10 any and/or all information in his or her personal healthcare record into relevant portions of his or her electronic healthcare record and/or into a portion of same dedicated to receiving and storing the personal healthcare record information. The individual or patient can also download or receive from the central processing computer 10, any data and/or information that is stored in the individual's or patient's electronic healthcare record(s).

The user or patient communication device 40 can also automatically receive, store or record in the personal healthcare record, and transmit to the central processing computer 10, and data and/or information which can be obtain with or from a wearable sensor or implantable sensor or device such as a wearable or implantable heart rate monitor, blood pressure monitor, blood sugar monitor, or any other device or monitor which can monitor a physiological parameter(s) or a biometric parameter(s). The user or patient communication device 40 can be linked via a wireless or Bluetooth or other suitable communication link with one or more of these wearable or implantable sensors. Data and/or information obtained from the wearable or implantable sensors can be transmitted to the central processing computer 10 and stored in the individual's or patient's electronic healthcare record(s).

The user or patient communication device 40 and/or the personal health record utilized in connection with same, can be equipped with hardware and/or software for translating any data and/or information from one language into any other language, for translating audio information into text information for storing in the user or patient communication device, for storing audio information, for translating text information into audio information, for providing reminders to schedule appointments with providers, for providing reminders for scheduled appointments with providers, and/or for providing any other functions which are described herein as being performed in connection with the user or patient communication device 40. The apparatus 100 or the apparatus 200 of the present invention can also be utilized to receive information from an individual or patient regarding a personal healthcare record, store and update an electronic healthcare record with the personal healthcare record information, and thereafter, generate a new personal healthcare record using any new or updated information from the electronic healthcare record(s). The apparatus 100 or the apparatus 200 of the present invention can provide and maintain up-to-date electronic healthcare records and personal healthcare records for individuals or patients.

The user or patient communication device 40 of the apparatus 100 or of the apparatus 200 of the present invention can also be utilized to be a personal healthcare monitoring and/or planning tool or device for monitoring and/or planning healthcare and/or healthcare-related activities, events, occurrences, and/or happenings, for the individual or patient, the individual's or patient's children, parents, relatives, or those for whom the individual or patient serves or acts as a caregiver. The user or patient communication device 40 can also be utilized to be a personal wellness, fitness, and/or nutritional monitoring and/or planning tool or device for monitoring and/or planning wellness or wellness-related, fitness or fitness-related, and/or nutritional or nutritional-related, activities, events, occurrences, and/or happenings, for the individual or patient, the individual's or patient's children, parents, relatives, or those for whom the individual or patient serves or acts as a caregiver. The user or patient communication device 40 can also be equipped with any needed or desired software or software application or any number of software applications needed, required, or desired for enabling the user or patient communication device to provide the herein-described features, functions, and/or functionality. The apparatus 100 or the apparatus 200 of the present invention can also be utilized to provide information regarding individual and/or family healthcare planning, and/or monitoring, individual and/or family wellness planning and/or monitoring, individual and/or family fitness planning and/or monitoring, and/or individual and/or family nutritional planning and/or monitoring.

The apparatus 100 or the apparatus 200 of the present invention can also be utilized to schedule appointments, and/or remote or virtual office visits or examinations, with providers and to provide automatically generated appointment reminders.

The apparatus 100 or the apparatus 200 of the present invention can also be utilized to provide social networking functionality and capability via an electronic healthcare record(s) or any. Any of the herein-described individuals, patients, caregivers, providers, insurers, payers, third parties, or other entities, can access a social network via any of the electronic healthcare records described herein. Each and every type or kind of electronic healthcare record utilized in or in connection with the present invention can have information, link(s), or hyperlink(s), to any social networking web sites, web pages, support groups, on-line forums, on-link information services, as well as social networking web sites or social networking web pages to or for social networking members, support groups, information providers, healthcare providers, as well as any of the providers, insurers, payers, individuals, patient, third parties, intermediaries, or any other persons or entities described herein who are or who may be members of any social network.

The apparatus 100 or the apparatus 200 of the present invention can also be utilized to provide an individual or patient with information, or a link(s) or a hyperlink(s) to information, regarding a social networking website or a social networking company, any information provided thereby or thereat, or information regarding any social networking support groups or social networking support group members, on-line seminars, forums, chat room discussions, or others, with which or whom the individual or patient may engage upon the individual or patient being diagnosed with an illness, a sickness, or a condition, or upon the individual or patient about to undergo or undergoing a treatment, a procedure, or an operation, or about to embark upon or already involved in a treatment plan.

The providing of the social networking information to the individual or patient can also serve to allow the individual or patient to learn more about a diagnosis, a treatment, or a treatment plan, to interact with others who have been diagnosed with the same or a similar illness, a sickness, or a condition, or others who may be undergoing the same or a similar treatment or who may be following a same or a similar treatment plan. The apparatus 100 or the apparatus 200 of the present invention can also be utilized so as to identify and provide the individual or patient with information or link(s) or hyperlink(s) to a social networking website, a social networking company, a support group or support groups, a member of the social network members of the social network, social networking lectures, classes, or seminars, social networking sponsored lectures, classes, or seminars, social networking discussions, question and answer sessions, or informational or other forums, or any other social networking or social networking sponsored activities or events, for any number of social networks. The apparatus 100 or the apparatus 200 of the present invention can also be utilized in a same, similar, or analogous manner, in order to process and/or to provide veterinary healthcare information and/or veterinary healthcare-related information for and regarding any kind or type of animal or animals or any type or kind of pet or pets. The present invention can also be utilized as a clearinghouse for facilitating the offering, selling, buying, trading, and/or other commerce and/or transactions, involving healthcare and/or healthcare-related services, products and/or goods.

The apparatus 100 or the apparatus 200 of the present invention can also provide for cloud-based healthcare or healthcare-related data and/or information processing and/or storage, cloud-based electronic healthcare records, cloud-based electronic healthcare records storage and/or retrieval, a cloud-based electronic healthcare records system or platform, and/or cloud based processing and/or storage of any and/or all of the data and/or information described herein as being processed by the apparatus 100, the apparatus 200, and/or the methods, of the present invention.

In any and/or all of the embodiments described herein, any of the herein-described data and/or information, any recorded video calls or video call recordings, and/or any data and/or information regarding, obtained, entered, or recorded, via any video call(s) and/or remote office visit(s), and/or any video call reports and/or the remote or virtual office visit reports or any remote or distance examination reports, and/or any photograph of the individual, the patient, or the caregiver, and/or any picture or photograph of the healthcare provider, can be accessed by any authorized user by accessing same via the central processing computer 10 or the via the central processing computer component 110A of the of the central processing computer/distributed ledger/Blockchain technology system 110.

In any and/or all of the embodiments described herein, data and/or information regarding any of the herein-described insurance claims, claims for payment, and/or any other request for a payment, for, regarding, or relating to, any video call, video chat session, or videoconference, can contain, or can contain as an attachment, a copy of a recording of the video call, the video chat session, or the videoconference.

In any and/or all of the embodiments described herein, data and/or information regarding any of the herein-described insurance claims, claims for payment, and/or any other request for a payment, for, regarding, or relating to, any video call, video chat session, or videoconference, can be stored in the electronic healthcare record of or for the individual or the patient using the distributed ledger and/or blockchain technology system.

While the present invention has been described and illustrated in various preferred and alternate embodiments, such descriptions are merely illustrative of the present invention and are not to be construed to be limitations thereof. In this regard, the present invention encompasses all modifications, variations and/or alternate embodiments, with the scope of the present invention being limited only by the claims which follow.

What is claimed is:

1. A computer-implemented method, comprising:
   storing, in a memory or in a database of a computer, an electronic healthcare record of or for an individual or a patient, wherein the electronic healthcare record contains information provided by, and accessible to, the individual or the patient or a caregiver of or for the individual or the patient, and further wherein the electronic healthcare record contains information provided by, and accessible to, a healthcare provider of the individual or the patient, wherein the information provided by the individual or the patient or the caregiver of or for the individual or the patient is transmitted from a user communication device, of or associated with the individual, the patient, or the caregiver of or for the individual or the patient, to, and is received by, a receiver of the computer, and further wherein the information provided by the healthcare provider is transmitted from a provider communication device, of or associated with the healthcare provider, to, and is received by, the receiver of the computer;
   storing, in the electronic healthcare record of or for the individual or the patient, information regarding an appointment for a video call, a video chat session, or a videoconference, of a remote office visit with the healthcare provider, or a remote or distance examination by the healthcare provider, wherein the appointment is made by the individual or the patient, or by the caregiver of or for the individual or the patient, and further wherein the electronic healthcare record contains a note, a comment, or a message, provided from the individual or the patient, or provided from the caregiver of or for the individual or the patient, at a time of a making of the appointment and in advance of the video call, the video chat session, or the videoconference, of the remote office visit with the healthcare provider, or the remote or distance examination by the healthcare provider, and further wherein the information regarding the appointment contains a first link or a first hyperlink to allow the individual or the patient, a caregiver of or for the individual or the patient, or the healthcare provider, to initiate the video call, the video chat session, or the videoconference, of the remote office visit, or the remote or distance examination;
   generating an appointment message containing information regarding the appointment and containing the first link or the first hyperlink for allowing the individual or the patient, a caregiver of or for the individual or the patient, or the healthcare provider, to initiate the video call, the video chat session, or the videoconference, of the remote office visit, or the remote or distance examination, and further wherein the appointment message contains a second link or a second hyperlink to the electronic healthcare record of or for the individual or the patient;
   transmitting, from a transmitter of the computer, the appointment message to the provider communication device in advance of the video call, the video chat session, or the videoconference, of the remote office visit, or the remote or distance examination;
   providing, via the provider communication device, the healthcare provider with access to the electronic healthcare record of or for the individual or the patient;
   providing, via the provider communication device, the healthcare provider with access to the note, the comment, or the message, provided from the individual or the patient, or provided from the caregiver of or for the individual or the patient, in advance of the video call;
   providing, with the computer, the video call, the video chat session, or the videoconference, of the remote or virtual office visit with the healthcare provider or the remote or distance examination by the healthcare provider, wherein the video call, the video chat session, or the videoconference, is initiated via the first link or the first hyperlink and takes place or occurs between the provider communication device and the user communication device;
   obtaining or recording, with the provider communication device, a picture or a photograph of the individual or the patient, or the caregiver;

obtaining or recording, with the provider communication device, a picture or a photograph of the healthcare provider;

presenting or displaying simultaneously, via a display device of the provider communication device, video of the individual or the patient during the video call, the video chat session, or the videoconference, and information contained in the electronic healthcare record of or for the individual or the patient;

receiving, with the receiver of the computer, information regarding the individual or the patient during the video call, the video chat session, or the videoconference;

receiving, with the receiver of the computer, information input into or entered into the provider communication device by the healthcare provider during or after the video call, the video chat session, or the videoconference, wherein the information input into or entered into the provider communication device is transmitted to the receiver, or receiving information input into or entered into the user communication device by the individual, the patient, or the caregiver of or for the individual or the patient, before, during, or after, the video call, the video chat session, or the video conference, wherein the information input into or entered into the user communication device is transmitted to the receiver;

storing, in the memory or in the database of the computer, a recording of the video call, the video chat session, or the videoconference;

generating, with the computer, a report containing information regarding the video call, the video chat session, or the videoconference, the picture or the photograph of the individual or the patient, or the caregiver, and the picture or the photograph of the healthcare provider, information obtained by the healthcare provider during the video call, the video chat session, or the videoconference, information regarding any notes, comments, observations, or examination findings, made by the healthcare provider, information regarding a diagnosis made by the healthcare provider, information regarding a treatment prescribed by the healthcare provider, information regarding a prescription issued by the healthcare provider, information regarding a referral issued by the healthcare provider, or information regarding a recommendation made by the healthcare provider;

storing the report in the electronic healthcare record of or for the individual or the patient; and transmitting the report to the user communication device.

2. The computer-implemented method of claim 1, further comprising:

transmitting the appointment message or a reminder message to the user communication device or to a second user communication device.

3. The computer-implemented method of claim 1, wherein the note, the comment, or the message, contains text information.

4. The computer-implemented method of claim 1, wherein the note, the comment, or the message, contains video information.

5. The computer-implemented method of claim 1, wherein the note, the comment, or the message, contains audio information.

6. The computer-implemented method of claim 1, further comprising:

receiving information obtained with healthcare equipment.

7. An apparatus, comprising:

a receiver;

a memory or a database, wherein the memory or the database stores an electronic healthcare record of or for an individual or a patient, wherein the electronic healthcare record contains information provided by, and accessible to, the individual or the patient or a caregiver of or for the individual or the patient, and further wherein the electronic healthcare record contains information provided by, and accessible to, a healthcare provider of the individual or the patient, wherein the information provided by the individual or the patient or the caregiver of or for the individual is transmitted from a user communication device, of or associated with the individual, the patient, or the caregiver of or for the individual or the patient, to, and is received by, the receiver, and further wherein the information provided by the healthcare provider is transmitted from a provider communication device, of or associated with a healthcare provider, to, and is received by, the receiver, and further wherein the electronic healthcare record contains information regarding an appointment for a video call, a video chat session, or a videoconference, of a remote office visit with the healthcare provider, or a remote or distance examination by the healthcare provider, wherein information regarding the appointment contains a note, a comment, or a message, provided by the individual, the patient, or the caregiver of or for the individual or the patient, at a time of a making of the appointment and in advance of the video call, the video chat session, or the videoconference, of the remote office visit with the healthcare provider, or the remote or distance examination by the healthcare provider;

a processor, wherein the processor generates an appointment message containing information regarding the appointment and containing a first link or a first hyperlink to allow the individual or the patient, the caregiver of or for the individual or the patient, or the healthcare provider, to initiate the video call, the video chat session, or the videoconference, of the remote office visit, or the remote or distance examination, wherein the appointment message also contains a second link or a second hyperlink to the electronic healthcare record of or for the individual or the patient; and a transmitter, wherein the transmitter transmits the appointment message to the provider communication device, and further wherein the apparatus provides access to the note, the comment, or the message, in advance of the video call, wherein the apparatus transmits, to the provider communication device, information for providing the healthcare provider with access to the electronic healthcare record of or for the individual or the patient before a start of, and during, the video call, the video chat session, or the videoconference, of the remote or virtual office visit with the healthcare provider or the remote or distance examination by the healthcare provider, wherein the apparatus facilitates the video call, the video chat session, or the videoconference, of the remote or virtual office visit with the healthcare provider or the remote or distance examination by the healthcare provider between the provider communication device and the user communication device, wherein the apparatus provides information to the provider communication device to facilitate a simultaneous display of video of the individual or the patient during the video call, the video chat session, or the videoconference, and information contained in the electronic healthcare record of or for the individual or the patient, and further wherein the apparatus receives, from the provider communication device, and stores, a picture or a photograph of the individual or the patient, or the caregiver, and further wherein the apparatus receives from the provider communication device, and stores, a picture or a photograph of the healthcare provider;

wherein the receiver receives information regarding the individual or the patient during the video call, the video chat session, or the videoconference, and further wherein the receiver receives information input into or entered into the provider communication device by the healthcare provider during or after the video call, the video chat session, or the videoconference, wherein the information input into or entered into the provider communication device is transmitted to the receiver or to the apparatus, or wherein the receiver or the computer receives information input into or entered into the user communication device by the individual, the patient, or the caregiver of or for the individual or the patient, before, during, or after, the video call, the video chat session, or the video conference, wherein the memory or the database stores a recording of the video call, the video chat session, or the videoconference, and further wherein the processor or the apparatus generates a report containing information regarding the video call, the video chat session, or the videoconference, the picture or the photograph of the individual or the patient, or the caregiver, and the picture or the photograph of the healthcare provider, information obtained by the healthcare provider during the video call, the video chat session, or the videoconference, information regarding any notes, comments, observations, or examination findings, made by the healthcare provider, information regarding a diagnosis made by the healthcare provider, information regarding a treatment prescribed by the healthcare provider, information regarding a prescription issued by the healthcare provider, information regarding a referral issued by the healthcare provider, or information regarding a recommendation made by the healthcare provider, and further wherein the report is stored in the electronic healthcare record of or for the individual or the patient, and further wherein the apparatus transmits the report to the user communication device.

8. The apparatus of claim 7, wherein the video call, the video chat session, or the videoconference, takes place in communication with, in connection with, in conjunction with, or in association with, the electronic healthcare record of the individual or the patient or information contained in the electronic healthcare record of the individual or the patient.

9. The apparatus of claim 7, wherein the computer or the transmitter transmits appointment message or a reminder message to the user communication device or to a second user communication device.

10. The apparatus of claim 7, wherein the note, the comment, or the message, contains text information.

11. The apparatus of claim 7, wherein the note, the comment, or the message, contains video information.

12. The apparatus of claim 7, wherein the note, the comment, or the message, contains audio information.

13. The apparatus of claim 7, wherein the apparatus receives information obtained with healthcare equipment.

* * * * *